(12) United States Patent
Krieg et al.

(10) Patent No.: US 7,956,043 B2
(45) Date of Patent: Jun. 7, 2011

(54) 5' CPG NUCLEIC ACIDS AND METHODS OF USE

(75) Inventors: Arthur M. Krieg, Wellesley, MA (US); Marion Jurk, Dormagen (DE); Jorg Vollmer, Dusseldorf (DE); Eugen Uhlmann, Glashuetten (DE)

(73) Assignees: Coley Pharmaceutical Group, Inc., New York, NY (US); Coley Pharmaceutical GmbH, Dusseldorf (DE)

( * ) Notice: Subject to any disclaimer, the term of this patent is extended or adjusted under 35 U.S.C. 154(b) by 1622 days.

(21) Appl. No.: 10/735,592

(22) Filed: Dec. 11, 2003

(65) Prior Publication Data

US 2004/0171571 A1    Sep. 2, 2004

Related U.S. Application Data

(60) Provisional application No. 60/432,409, filed on Dec. 11, 2002, provisional application No. 60/506,108, filed on Sep. 25, 2003.

(51) Int. Cl.
 A61K 45/00  (2006.01)
 A61K 47/00  (2006.01)
 A61K 31/70  (2006.01)
 A01N 43/04  (2006.01)

(52) U.S. Cl. .................. 514/44 R; 424/278.1
(58) Field of Classification Search .......... 536/23.1, 536/25.6; 514/44
 See application file for complete search history.

(56) References Cited

U.S. PATENT DOCUMENTS

| | | |
|---|---|---|
| 3,906,092 A | 9/1975 | Hilleman et al. |
| 4,806,463 A | 2/1989 | Goodchild et al. |
| 5,004,810 A | 4/1991 | Draper |
| 5,023,243 A | 6/1991 | Tullis |
| 5,087,617 A | 2/1992 | Smith |
| 5,166,195 A | 11/1992 | Ecker |
| 5,194,428 A | 3/1993 | Agrawal et al. |
| 5,248,670 A | 9/1993 | Draper et al. |
| 5,264,423 A | 11/1993 | Cohen et al. |
| 5,268,365 A | 12/1993 | Rudolph et al. |
| 5,276,019 A | 1/1994 | Cohen et al. |
| 5,416,203 A | 5/1995 | Letsinger |
| 5,457,189 A | 10/1995 | Crooke et al. |
| 5,475,096 A | 12/1995 | Gold et al. |
| 5,514,577 A | 5/1996 | Draper et al. |
| 5,514,788 A | 5/1996 | Bennett et al. |
| 5,527,899 A | 6/1996 | Froehler |
| 5,543,152 A | 8/1996 | Webb et al. |
| 5,576,208 A | 11/1996 | Monia et al. |
| 5,576,302 A | 11/1996 | Cook et al. |
| 5,582,986 A | 12/1996 | Monia et al. |
| 5,587,361 A | 12/1996 | Cook et al. |
| 5,594,122 A | 1/1997 | Friesen |
| 5,595,756 A | 1/1997 | Bally et al. |
| 5,646,126 A | 7/1997 | Cheng et al. |
| 5,663,153 A | 9/1997 | Hutcherson et al. |
| 5,679,647 A | 10/1997 | Carson et al. |
| 5,684,147 A | 11/1997 | Agrawal et al. |
| 5,696,248 A | 12/1997 | Peyman et al. |
| 5,696,249 A | 12/1997 | Gold et al. |
| 5,705,385 A | 1/1998 | Bally et al. |
| 5,723,335 A | 3/1998 | Hutcherson et al. |
| 5,726,160 A | 3/1998 | McMichael |
| 5,753,613 A | 5/1998 | Ansell et al. |
| 5,756,097 A | 5/1998 | Landucci et al. |
| 5,766,920 A | 6/1998 | Babbitt et al. |
| 5,780,448 A | 7/1998 | Davis |
| 5,785,992 A | 7/1998 | Ansell et al. |
| 5,786,189 A | 7/1998 | Locht et al. |
| 5,804,566 A | 9/1998 | Carson et al. |
| 5,814,335 A | 9/1998 | Webb et al. |
| 5,837,243 A | 11/1998 | Deo et al. |
| 5,843,653 A | 12/1998 | Gold et al. |
| 5,849,719 A | 12/1998 | Carson et al. |
| 5,877,309 A | 3/1999 | McKay et al. |
| 5,929,226 A | 7/1999 | Padmapriya et al. |
| 5,932,556 A | 8/1999 | Tam |
| 5,955,059 A | 9/1999 | Gilchrest et al. |
| 5,965,542 A | 10/1999 | Wasan et al. |
| 5,968,909 A | 10/1999 | Agrawal et al. |
| 5,976,567 A | 11/1999 | Wheeler et al. |
| 5,977,340 A | 11/1999 | Pirotzky et al. |
| 5,981,501 A | 11/1999 | Wheeler et al. |
| 5,994,315 A | 11/1999 | Nyce et al. |
| 6,025,339 A | 2/2000 | Nyce et al. |
| 6,027,726 A | 2/2000 | Ansell |
| 6,030,954 A | 2/2000 | Wu et al. |
| 6,031,086 A | 2/2000 | Switzer |
| 6,040,296 A | 3/2000 | Nyce et al. |
| 6,090,791 A | 7/2000 | Sato et al. |

(Continued)

FOREIGN PATENT DOCUMENTS

EP    0 302 758 A1    2/1989

(Continued)

OTHER PUBLICATIONS

Zimmermann et al, In: Vaccine Delivery Strategies, 2002, editors: Dietrich and Goebel, pp. 139-161.*
Lui et al, Immunology, 2005, 115:223-230.*
Lazarczyk et al, Expert Opin. Biol. Ther., 2005, 5/4:525-536.*
Broide, Curr. Allergy Asthma Rep., May 2005, 5/3:182-185 abstract only.*
Dalpke et al, Biodrugs, 2002, 16/6:419-431.*
Marshall et al, DNA and Cell Biology, 2005, 24/2:63-72.*
[No Author Listed] Antiviral Agents Bulletin. 5(6), 1992.
Agrawal et al., Pharmacokinetics of oligonucleotides. Ciba Found Symp. 1997;209:60-75; discussion 75-8.

(Continued)

Primary Examiner — N. M. Minnifield
(74) Attorney, Agent, or Firm — Wolf, Greenfield & Sacks, P.C.; Gregg C. Benson

(57) ABSTRACT

The invention relates to a class of CpG immunostimulatory oligonucleotides containing a 5'TCG motif or a CG at or near the 5' end that are useful for stimulating an immune response.

15 Claims, 19 Drawing Sheets

U.S. PATENT DOCUMENTS

| | | |
|---|---|---|
| 6,110,745 A | 8/2000 | Zhang et al. |
| 6,121,434 A | 9/2000 | Peyman et al. |
| 6,174,872 B1 | 1/2001 | Carson et al. |
| 6,184,369 B1 | 2/2001 | Rando et al. |
| 6,194,388 B1 | 2/2001 | Krieg et al. |
| 6,207,646 B1 | 3/2001 | Krieg et al. |
| 6,214,806 B1 | 4/2001 | Krieg et al. |
| 6,218,371 B1 | 4/2001 | Krieg et al. |
| 6,221,882 B1 | 4/2001 | Macfarlane |
| 6,225,292 B1 | 5/2001 | Raz et al. |
| 6,239,116 B1 | 5/2001 | Krieg et al. |
| 6,339,068 B1 | 1/2002 | Krieg et al. |
| 6,348,312 B1 | 2/2002 | Peyman et al. |
| 6,399,630 B1 | 6/2002 | Macfarlane |
| 6,406,705 B1 | 6/2002 | Davis et al. |
| 6,426,334 B1 | 7/2002 | Agrawal et al. |
| 6,426,336 B1 | 7/2002 | Carson et al. |
| 6,429,199 B1 | 8/2002 | Krieg et al. |
| 6,476,000 B1 | 11/2002 | Agrawal et al. |
| 6,479,504 B1 | 11/2002 | Macfarlane et al. |
| 6,498,147 B2 | 12/2002 | Nerenberg et al. |
| 6,498,148 B1 | 12/2002 | Raz |
| 6,503,533 B1 | 1/2003 | Korba et al. |
| 6,506,386 B1 | 1/2003 | Friede et al. |
| 6,514,948 B1 | 2/2003 | Raz et al. |
| 6,521,637 B2 | 2/2003 | Macfarlane |
| 6,534,062 B2 | 3/2003 | Raz et al. |
| 6,544,518 B1 | 4/2003 | Friede et al. |
| 6,552,006 B2 | 4/2003 | Raz et al. |
| 6,558,670 B1 | 5/2003 | Friede et al. |
| 6,562,798 B1 | 5/2003 | Schwartz |
| 6,589,940 B1 | 7/2003 | Raz et al. |
| 6,605,708 B1 | 8/2003 | Habus et al. |
| 6,610,661 B1 | 8/2003 | Carson et al. |
| 6,613,751 B2 | 9/2003 | Raz et al. |
| 6,620,805 B1 | 9/2003 | Takle et al. |
| 6,653,292 B1 | 11/2003 | Krieg et al. |
| 6,693,086 B1 | 2/2004 | Dow et al. |
| 6,727,230 B1 | 4/2004 | Hutcherson et al. |
| 6,737,066 B1 | 5/2004 | Moss |
| 6,749,856 B1 | 6/2004 | Berzofsky et al. |
| 6,815,429 B2 | 11/2004 | Agrawal |
| 6,821,957 B2 | 11/2004 | Krieg et al. |
| 6,835,395 B1 | 12/2004 | Semple et al. |
| 6,852,705 B2 | 2/2005 | Audonnet et al. |
| 6,943,240 B2 | 9/2005 | Bauer et al. |
| 6,949,520 B1 | 9/2005 | Hartmann et al. |
| 7,001,890 B1 | 2/2006 | Wagner et al. |
| 7,049,302 B1 | 5/2006 | Kensil |
| 7,105,495 B2 | 9/2006 | Agrawal et al. |
| 7,129,222 B2 | 10/2006 | Van Nest et al. |
| 7,183,111 B2 | 2/2007 | Van Nest et al. |
| 7,223,741 B2 | 5/2007 | Krieg |
| 7,250,403 B2 | 7/2007 | Van Nest et al. |
| 7,255,868 B2 | 8/2007 | Fearon et al. |
| 7,262,286 B2 | 8/2007 | Kandimalla et al. |
| 7,271,156 B2 | 9/2007 | Krieg et al. |
| 7,276,489 B2 | 10/2007 | Agrawal et al. |
| 7,279,555 B2 | 10/2007 | Peterson |
| 7,354,711 B2 | 4/2008 | Macfarlane |
| 7,354,909 B2 | 4/2008 | Klinman et al. |
| 7,402,572 B2 | 7/2008 | Krieg et al. |
| 7,410,975 B2 | 8/2008 | Lipford et al. |
| 7,488,490 B2 | 2/2009 | Davis et al. |
| 7,517,861 B2 | 4/2009 | Krieg et al. |
| 7,521,063 B2 | 4/2009 | Klinman et al. |
| 7,524,828 B2 | 4/2009 | Krieg et al. |
| 7,534,772 B2 | 5/2009 | Weiner et al. |
| 7,566,703 B2 | 7/2009 | Krieg et al. |
| 7,569,553 B2 | 8/2009 | Krieg |
| 7,576,066 B2 | 8/2009 | Krieg |
| 7,585,847 B2 | 9/2009 | Bratzler et al. |
| 7,605,138 B2 | 10/2009 | Krieg |
| 7,615,539 B2 | 11/2009 | Krieg et al. |
| 7,666,674 B2 | 2/2010 | Klinman et al. |
| 7,674,777 B2 | 3/2010 | Krieg |
| 7,713,529 B2 | 5/2010 | Krieg et al. |
| 7,723,022 B2 | 5/2010 | Krieg et al. |
| 7,723,500 B2 | 5/2010 | Krieg et al. |
| 7,776,344 B2 | 8/2010 | Hartmann et al. |
| 2001/0021772 A1 | 9/2001 | Uhlmann et al. |
| 2001/0034330 A1 | 10/2001 | Kensil |
| 2001/0036462 A1 | 11/2001 | Fong et al. |
| 2001/0044416 A1 | 11/2001 | McCluskie et al. |
| 2001/0046967 A1 | 11/2001 | Van Nest et al. |
| 2002/0028784 A1 | 3/2002 | Van Nest et al. |
| 2002/0042387 A1 | 4/2002 | Raz et al. |
| 2002/0055477 A1 | 5/2002 | Van Nest et al. |
| 2002/0064515 A1 | 5/2002 | Krieg et al. |
| 2002/0086839 A1 | 7/2002 | Raz et al. |
| 2002/0091097 A1 | 7/2002 | Bratzler et al. |
| 2002/0098199 A1 | 7/2002 | Van Nest et al. |
| 2002/0102255 A1 | 8/2002 | Chang |
| 2002/0107212 A1 | 8/2002 | Van Nest et al. |
| 2002/0137714 A1 | 9/2002 | Kandamilla et al. |
| 2002/0142977 A1 | 10/2002 | Raz et al. |
| 2002/0142978 A1 | 10/2002 | Raz et al. |
| 2002/0156033 A1 | 10/2002 | Bratzler et al. |
| 2002/0164341 A1 | 11/2002 | Davis et al. |
| 2002/0165178 A1 | 11/2002 | Schetter et al. |
| 2002/0168340 A1 | 11/2002 | Agrawal |
| 2002/0192184 A1 | 12/2002 | Carpentier |
| 2002/0198165 A1 | 12/2002 | Bratzler et al. |
| 2003/0022852 A1 | 1/2003 | Van Nest et al. |
| 2003/0026782 A1 | 2/2003 | Krieg et al. |
| 2003/0026801 A1 | 2/2003 | Weiner et al. |
| 2003/0049266 A1 | 3/2003 | Fearon et al. |
| 2003/0050261 A1 | 3/2003 | Krieg et al. |
| 2003/0050263 A1 | 3/2003 | Krieg et al. |
| 2003/0050268 A1 | 3/2003 | Krieg et al. |
| 2003/0055014 A1 | 3/2003 | Bratzler |
| 2003/0059773 A1 | 3/2003 | Van Nest et al. |
| 2003/0060440 A1 | 3/2003 | Klinman et al. |
| 2003/0064064 A1 | 4/2003 | Dina et al. |
| 2003/0064945 A1 | 4/2003 | Akhtar et al. |
| 2003/0072762 A1 | 4/2003 | Van de Winkel et al. |
| 2003/0078223 A1 | 4/2003 | Raz et al. |
| 2003/0087848 A1 | 5/2003 | Bratzler et al. |
| 2003/0091599 A1 | 5/2003 | Davis et al. |
| 2003/0092663 A1 | 5/2003 | Raz et al. |
| 2003/0100527 A1 | 5/2003 | Krieg et al. |
| 2003/0104044 A1 | 6/2003 | Semple et al. |
| 2003/0104523 A1 | 6/2003 | Bauer et al. |
| 2003/0119773 A1 | 6/2003 | Raz et al. |
| 2003/0119774 A1 | 6/2003 | Foldvari et al. |
| 2003/0125279 A1 | 7/2003 | Junghans et al. |
| 2003/0125284 A1 | 7/2003 | Raz et al. |
| 2003/0125292 A1 | 7/2003 | Semple et al. |
| 2003/0129251 A1 | 7/2003 | Van Nest et al. |
| 2003/0129605 A1 | 7/2003 | Yu et al. |
| 2003/0130217 A1 | 7/2003 | Raz et al. |
| 2003/0133988 A1 | 7/2003 | Fearon et al. |
| 2003/0138413 A1 | 7/2003 | Vicari et al. |
| 2003/0139364 A1 | 7/2003 | Krieg et al. |
| 2003/0143213 A1 | 7/2003 | Raz et al. |
| 2003/0147870 A1 | 8/2003 | Raz et al. |
| 2003/0148316 A1 | 8/2003 | Lipford et al. |
| 2003/0148976 A1 | 8/2003 | Krieg et al. |
| 2003/0165478 A1 | 9/2003 | Sokoll et al. |
| 2003/0166001 A1 | 9/2003 | Lipford |
| 2003/0175731 A1 | 9/2003 | Fearon et al. |
| 2003/0176373 A1 | 9/2003 | Raz et al. |
| 2003/0176389 A1 | 9/2003 | Raz et al. |
| 2003/0181406 A1 | 9/2003 | Schetter et al. |
| 2003/0186912 A1 | 10/2003 | Agrawal |
| 2003/0191079 A1 | 10/2003 | Krieg et al. |
| 2003/0199466 A1 | 10/2003 | Fearon et al. |
| 2003/0212026 A1 | 11/2003 | Krieg et al. |
| 2003/0212028 A1 | 11/2003 | Raz et al. |
| 2003/0212029 A1 | 11/2003 | Agrawal et al. |
| 2003/0216340 A1 | 11/2003 | Van Nest et al. |
| 2003/0224010 A1 | 12/2003 | Davis et al. |
| 2003/0225016 A1 | 12/2003 | Fearon et al. |
| 2003/0232074 A1 | 12/2003 | Lipford et al. |
| 2003/0232443 A1 | 12/2003 | Bennett et al. |
| 2003/0232780 A1 | 12/2003 | Carson et al. |
| 2003/0232856 A1 | 12/2003 | Macfarlane |

| Publication No. | Date | Inventors |
|---|---|---|
| 2004/0006010 A1 | 1/2004 | Carson et al. |
| 2004/0006034 A1 | 1/2004 | Raz et al. |
| 2004/0009942 A1 | 1/2004 | Van Nest et al. |
| 2004/0009949 A1 | 1/2004 | Krieg |
| 2004/0013688 A1 | 1/2004 | Wise et al. |
| 2004/0030118 A1 | 2/2004 | Wagner et al. |
| 2004/0038922 A1 | 2/2004 | Haensler et al. |
| 2004/0053880 A1 | 3/2004 | Krieg |
| 2004/0058883 A1 | 3/2004 | Phillips et al. |
| 2004/0067902 A9 | 4/2004 | Bratzler et al. |
| 2004/0067905 A1 | 4/2004 | Krieg |
| 2004/0087534 A1 | 5/2004 | Krieg et al. |
| 2004/0087538 A1 | 5/2004 | Krieg et al. |
| 2004/0092468 A1 | 5/2004 | Schwartz et al. |
| 2004/0092472 A1 | 5/2004 | Krieg |
| 2004/0097719 A1 | 5/2004 | Agrawal et al. |
| 2004/0105872 A1 | 6/2004 | Klinman et al. |
| 2004/0106568 A1 | 6/2004 | Krieg et al. |
| 2004/0115219 A1 | 6/2004 | Ahn et al. |
| 2004/0131628 A1 | 7/2004 | Bratzler et al. |
| 2004/0132677 A1 | 7/2004 | Fearon et al. |
| 2004/0132685 A1 | 7/2004 | Krieg et al. |
| 2004/0136948 A1 | 7/2004 | Fearon et al. |
| 2004/0142469 A1 | 7/2004 | Krieg et al. |
| 2004/0143112 A1 | 7/2004 | Krieg et al. |
| 2004/0147468 A1 | 7/2004 | Krieg et al. |
| 2004/0152649 A1 | 8/2004 | Krieg |
| 2004/0152656 A1 | 8/2004 | Krieg et al. |
| 2004/0152657 A1 | 8/2004 | Krieg et al. |
| 2004/0162258 A1 | 8/2004 | Krieg et al. |
| 2004/0162262 A1 | 8/2004 | Krieg et al. |
| 2004/0167089 A1 | 8/2004 | Krieg et al. |
| 2004/0171150 A1 | 9/2004 | Krieg et al. |
| 2004/0171571 A1 | 9/2004 | Krieg et al. |
| 2004/0181045 A1 | 9/2004 | Krieg et al. |
| 2004/0198680 A1 | 10/2004 | Krieg |
| 2004/0198688 A1 | 10/2004 | Krieg et al. |
| 2004/0229835 A1 | 11/2004 | Krieg et al. |
| 2004/0234512 A1 | 11/2004 | Wagner et al. |
| 2004/0235770 A1 | 11/2004 | Davis et al. |
| 2004/0235774 A1 | 11/2004 | Bratzler et al. |
| 2004/0235777 A1 | 11/2004 | Wagner et al. |
| 2004/0235778 A1 | 11/2004 | Wagner et al. |
| 2004/0247662 A1 | 12/2004 | Dow et al. |
| 2004/0248837 A1 | 12/2004 | Raz et al. |
| 2004/0266719 A1 | 12/2004 | McCluskie et al. |
| 2005/0004061 A1 | 1/2005 | Krieg et al. |
| 2005/0004062 A1 | 1/2005 | Krieg et al. |
| 2005/0004144 A1 | 1/2005 | Carson et al. |
| 2005/0009774 A1 | 1/2005 | Krieg et al. |
| 2005/0013812 A1 | 1/2005 | Dow et al. |
| 2005/0019340 A1 | 1/2005 | Garcon et al. |
| 2005/0026861 A1 | 2/2005 | Kandimalla et al. |
| 2005/0031638 A1 | 2/2005 | Dalemans et al. |
| 2005/0032734 A1 | 2/2005 | Krieg et al. |
| 2005/0032736 A1 | 2/2005 | Krieg et al. |
| 2005/0037403 A1 | 2/2005 | Krieg et al. |
| 2005/0037985 A1 | 2/2005 | Krieg et al. |
| 2005/0043529 A1 | 2/2005 | Davis et al. |
| 2005/0049215 A1 | 3/2005 | Krieg et al. |
| 2005/0049216 A1 | 3/2005 | Krieg et al. |
| 2005/0054601 A1 | 3/2005 | Wagner et al. |
| 2005/0054602 A1 | 3/2005 | Krieg et al. |
| 2005/0059619 A1* | 3/2005 | Krieg et al. ............ 514/44 |
| 2005/0059625 A1 | 3/2005 | Krieg et al. |
| 2005/0059626 A1 | 3/2005 | Van Nest et al. |
| 2005/0064401 A1 | 3/2005 | Olek et al. |
| 2005/0070491 A1 | 3/2005 | Krieg et al. |
| 2005/0075302 A1 | 4/2005 | Hutcherson et al. |
| 2005/0100983 A1 | 5/2005 | Bauer et al. |
| 2005/0101554 A1 | 5/2005 | Krieg et al. |
| 2005/0101557 A1 | 5/2005 | Krieg et al. |
| 2005/0119273 A1 | 6/2005 | Lipford et al. |
| 2005/0123523 A1 | 6/2005 | Krieg et al. |
| 2005/0130911 A1 | 6/2005 | Uhlmann et al. |
| 2005/0130918 A1 | 6/2005 | Agrawal et al. |
| 2005/0148537 A1 | 7/2005 | Krieg et al. |
| 2005/0152921 A1 | 7/2005 | Kim et al. |
| 2005/0158336 A1 | 7/2005 | Diamond et al. |
| 2005/0159351 A1 | 7/2005 | Grate et al. |
| 2005/0159375 A1 | 7/2005 | Srivastava et al. |
| 2005/0169888 A1 | 8/2005 | Hartman et al. |
| 2005/0171047 A1 | 8/2005 | Krieg et al. |
| 2005/0176672 A1 | 8/2005 | Scheule et al. |
| 2005/0181422 A1 | 8/2005 | Bauer et al. |
| 2005/0182017 A1 | 8/2005 | Krieg |
| 2005/0191342 A1 | 9/2005 | Tam et al. |
| 2005/0196411 A1 | 9/2005 | Moss et al. |
| 2005/0197314 A1 | 9/2005 | Krieg et al. |
| 2005/0203039 A1 | 9/2005 | Jeon et al. |
| 2005/0209183 A1 | 9/2005 | Kippenberger et al. |
| 2005/0209184 A1 | 9/2005 | Klinman et al. |
| 2005/0214355 A1 | 9/2005 | Klinman et al. |
| 2005/0215500 A1 | 9/2005 | Krieg et al. |
| 2005/0215501 A1 | 9/2005 | Lipford et al. |
| 2005/0233995 A1 | 10/2005 | Krieg et al. |
| 2005/0233999 A1 | 10/2005 | Krieg et al. |
| 2005/0238660 A1 | 10/2005 | Babiuk et al. |
| 2005/0239732 A1 | 10/2005 | Krieg et al. |
| 2005/0239733 A1 | 10/2005 | Jurk et al. |
| 2005/0239734 A1* | 10/2005 | Uhlmann et al. ............ 514/44 |
| 2005/0239736 A1 | 10/2005 | Krieg et al. |
| 2005/0244379 A1 | 11/2005 | Krieg et al. |
| 2005/0244380 A1 | 11/2005 | Krieg et al. |
| 2005/0245477 A1 | 11/2005 | Krieg et al. |
| 2005/0250726 A1 | 11/2005 | Krieg et al. |
| 2005/0256073 A1 | 11/2005 | Lipford et al. |
| 2005/0267057 A1 | 12/2005 | Krieg |
| 2005/0267064 A1 | 12/2005 | Krieg et al. |
| 2005/0277604 A1 | 12/2005 | Krieg et al. |
| 2005/0277609 A1 | 12/2005 | Krieg et al. |
| 2006/0003955 A1 | 1/2006 | Krieg et al. |
| 2006/0003962 A1 | 1/2006 | Ahluwalia et al. |
| 2006/0019916 A1* | 1/2006 | Krieg et al. ............ 514/44 |
| 2006/0019918 A1 | 1/2006 | Agrawal et al. |
| 2006/0019923 A1 | 1/2006 | Davis et al. |
| 2006/0058251 A1* | 3/2006 | Krieg et al. ............ 514/44 |
| 2006/0058254 A1* | 3/2006 | Dina et al. ............ 514/44 |
| 2006/0089326 A1 | 4/2006 | Krieg et al. |
| 2006/0094683 A1 | 5/2006 | Krieg et al. |
| 2006/0105979 A1 | 5/2006 | Agrawal et al. |
| 2006/0140875 A1 | 6/2006 | Krieg et al. |
| 2006/0154890 A1 | 7/2006 | Bratzler et al. |
| 2006/0172966 A1 | 8/2006 | Lipford et al. |
| 2006/0188913 A1 | 8/2006 | Krieg et al. |
| 2006/0211639 A1 | 9/2006 | Bratzler et al. |
| 2006/0211644 A1 | 9/2006 | Krieg et al. |
| 2006/0217328 A1 | 9/2006 | Kandimalla et al. |
| 2006/0229271 A1 | 10/2006 | Krieg et al. |
| 2006/0241076 A1 | 10/2006 | Uhlmann et al. |
| 2006/0246035 A1 | 11/2006 | Ahluwalia et al. |
| 2006/0286070 A1 | 12/2006 | Hartmann et al. |
| 2006/0287263 A1 | 12/2006 | Davis et al. |
| 2007/0009482 A9 | 1/2007 | Krieg et al. |
| 2007/0010470 A9 | 1/2007 | Krieg et al. |
| 2007/0037767 A1 | 2/2007 | Bratzler et al. |
| 2007/0065467 A1 | 3/2007 | Krieg et al. |
| 2007/0066553 A1 | 3/2007 | Krieg et al. |
| 2007/0066554 A1 | 3/2007 | Krieg et al. |
| 2007/0078104 A1 | 4/2007 | Krieg et al. |
| 2007/0129320 A9 | 6/2007 | Davis et al. |
| 2007/0142315 A1 | 6/2007 | Forsbach et al. |
| 2007/0184465 A1 | 8/2007 | Wagner et al. |
| 2007/0190073 A1 | 8/2007 | Tuck et al. |
| 2007/0202128 A1 | 8/2007 | Krieg et al. |
| 2007/0202575 A1 | 8/2007 | Klinman et al. |
| 2007/0224210 A1 | 9/2007 | Krieg et al. |
| 2007/0232622 A1 | 10/2007 | Lipford et al. |
| 2007/0258994 A1 | 11/2007 | Van Nest et al. |
| 2007/0280929 A1 | 12/2007 | Hoerr et al. |
| 2008/0009455 A9 | 1/2008 | Krieg et al. |
| 2008/0026011 A1 | 1/2008 | Krieg et al. |
| 2008/0031936 A1 | 2/2008 | Krieg et al. |
| 2008/0045473 A1 | 2/2008 | Uhlmann et al. |
| 2008/0113929 A1 | 5/2008 | Lipford et al. |
| 2008/0152662 A1 | 6/2008 | Agrawal et al. |
| 2008/0226649 A1 | 9/2008 | Schetter et al. |
| 2009/0017021 A1 | 1/2009 | Davis et al. |

| | | | |
|---|---|---|---|
| 2009/0060927 A1 | 3/2009 | Wagner et al. | |
| 2009/0074851 A1 | 3/2009 | Bachmann et al. | |
| 2009/0155212 A1 | 6/2009 | Bratzler et al. | |
| 2009/0155307 A1 | 6/2009 | Davis et al. | |
| 2009/0191188 A1 | 7/2009 | Krieg et al. | |
| 2009/0202575 A1 | 8/2009 | Krieg et al. | |
| 2009/0214578 A1 | 8/2009 | Bauer | |
| 2009/0306177 A1 | 12/2009 | Uhlmann et al. | |
| 2009/0311277 A1 | 12/2009 | Krieg | |
| 2010/0125101 A1 | 5/2010 | Krieg et al. | |
| 2010/0166780 A1 | 7/2010 | Debelak et al. | |
| 2010/0183639 A1 | 7/2010 | Uhlmann et al. | |

FOREIGN PATENT DOCUMENTS

| | | |
|---|---|---|
| EP | 0 468 520 | 1/1992 |
| EP | 1 187 629 A2 | 10/2000 |
| EP | 1 550 458 A1 | 7/2005 |
| WO | WO 90/14822 A1 | 12/1990 |
| WO | WO 91/12811 A1 | 9/1991 |
| WO | WO 92/03456 | 3/1992 |
| WO | WO 94/08053 A1 | 4/1994 |
| WO | WO 94/19945 A | 9/1994 |
| WO | WO 95/03407 | 2/1995 |
| WO | WO 95/17507 A1 | 6/1995 |
| WO | WO 96/02555 A1 | 2/1996 |
| WO | WO 96/02560 A1 | 2/1996 |
| WO | WO 96/24380 | 8/1996 |
| WO | WO 96/40162 A1 | 12/1996 |
| WO | WO 97/28259 A1 | 8/1997 |
| WO | WO 97/30728 | 8/1997 |
| WO | WO 98/11211 A1 | 3/1998 |
| WO | WO 98/16247 A1 | 4/1998 |
| WO | WO 98/29430 | 7/1998 |
| WO | WO 98/32462 | 7/1998 |
| WO | WO 98/40100 A1 | 9/1998 |
| WO | WO 98/49288 A1 | 11/1998 |
| WO | WO 98/51278 A2 | 11/1998 |
| WO | WO 98/52962 A1 | 11/1998 |
| WO | WO 98/55495 A2 | 12/1998 |
| WO | WO 99/11275 A2 | 3/1999 |
| WO | WO 99/30686 | 6/1999 |
| WO | WO 99/33493 A1 | 6/1999 |
| WO | WO 99/33488 A2 | 7/1999 |
| WO | WO 99/33868 A2 | 7/1999 |
| WO | WO 99/62923 A2 | 9/1999 |
| WO | WO 99/52549 | 10/1999 |
| WO | WO 99/55743 A1 | 11/1999 |
| WO | WO 99/56755 A1 | 11/1999 |
| WO | WO 99/63975 A2 | 12/1999 |
| WO | WO 00/03683 A2 | 1/2000 |
| WO | WO 00/06588 A1 | 2/2000 |
| WO | WO 00/14217 A2 | 3/2000 |
| WO | WO 00/15256 A2 | 3/2000 |
| WO | WO 00/16804 A1 | 3/2000 |
| WO | WO 00/20039 A1 | 4/2000 |
| WO | WO 00/21556 A1 | 4/2000 |
| WO | WO 00/23105 A2 | 4/2000 |
| WO | WO 00/41463 A2 | 7/2000 |
| WO | WO 00/41720 A1 | 7/2000 |
| WO | WO 00/46365 A1 | 8/2000 |
| WO | WO 00/54803 A2 | 9/2000 |
| WO | WO 00/56359 A2 | 9/2000 |
| WO | WO 00/61151 A2 | 10/2000 |
| WO | WO 00/62787 A1 | 10/2000 |
| WO | WO 00/67023 A1 | 11/2000 |
| WO | WO 00/67787 A2 | 11/2000 |
| WO | WO 00/75304 A1 | 12/2000 |
| WO | WO 01/00231 A1 | 1/2001 |
| WO | WO 01/00232 A1 | 1/2001 |
| WO | WO 01/02007 A1 | 1/2001 |
| WO | WO 01/12223 A2 | 2/2001 |
| WO | WO 01/12804 A2 | 2/2001 |
| WO | WO 01/17550 A2 | 3/2001 |
| WO | WO 01/17551 A2 | 3/2001 |
| WO | WO 01/51083 A2 | 7/2001 |
| WO | WO 01/54719 A2 | 8/2001 |
| WO | WO 01/54720 A1 | 8/2001 |
| WO | WO 01/62909 A1 | 8/2001 |
| WO | WO 01/68077 A2 | 9/2001 |
| WO | WO 01/68078 A2 | 9/2001 |
| WO | WO 01/68103 A2 | 9/2001 |
| WO | WO 01/68116 A2 | 9/2001 |
| WO | WO 01/68117 A2 | 9/2001 |
| WO | WO 01/68143 A2 | 9/2001 |
| WO | WO 01/68144 A2 | 9/2001 |
| WO | WO 01/93902 A2 | 12/2001 |
| WO | WO 02/09748 A1 | 2/2002 |
| WO | WO 02/24225 | 3/2002 |
| WO | WO 02/26757 A2 | 4/2002 |
| WO | WO 02/28428 A2 | 4/2002 |
| WO | WO 02/036767 A3 | 5/2002 |
| WO | WO 02/097478 | 12/2002 |
| WO | WO 02/102307 A2 | 12/2002 |
| WO | WO 03/000232 A2 | 1/2003 |
| WO | WO 03/002065 A1 | 1/2003 |
| WO | WO 03/020889 A1 | 3/2003 |
| WO | WO 03/024481 A2 | 3/2003 |
| WO | WO 03/025119 A2 | 3/2003 |
| WO | WO 03/026688 A1 | 4/2003 |
| WO | WO 03/030656 | 4/2003 |
| WO | WO 03/030934 | 4/2003 |
| WO | WO 03/035836 A2 | 5/2003 |
| WO | WO 03/040308 A2 | 5/2003 |
| WO | WO 03/045428 A2 | 6/2003 |
| WO | WO 03/066649 A1 | 8/2003 |
| WO | WO 03/085110 A2 | 10/2003 |
| WO | WO 03/094963 | 11/2003 |
| WO | WO 03/100040 A1 | 12/2003 |
| WO | WO 03/101375 | 12/2003 |
| WO | WO 2004/004743 A1 | 1/2004 |
| WO | WO 2004/007743 A2 | 1/2004 |
| WO | WO 2004/012669 A2 | 2/2004 |
| WO | WO 2004/026888 A2 | 4/2004 |
| WO | WO 2004/094671 A2 | 11/2004 |
| WO | WO 2005/001055 A2 | 1/2005 |
| WO | WO 2005/004907 A1 | 1/2005 |
| WO | WO 2005/004910 A2 | 1/2005 |
| WO | WO 2005/009355 A2 | 2/2005 |
| WO | WO 2005/013891 A2 | 2/2005 |
| WO | WO 2005/023289 A1 | 3/2005 |
| WO | WO 2005/059517 A2 | 6/2005 |
| WO | WO 2005/072290 A2 | 8/2005 |
| WO | WO 2005/079419 A2 | 9/2005 |
| WO | WO 2006/080946 A2 | 8/2006 |
| WO | WO 2007/031877 A2 | 3/2007 |
| WO | WO 2007/038720 A2 | 4/2007 |
| WO | WO 2008/030455 A2 | 3/2008 |
| WO | WO 2008/033432 A2 | 3/2008 |
| WO | WO 2008/039538 A2 | 4/2008 |
| WO | WO 2008/068638 | 6/2008 |
| WO | WO 2008/139262 A2 | 11/2008 |

OTHER PUBLICATIONS

Agrawal et al., Absorption, tissue distribution and in vivo stability in rats of a hybrid antisense oligonucleotide following oral administration. Biochem Pharmacol. Aug. 8, 1995;50(4):571-6.

Agrawal et al., In vivo pharmacokinetics of phosphorothioate oligonucleotides containing contiguous guanosines. Antisense Nucleic Acid Drug Dev. Jun. 1997;7(3):245-9.

Agrawal et al., Novel immunomodulatory oligonucleotides prevent development of allergic airway inflammation and airway hyper-responsiveness in asthma. Int Immunopharmacol. Jan. 2004;4(1):127-38.

Agrawal et al., Antisense therapeutics: is it as simple as complementary base recognition? Mol Med Today. Feb. 2000;6(2):72-81.

Agrawal et al., Pharmacokinetics, biodistribution, and stability of oligodeoxynucleotide phosphorothioates in mice. Proc Natl Acad Sci U S A. Sep. 1, 1991;88(17):7595-9.

Agrawal et al., Medicinal chemistry and therapeutic potential of CpG DNA. Trends Mol Med. Mar. 2002;8(3):114-21.

Agrawal et al., Pharmacokinetics of antisense oligonucleotides. Clin Pharmacokinet. Jan. 1995;28(1):7-16.

Ammerpohl et al., Complex protein binding to the mouse M-lysozyme gene downstream enhancer involves single-stranded DNA binding. Gene. Oct. 24, 1997;200(1-2):75-84.

An et al., Isoforms of the EP3 subtype of human prostaglandin E2 receptor transduce both intracellular calcium and cAMP signals. Biochemistry. Dec. 6, 1994;33(48):14496-502.

Anderson et al., Selective inhibition of cyclooxygenase (COX)-2 reverses inflammation and expression of COX-2 and interleukin 6 in rat adjuvant arthritis. J Clin Invest. Jun. 1, 1996;97(11):2672-9.

Anitescu et al., Interleukin-10 functions in vitro and in vivo to inhibit bacterial DNA-induced secretion of interleukin-12. J Interferon Cytokine Res. Dec. 1997;17(12):781-8.

Ballas et al., Divergent therapeutic and immunologic effects of oligodeoxynucleotides with distinct CpG motifs. J Immunol. Nov. 1, 2001;167(9):4878-86.

Bochner et al., Advances in mechanisms of allergy. J Allergy Clin Immunol. May 2004;113(5):868-75.

Bohle et al., Oligodeoxynucleotides containing CpG motifs induce IL-12, IL-18 and IFN-gamma production in cells from allergic individuals and inhibit IgE synthesis in vitro. Eur J Immunol. Jul. 1999;29(7):2344-53.

Broide et al., Immunostimulatory DNA sequences inhibit IL-5, eosinophilic inflammation, and airway hyperresponsiveness in mice. J Immunol. Dec. 15, 1998;161(12):7054-62.

Broide et al., Modulation of asthmatic response by immunostimulatory DNA sequences. Springer Immunopath. 2000;22(1-2):117-24.

Broide et al., DNA-Based immunization for asthma. Int Arch Allergy Immunol. Feb.-Apr. 1999;118(2-4):453-6.

Carson et al., Oligonucleotide adjuvants for T helper 1 (Th1)-specific vaccination. J Exp Med. Nov. 17, 1997;186(10):1621-2.

Chace et al., Bacterial DNA-induced NK cell IFN-gamma production is dependent on macrophage secretion of IL-12. Clin Immunol Immunopathol. Aug. 1997;84(2):185-93.

Chu et al., CpG oligodeoxynucleotides down-regulate macrophage class II MHC antigen processing. J Immunol. Aug. 1, 1999;163(3):1188-94.

Crooke et al., Phosphorothioate Oligonucleotides. Therapeut Apps. 1995;ch5:63-84.

Crooke et al., Progress in antisense oligonucleotide therapeutics. Annu Rev Pharmacol Toxicol. 1996;36:107-29.

Dalpke et al., Phosphodiester CpG oligonucleotides as adjuvants: polyguanosine runs enhance cellular uptake and improve immunostimulative activity of phosphodiester CpG oligonucleotides in vitro and in vivo. Immunology. May 2002;106(1):102-12.

Filion et al., Major limitations in the use of cationic liposomes for DNA delivery. Int. J Pharmaceut. 1998; 162:159-70.

Gomis et al., Protection of chickens against *Escherichia coli* infections by DNA containing CpG motifs. Infect Immun. Feb. 2003;71(2):857-63.

Grossmann et al., Avoiding tolerance against prostatic antigens with subdominant peptide epitopes. J Immunother. May-Jun. 2001;24(3):237-41.

Gursel et al., Sterically stabilized cationic liposomes improve the uptake and immunostimulatory activity of CpG oligonucleotides. J Immunol. Sep. 15, 2001;167(6):3324-8.

Gursel et al., Differential and competitive activation of human immune cells by distinct classes of CpG oligodeoxynucleotide. J Leukoc Biol. May 2002;71(5):813-20. Abstract Only.

Hartmann et al., CpG DNA and LPS induce distinct patterns of activation in human monocytes. Gene Ther. May 1999;6(5):893-903.

Hartmann et al., Spontaneous and cationic lipid-mediated uptake of antisense oligonucleotides in human monocytes and lymphocytes. J Pharmacol Exp Ther. May 1998;285(2):920-8.

Ioannou et al., The immunogenicity and protective efficacy of bovine herpesvirus 1 glycoprotein D plus Emulsigen are increased by formulation with CpG oligodeoxynucleotides. J Virol. Sep. 2002;76(18):9002-10.

Jain et al., CpG-oligodeoxynucleotides inhibit airway remodeling in a murine model of chronic asthma. J Allergy Clin Immunol. Dec. 2002;110(6):867-72.

Jain et al., CpG DNA and immunotherapy of allergic airway diseases. Clin Exp Allergy. Oct. 2003;33(10):1330-5.

Jain et al., CpG DNA: immunomodulation and remodelling of the asthmatic airway. Expert Opin Biol Ther. Sep. 2004;4(9):1533-40.

Kandimalla et al., A dinucleotide motif in oligonucleotides shows potent immunomodulatory activity and overrides species-specific recognition observed with CpG motif. Proc Natl Acad Sci U S A. Nov. 25, 2003;100(24):14303-8.

Kandimalla et al., Towards optimal design of second-generation immunomodulatory oligonucleotides. Curr Opin Mol Ther. Apr. 2002;4(2):122-9.

Kandimalla et al., Divergent synthetic nucleotide motif recognition pattern: design and development of potent immunomodulatory oligodeoxyribonucleotide agents with distinct cytokine induction profiles. Nucleic Acids Res. May 1, 2003;31(9):2393-400.

Kandimalla et al., Effect of chemical modifications of cytosine and guanine in a CpG-motif of oligonucleotides: structure-immunostimulatory activity relationships. Bioorg Med Chem. Mar. 2001;9(3):807-13.

Kataoka et al., Immunotherapeutic potential in guinea-pig tumor model of deoxyribonucleic acid from *Mycobacterium bovis* BCG complexed with poly-L-lysine and carboxymethylcellulose. Jpn J Med Sci Biol. Oct. 1990;43(5):171-82.

Kitagaki et al., Immunomodulatory effects of CpG oligodeoxynucleotides on established th2 responses. Clin Diagn Lab Immunol. Nov. 2002;9(6):1260-9.

Kline et al., Modulation of airway inflammation by CpG oligodeoxynucleotides in a murine model of asthma. J Immunol. Mar. 15, 1998;160(6):2555-9.

Kline et al., Treatment of established asthma in a murine model using CpG oligodeoxynucleotides. Am J Physiol Lung Cell Mol Physiol. Jul. 2002;283(1):L170-9.

Kline et al., DNA therapy for asthma. Curr Opin Allergy Clin Immunol. Feb. 2002;2(1):69-73.

Kline et al., Effects of CpG DNA on Th1/Th2 balance in asthma. Curr Top Microbiol Immunol. 2000;247:211-25.

Kline et al., CpG oligodeoxynucleotides do not require TH1 cytokines to prevent eosinophilic airway inflammation in a murine model of asthma. J Allergy Clin Immunol. Dec. 1999;104(6):1258-64.

Klinman et al., Therapeutic applications of CpG-containing oligodeoxynucleotides. Antisense Nucleic Acid Drug Dev. Apr. 1998;8(2):181-4.

Klinman et al., Immunotherapeutic applications of CpG-containing oligodeoxynucleotides. Drug News Perspect. Jun. 2000;13(5):289-96.

Klinman et al., CpG motifs as immune adjuvants. Vaccine. Jan. 1999;17(1):19-25.

Krieg et al., American College of Rheumatology 58th National Scientific Meeting. Minneapolis, Minnesota, Oct. 22, 1994. Abstracts. Arthritis Rheum. Sep. 1994;37(9 Suppl).

Krieg et al., Direct immunologic activities of CpG DNA and implications for gene therapy. J Gene Med. Jan.-Feb. 1999;1(1):56-63.

Krieg et al., Applictions of immune stimulatory CpG DNA for antigen-specific and antigen-nonspecific cancer immunotherapy. Eur J Canc. Oct. 1999; 35/Supp14:S10. Abstract #14.

Krieg et al., Causing a commotion in the blood: immunotherapy progresses from bacteria to bacterial Dna. Immunol Today. Oct. 2000;21(10):521-6.

Krieg et al., Chapter 8: Immune Stimulation by Oligonucleotides. in Antisense Research and Application. Crooke, editor. 1998; 243-62.

Krieg et al., A role for endogenous retroviral sequences in the regulation of lymphocyte activation. J Immunol. Oct. 15, 1989;143(8):2448-51.

Krieg et al., P-chirality-dependent immune activation by phosphorothioate CpG oligodeoxynucleotides. Oligonucleotides. 2003;13(6):491-9.

Krieg et al., Chapter 17:Immune stimulation by oligonucleotides. In Antisense Drug Tech. 2001;1394:471-515.

Krieg et al., Mechanisms and applications of immune stimulatory CpG oligodeoxynucleotides. Biochim Biophys Acta. Dec. 10, 1999;1489(1):107-16.

Krieg et al., The CpG motif: Implications for clinical immunology. BioDrugs. Nov. 1, 1998;10(5):341-6.

Krieg et al., Mechanism of action of CpG DNA. Curr Top Microbiol Immunol. 2000;247:1-21.

Krieg et al., CpG DNA: a novel immunomodulator. Trends Microbiol. Feb. 1999;7(2):64-5.

Krieg, Signal transduction induced by immunostimulatory CpG DNA. Springer Semin Immunopathol. 2000;22(1-2):97-105.

Krieg et al., How to exclude immunostimulatory and other nonantisense effects of antisense oligonucleotides. Manual of Antisense. 1999:79-89.

Krieg et al., Unmethylated CpG DNA protects mice from lethal listeria monocytogenes challenge. Vaccines. 1997; 97:77-9.

Krieg et al., Infection. In McGraw Hill Book. 1996: 242-3.

Krieg et al., Lymphocyte activation by CpG dinucleotide motifs in prokaryotic DNA. Trends Microbiol. Feb. 1996;4(2):73-6.

Krug et al., Identification of CpG oligonucleotide sequences with high induction of IFNalpha/beta in plasmacytoid dendritic cells. Eur J Immunol. Jul. 2001;31(7):2154-63.

Krug et al., Toll-like receptor expression reveals CpG DNA as a unique microbial stimulus for plasmacytoid dendritic cells which synergizes with CD40 ligand to induce high amounts of Il-12. Eur J Immunol. Oct. 2001;31(10):3026-37.

Kuramoto et al., Induction of T-cell-mediated immunity against MethA fibrosarcoma by intratumoral injections of a bacillus Calmette-Guerin nucleic acid fraction. Cancer Immunol Immunother. 1992;34(5):283-8.

Liu et al., CpG directly induces T-bet expression and inhibits IgG1 and IgE switching in B cells. Nat Immunol. Jul. 2003;4(7):687-93.

MacFarlane et al., Unmethylated CpG-containing oligodeoxynucleotides inhibit apoptosis in WEHI 231 B lymphocytes induced by several agents: evidence for blockade of apoptosis at a distal signalling step. Immunology. Aug. 1997;91(4):586-93.

Marshall et al., Immunostimulatory sequence DNA linked to the Amb a 1 allergen promotes T(H)1 cytokine expression while downregulating T(H)2 cytokine expression in PBMCs from human patients with ragweed allergy. J Allergy Clin Immunol. Aug. 2001;108(2):191-7.

Martin-Orozco et al., Enhancement of antigen-presenting cell surface molecules involved in cognate interactions by immunostimulatory DNA sequences. Int Immunol. Jul. 1999;11(7):1111-8.

Messina et al., The influence of DNA structure on the in vitro stimulation of murine lymphocytes by natural and synthetic polynucleotide antigens. Cell Immunol. Mar. 1993;147(1):148-57.

Muhlhauser et al., VEGF165 expressed by a replication-deficient recombinant adenovirus vector induces angiogenesis in vivo. Circ Res. Dec. 1995;77(6):1077-86.

Ochiai et al., Studies on lymphocyte subsets of regional lymph nodes after endoscopic injection of biological response modifiers in gastric cancer patients. Int J Immunotherapy. 1986;11(4):259-65.

Parronchi et al., Phosphorothioate oligodeoxynucleotides promote the in vitro development of human allergen-specific CD4+ T cells into Th1 effectors. J Immunol. Dec. 1, 1999;163(11):5946-53.

Pisetsky et al., Immunological properties of bacterial DNA. Ann NY Acad Sci. Nov. 27, 1995;772:152-63.

Pisetsky et al., Influence of backbone chemistry on immune activation by synthetic oligonucleotides. Biochem Pharmacol. Dec. 15, 1999;58(12):1981-8.

Pisetsky et al., Immune activation by bacterial DNA: a new genetic code. Immunity. Oct. 1996;5(4):303-10.

Pisetsky et al., the influence of base sequence on the immunological properties of defined oligonucleotides. Immunopharmacology. Nov. 1998;40(3):199-208.

Polanczyk et al., Immunostimulatory effects of DNA and CpG motifs. Cent Eur J of Immunol. 2000;25(3):160-6.

Rankin et al., CpG motif identification for veterinary and laboratory species demonstrates that sequence recognition is highly conserved. Antisense Nucleic Acid Drug Dev. Oct. 2001;11(5):333-40.

Rankin et al., CpG-containing oligodeoxynucleotides augment and switch the immune responses of cattle to bovine herpesvirus-1 glycoprotein D. Vaccine. Jul. 26, 2002;20(23-24):3014-22.

Raz et al., Potential role of immunostimulatory DNA sequences (ISS) in genetic immunization and autoimmunity. ACR Poster Session C: Cytokines and Inflammatory Mediators. Oct. 20, 1996; Abstract No. 615.

Redecke et al., Cutting edge: activation of Toll-like receptor 2 induces a Th2 immune response and promotes experimental asthma. J Immunol. Mar. 1, 2004;172(5):2739-43.

Rothenfusser et al., Recent advances in immunostimulatory CpG oligonucleotides. Curr Opin Mol Ther. Apr. 2003;5(2):98-106.

Sandler et al., CpG oligonucleotides enhance the tumor antigen-specific immune response of a granulocyte macrophage colony-stimulating factor-based vaccine strategy in neuroblastoma. Cancer Res. Jan. 15, 2003;63(2):394-9.

Sandrasagra et al., Discovery and development of respirable antisense therapeutics for asthma. Antisense Nucleic Acid Drug Dev. Jun. 2002;12(3):177-81.

Sands et al., Biodistribution and metabolism of internally 3H-labeled oligonucleotides. I. Comparison of a phosphodiester and a phosphorothioate. Mol Pharmacol. May 1994;45(5):932-43.

Singh et al., Cationic microparticles are an effective delivery system for immune stimulatory CpG DNA. Pharm Res. Oct. 2001;18(10):1476-9.

Sparwasser et al., Bacterial DNA causes septic shock. Nature. Mar. 27, 1997;386(6623):336-7.

Sparwasser et al., Immunostimulatory CpG-oligodeoxynucleotides cause extramedullary murine hemopoiesis. J Immunol. Feb. 15, 1994;162(4):2368-74.

Spiegelberg et al., DNA-based approaches to the treatment of allergies. Curr Opin Mol Ther. Feb. 2002;4(1):64-71.

Stein et al., Problems in interpretation of data derived from in vitro and in vivo use of antisense oligonucleotides. Antisense Res Dev. 1994 Summer;4(2):67-9.

Stein et al., Physicochemical properties of phosphorothioate oligonucleotides. Nucleic Acids Res. Apr. 25, 1998;16(8):3209-21.

Stein et al., Non-antisense effects of oligodeoxynucleotides. Antisense Technology. 1997; ch11: 241-64.

Stein et al., Antisense oligonucleotides as therapeutic agents—is the bullet really magical? Science. Aug. 20, 1993;261(5124):1004-12.

Stunz et al., Inhibitory oligonucleotides specifically block effects of stimulatory CpG oligonucleotides in B cells. Eur J lmmunol. May 2002;32(5):1212-22.

Sur et al., Long term prevention of allergic lung inflammation in a mouse model of asthma by CpG oligodeoxynucleotides. J Immunol. May 15, 1999;162(10):6284-93.

Tanaka et al., An antisense oligonucleotide complementary to a sequence in I gamma 2b increases gamma 2b germline transcripts, stimulates B cell DNA synthesis, and inhibits immunoglobulin secretion. J Exp Med. Feb. 1, 1992;175(2):597-607.

Uhlmann et al., Recent advances in the development of immunostimulatory oligonucleotides. Curr Opin Drug Discov Devel. Mar. 2003;6(2):204-17.

Van Uden et al., Immunostimulatory DNA and applications to allergic disease. J Allergy Clin Immunol. Nov. 1999;104(5):902-10.

Verthelyi et al., Immunoregulatory activity of CpG oligonucleotides in humans and nonhuman primates. Clin Immunol. Oct. 2003;109(1):64-71.

Verthelyi et al., Human peripheral blood cells differentially recognize and respond to two distinct Cpg motifs. J Immunol. Feb. 15, 2001;166(4):2372-7.

Vollmer et al., Highly immunostimulatory CpG-free oligodeoxynucleotides for activation of human leukocytes. Antisense Nucleic Acid Drug Dev. Jun. 2002;12(3):165-75.

Vollmer et al., Immunopharmacology of CpG oligodeoxynucleotides and ribavirin. Antimicrob Agents Chemother. Jun. 2004;48(6):2314-7.

Vollmer et al., Characterization of three CpG oligodeoxynucleotide classes with distinct immunostimulatory activities. Eur J Immunol. Jan. 2004;34(1):251-62.

Vollmer et al, Modulation of CpG oligodeoxynucleotide-inediated immune stimulation by locked nucleic acid (LNA). Oligonucleotides. 2004 Spring;14(1):23-31.

Wang et al., Synergy between CpG- or non-CpG DNA and specific antigen for B cell activation. Int Immunol. Feb. 2003;15(2):223-31.

Whitesell et al., Stability, clearance, and disposition of intraventricularly administered oligodeoxynucleotides: implications for therapeutic application within the central nervous system. Proc Natl Acad Sci U S A. May 15, 1993;90(10):4665-9.

Yamamoto et al., [Commemorative lecture of receiving Imamura Memorial Prize. II. Mode of action of oligonucleotide fraction extracted from Mycobacterium bovis BCG] Kekkaku. Sep. 1994;69(9):571-4.

Yamamoto et al., Synthetic oligonucleotides with certain palindromes stimulate interferon production of human peripheral blood lymphocytes in vitro. Jpn J Cancer Res. Aug. 1994;85(8):7759.

Yi et al., CpG DNA rescue of murine B lymphoma cells from anti-IgM-induced growth arrest and programmed cell death is associated with increased expression of c-myc and bcl-xL. J Immunol. Dec. 1, 1996;157(11):4918-25.

Yu et al., Accessible 5'-end of CpG-containing phosphorothioate oligodeoxynucleotides is essential for immunostimulatory activity. Bioorg Med Chem Lett. Dec. 4, 2000;10(23):2585-8.

Zhao et al., Pattern and kinetics of cytokine production following administration of phosphorothioate oligonucleotides in mice. Antisense Nucleic Acid Drug Dev. Oct. 1997;7(5):495-502.

Zhao et al., Modulation of oligonucleotide-induced immune stimulation by cyclodextrin analogs. Biochem Pharmacol. Nov. 22, 1996;52(10):1537-44.

Zhao et al., Effect of different chemically modified oligodeoxynucleotides on immune stimulation. Biochem Pharmacol. Jan. 26, 1996;51(2):173-82.

Agrawal et al., "Antisense oligonucleotides: towards clinical trials", *Trends in Biotechnology*, 14: 376-387, 1996.

Anderson et al., "Induction of determinant spreading and of Th1 responses by in vitro stimulation with HER-2 peptides", *Cancer Immunology Immunotherapy*, 49(9): 459-68, 2000.

Anderson et al., "TH2 and 'TH2-like' cells in allergy and asthma: pharmacological perspectives", *Trends in Pharmacological Science*, 15: 324-332, 1994.

Askew et al., "CpG DNA induces maturation of dendritic cells with distinct effects on nascent and recycling MHC-II antigen-processing mechanisms", *Journal of Immunology*, 165: 6889-95, 2000.

Ballas et al., "Induction of NK activity in murine and human cells by CpG motifs in oligodeoxynucleotides and bacterial DNA", J Immunol. Sep. 1, 1996;157(5):1840-5.

Bates et al., "Antiproliferative activity of G-rich oligonucleotides correlates with protein binding", *Journal of Biological Chemistry*, 274: 26369-77, 1999.

Bayever et al., "Systemic administration of a phosphorothioate oligonucleotide with a sequence complementary to p53 for acute myelogenous leukemia and myelodysplastic syndrome: initial results of a phase I trial", *Antisense Research & Development*, 3: 383-390, 1993.

Benimetskaya et al., "Formation of a G-tetrad and higher order structures correlates with biological activity of the ReIA (NF-kappaB p65) 'antisense' oligodeoxynucleotide", *Nucleic Acid Research*, 25(3): 2648-56, 1997.

Bishop et al., "Intramolecular G-quartet motifs confer nuclease resistance to a potent anti-HIV oligonucleotide", *Journal of Biological Chemistry*, 271: 5698-5703, 1996.

Blaxter et al., "Genes expressed in Brugia malayi infective third stage larvae", *Molecular and Biochemical Parasitology*, 77: 77-93, 1996.

Boggs et al., "Characterization and modulation of immune stimulation by modified oligonucleotides", *Antisense Nucleic Acid Drug Development*, 7(5): 461-71,1997.

Branda et al., "Immune stimulation by an antisense oligomer complementary to the rev gene of HIV-1", *Biochemical Pharmacology*, 45(10): 2037-2043, 1993.

Branda et al., "Amplification of antibody production by phosphorothioate oligodeoxynucleotides", *Journal of Laboratory Clinical Medicine*, 128(3): 329-38, 1996.

Brazolot-Millan et al., "CpG DNA can induce strong Th1 humoral and cell-mediated immune responses against hepatitis B surface antigen in young mice", *Proceedings of the National Academy of Science USA*, 95: 15553-15558, 1998.

Broide et al., "DNA-Based immunization for asthma", *International Archives of Allergy and Immunology*, 118: 453-456, 1999.

Brossart et al., "Induction of cytotoxic T-lymphocyte responses in vivo after vaccinations with peptide-pulsed dendritic cells", *Blood*, 96(9): 3102-8, 2000.

Brunner et al., "Enhanced dendritic cell maturation by TNF-alpha or cytidine-phosphate-guanosine DNA drives T cell activation in vitro and therapeutic anti-tumor immune responses in vivo", *Journal of Immunology*, 165: 6278-6286, 2000.

Burgess et al., "The antiproliferative activity of c-myb and c-myc antisense oligonucleotides in smooth muscle cells is caused by a nonantisense mechanism", *Proceedings of the National Academy of Science USA*, 92(9): 4051-5, 1995.

Cavacini et al., "Evidence of determinant spreading in the antibody responses to prostate cell surface antigens in patients immunized with prostate-specific antigen", *Clinical Cancer Research*, 8(2): 368-73, 2002.

Choi et al., "The level of protection against rotavirus shedding in mice following immunization with a chimeric VP6 protein is dependent on the route and the coadministered adjuvant", *Vaccine*, 20(13-14): 1733-40, 2002.

Chu et al., "CpG oligodeoxynucleotides act as adjuvants that switch on T helper I (Th1) immunity", *Journal of Experimental Medicine*, 186(10): 1623-31, 1997.

Constant et al., "Induction of Th 1 and Th2 CD4+ T cell responses: the alternative approaches", Annual Reviews in Immunology, 15: 297-322, 1997.

Constant et al., "Stimulation of human gamma delta T cells by nonpeptidic mycobacterial ligands", Science, 264: 267-70, 1994.

Cossum et al., "Pharmacokinetics of a 14C-labeled phosphorothioate oligonucleotide, Isis 2105, after intradermal administration to rats", *Journal of Pharmacological Experimental Theory*, 269(1): 89-94, 1994.

Cowdery et al., "Bacterial DNA induces NK cells to produce IFN-gamma in vivo and increases the toxicity of lipopolysaccharides", Journal of Immunology, 156(12): 4570-5, 1996.

Cowsert et al., "In vitro evaluation of phosphorothioate oligonucleotides targeted to the E2 mRNA of papillomavirus: potential treatment for genital warts", *Antimicrobial Agents in Chemotherapy*, 37: 171-77, 1993.

Daheshia et al., "Immune induction and modulation by topical ocular administration of plasmid DNA encoding antigens and cytokines", *Vaccine*, 16(11-12): 1103-1110, 1998.

Dapic et al., *Proceedings of AACR*, pp. 42 Mar. 2001.

Davis et al., "CpG DNA is a potent enhancer of specific immunity in mice immunized with recombinant hepatitis B surface antigen", *Journal of Immunology*, 160(2): 870-6, 1998.

Davis et al., "CpG DNA overcomes hyporesponsiveness to hepatitis B vaccine in orangutans", *Vaccine*, 18; 1920-1924, 2000.

Davis et al., "Plasmid DNA expression systems for the purpose of immunization", *Current Opinions Biotechnology*, 8(5): 635-46, 1997.

Davis et al., "Use of CpG DNA for enhancing specific immune responses", *Current Topics in Microbiology Immunology*, 247: 171-83, 2000.

Deml et al., "Immunostimulatory CpG motifs trigger a T helper-I immune response to human immunodeficiency virus type-1 (HIV-1) gp160 envelope proteins", *Clinical Chemistry Laboratory Medicine*, 37: 199-204 1999.

Diamantstein et al., "Specific binding of poly(I)-poly(C) to the membrane of murine B lymphocyte subsets", *European Journal of Immunology*, 8: 896, 1978.

Disis et al., "Generation of immunity to the HER-2/neu oncogenic protein in patients with breast and ovarian cancer using a peptide-based vaccine", *Clinical Cancer Research*, 5(6): 1289-97, 1999.

Disis et al., "Generation of T-cell immunity to the HER-2/neu protein after active immunization with HER-2/neu peptide-based vaccines", *Journal of Clinical Oncology*, 20(11): 2624-32, 2002.

Dumais et al., "Mucosal immunization with inactivated human immunodeficiency virus plus CpG oligodeoxynucleotides induces genital immune responses and protection against intravaginal challenge", *Journal of Infection and Disease*, 186(8): 1098-105, 2002.

Elkins et al., "Bacterial DNA containing CpG motifs stimulates lymphocyte-dependent protection of mice against lethal infection with intracellular bacteria", *Journal of Immunology*, 162: 2291-2298, 1999.

El-Shami et al., "MHC class I-restricted epitope spreading in the context of tumor rejection following vaccination with a single immunodominant CTL epitope", *European Journal of Immunology* .29(10): 3295-301, 2002.

Ewel et al., "Polyinosinic-polycytidylic acid complexed with poly-L-lysine and carboxymethylcellulose in combination with interleukin 2 in patients with cancer: clinical and immunological effects", *Cancer Research*, 52(11):3005-10, 1992.

Freidag et al., "CpG oligodeoxynucleotides and interleukin-12 improve the efficacy of *Mycobacterium bovis* BCG vaccination in mice challenged with *M. tuberculosis*", *Infection and Immunity*, 68: 2948-2953, 2000.

Gallichan et al., "Intranasal immunization with CpG oligodeoxynucleotides as an adjuvant dramatically increases IgA and protection against herpes simplex virus-2 in the genital tract", *The Journal of Immunology*, 166: 3451-3457, 2001.

Hadden et al., "Immunostimulants", *Trends in Pharmacological Science*, 14: 169-174, 1993.

Hahm et al., "Efficacy of polyadenylic.polyuridylic acid in the treatment of chronic active Hepatitis B", *Int J Immunopharmac*, 16(3): 217-25, 1994.

Halpern et al., "Bacterial DNA induces murine interferon-gamma production by stimulation of interleukin-12 and tumor necrosis factor-alpha", *Cell Immunology*, 167(1): 72-8, 1996.

Harrington et al., "Adjuvant effects of low doses of a nuclease-resistant derivative of polyinosinic acid . polycytidylic acid on antibody responses of monkeys to inactivated Venezuelan equine encephalomyelitis virus vaccine", *Infection and Immunity*, 24: 160, 1979.

Hartmann et al., "CpG DNA and LPS induce distinct patterns of activation in human monocytes", *Gene Therapy*, 6: 893-903, 1999.

Hartmann et al., "Mechanism and function of a newly identified CpG DNA motif in human primary B cells", *Journal of Immunology*, 164: 944, 2000.

Hartmann et al., "Specific suppression of human tumor necrosis factor-alpha synthesis by antisense oligodeoxynucleotides", *Antisense Nucleic Acid Drug Development*, 6: 291, 1996.

Hartmann et al., "Delineation of a CpG phosphorothioate oligodeoxynucleotide for activating primate immune responses in vitro and in vivo", *Journal of Immunology*, 164: 1617, 2000.

Hartmann et al., "CpG DNA: a potent signal for growth, activation, and maturation of human dendritic cells", *Proceedings of the National Academy of Science USA*, 96: 9305-9310, 1999.

Hayashi et al., "Enhancement of innate immunity against *Mycobacterium avium* infection by immunostimulatory DNA is mediated by indoleamine 2,3-dioxygenase", *Infection and Immunity*, 69: 6156-6164, 2001.

Hinkula et al., "Recognition of prominent viral epitopes induced by immunization with human immunodeficiency virus type I regulatory genes", *Journal of Virology*, 71(7): 5528-39, 1997.

Hopkin et al., *BioMedNet*, Issue 57, Jun. 25, 1999.

Huang et al., "Induction and regulation of Th1-inducing cytokines by bacterial DNA, lipopolysaccharide, and heat-inactivated bacteria", *Infection and Immunity*, 67(12): 6257-6263, 1999.

Hughes et al., *Antisense Research Development*, 4: 211-15, 1994.

Hung et al., "Improving vaccine potency through intercellular spreading and enhanced MHC class I presentation of antigen", *Journal of Immunology*, 166(9): 5733-40, 2001.

Iho et al., "Oligodeoxynucleotides containing palindrome sequences with internal 5'-CpG-3' act directly on human NK and activated T cells to induce IFN-gamma production in vitro", *Journal of Immunology*, 163: 3642, 1999.

Ishikawa et al., "IFN induction and associated changes in splenic leukocyte distribution", *Journal of Immunology*, 150(9): 3713-27, 1993.

Iversen et al., "Pharmacokinetics of an antisense phosphorothioate oligodeoxynucleotide against rev from human immunodeficiency virus type 1 in the adult male rat following single injections and continuous infusion", *Antisense Research and Development*, 4: 43-52, 1994.

Jakob et al., "Activation of cutaneous dendritic cells by CpG-containing oligodeoxynucleotides: a role for dendritic cells in the augmentation of Th1 responses by immunostimulatory DNA", *Journal of Immunology*, 161(6): 3042-9, 1998.

Jakob et al., "Bacterial DNA and CpG-containing oligodeoxynucleotides activate cutaneous dendritic cells and induce IL-12 production: implications for the augmentation of Th1 responses", *International Archives of Allergy Immunology*, 118(2-4): 457-61, 1999.

Johnson et al., *Immunopharmacology, Infection, and Disease*, 291-301, 1987.

Jones et al., "Synthetic oligodeoxynucleotides containing CpG motifs enhance immunogenicity of a peptide malaria vaccine in Aotus monkeys", *Vaccine*, 17: 3065-3071, 1999.

Juffermans et al., "CpG oligodeoxynucleotides enhance host defense during murine tuberculosis", *Infection and Immunity*, 70: 147-152, 2002.

Kandimalla et al., "A dinucleotide motif in oligonucleotides shows potent immunomodulatory activity and overrides species-specific recognition observed with CpG motif", *Proceedings of the National Academy of Science*, 100(24): 14303-14308, 2003.

Kataoka et al., "Antitumor activity of synthetic oligonucleotides with sequences from cDNA encoding proteins of *Mycobacterium bovis* BCG", *Japan Journal of Cancer Research*, 83: 244-247, 1992.

Kern et al., "Herpesvirus hominis infection in newborn mice: treatment with interferon inducer polyinosinic-polycytidylic acid", *Antimicrobial Agent Chemotherapy*, 7: 793, 1975.

Kimura et al., "Binding of oligoguanylate to scavenger receptors is required for oligonucleotides to augment NK cell activity and induce IFN", *Journal of Biochemistry*, 116(5): 991-994, 1994.

Kline et al., *Journal of Investigative Medicine*, 44(7): 380A, 1996.

Kline et al., *Journal of Investigative Medicine*, 45(3): 282A, 1997.

Kline et al., *Journal of Investigative Medicine*, 45(7): 298A, 1997.

Kline et al., "CpG oligodeoxynucleotides do not require TH1 cytokines to prevent eosinophilic airway inflammation in a murine model of asthma", *Journal of Allergy and Clinical Immunology*, 1258-64, 1999.

Klinman et al., "Immune recognition of foreign DNA: a cure for bioterrorism?", *Immunity*, 11: 123-129, 1999.

Klinman et al., "Repeated administration of synthetic oligodeoxynucleotides expressing CpG motifs provides long-term protection against bacterial infection", *Infection and Immunity*, 67: 5658-5663, 1999.

Klinman et al., "Activation of the innate immune system by CpG oligodeoxynucleotides: immnunoprotective activity and safety", *Springer Seminars in Immunopathology*, 22: 173-183, 2000.

Klinman et al., "Contribution of CpG motifs to the immunogenicity of DNA vaccines", *Journal of Immunology*, 158(8): 3635-9, 1997.

Klinman et al., "CpG motifs present in bacteria DNA rapidly induce lymphocytes to secrete interleukin 6, interleukin 12, and interferon gamma", *Proceedings of the National Academy of Science USA*, 93(7): 2879-83, 1996.

Kou et al., *Arerugi*, 43: 482, 1994. Abstract only.

Kovarik et al., "Adjuvant effects of CpG oligodeoxynucleotides on responses against T-independent type 2 antigens", *Immunology*, 102(1): 67-76, 2001.

Kovarik et al., *The Journal of Immunology*, 162: 1611-1617, 1999.

Kranzer et al. "CpG oligodeoxynucleotides can circumvent the Th2 polarization of neonatal responses to vaccines but may fail to fully redirect Th2 responses established by neonatal priming", *Immunology*, 99: 170, 2000.

Krieg et al., "CpG motifs in bacterial DNA and their immune effects", *Annual Reviews in Immunology*, 20: 709, 2002.

Krieg et al., "Immune effects and therapeutic applications of CpG motifs in bacterial DNA", *Immunopharmacology*, 48: 303-305, 2000.

Krieg et al., "Oligodeoxynucleotide modifications determine the magnitude of B cell stimulation by CpG motifs", *Antisense Nucleic Acid Drug Development*, 6(2): 133-9, 1996.

Krieg et al., "Phosphorothioate oligodeoxynucleotides: antisense or anti-protein?", *Antisense Research and Development*, 5: 241, 1995.

Meg et al., *Applied Antisense Oligonucleotide Technology*, 431-448, 1998.

Krieg et al., "CpG DNA: a pathogenic factor in systemic lupus erythematosus?", *Journal of Clinical Immunology*, 15(6): 284-292, 1995.

Krieg et al., "CpG motifs in bacterial Dna trigger direct B-cell activation", Nature, 374: 546-9, 1995.

Krieg et al., "Modification of antisense phosphodiester oligodeoxynucleotides by a 5' cholesteryl moiety increases cellular association and improves efficacy", *Proceedings of the National Academy of Science*, 90: 1048-1052, 1993.

Krieg et al., "The role of CpG dinucleotides in DNA vaccines", *Trends in Microbiology*, 6: 23-27, 1998.

Krieg et al., "An innate immune defense mechanism based on the recognition of CpG motifs in microbial DNA", *Journal of Laboratory Clinical Medicine*, 128(2): 128-33, 1996.

Krieg et al., Abstract from 1996 meeting on Molecular Approaches to the Control of Infectious Diseases, Cold Spring Harbor Laboratory, Sep. 9-13, 1996. p. 116.

Krieg et al., "Enhancing vaccines with immune stimulatory CpG DNA", *Current Opinions Molecular Theory*, 3(1): 15-24, 2001.

Krieg et al., "CpG oligonucleotides as immune adjuvants", Ernst Schering Res Found Workshop; 2000;(30):105-18. Review.

Krieg et al., "Immune effects and mechanisms of action of CpG motifs", *Vaccine*, 19(6): 618-22, 2001.

Krieg et al. "The role of CpG motifs in innate immunity", *Current Opinions Immunology*, 12: 35, 2000.

Krieg et al., "Mechanism of Action in CpG DNA", *Current Topics in Microbiology and Immunology*, 247: 1-21, 2000.

Krieg et al., "Mechanisms and therapeutic applications of immune stimulatory cpG DNA", *Pharmacological Theory*, 84: 113, 1999.

Krieg et al., "Sequence motifs in adenoviral DNA block immune activation by stimulatory CpG motifs", *Proceedings of the National Academy of Science*, 95: 12631-636, 1998.

Krieg et al., "CpG DNA induces sustained IL-12 expression in vivo and resistance to Listeria monocytogenes challenge", *Journal of Immunology*, 161(5): 2428-2434, 1998.

Krown et al., *Journal of Interferon Research*, 3: 281, 1983.

Krown et al., "Interferons and interferon inducers in cancer treatment", *Seminars in Oncology*, 13(2): 207-17, 1986.

Kuramoto et al., "Changes of host cell infiltration into Meth a fibrosarcoma tumor during the course of regression induced by injections of a BCG nucleic acid fraction", *International Immunopharmacology*, 14(5): 773-782, 1992.

Kuramoto et al., "Oligonucleotide sequences required for natural killer cell activation", *Japan Journal of Cancer Research*, 83: 1128-1131, 1992.

Kuramoto et al., "In situ infiltration of natural killer-like cells induced by intradermal injection of the nucleic acid fraction from BCG", *Microbiological Immunology*, 33(11): 929-940, 1989.

Lally et al., "Unmasking cryptic epitopes after loss of immunodominant tumor antigen expression through epitope spreading", *International Journal of Cancer*,93(6): 841-7, 2001.

Lederman et al., "Polydeoxyguanine motifs in a 12-mer phosphorothioate oligodeoxynucleotide augment binding to the v3 loop of HIV-1 gp120 and potency of HIV-1 inhibition independency of G-tetrad formation", *Antisense Nucleic Acid Drug Development*, 6: 281-9, 1996.

Lee et al., "An oligonucleotide blocks interferon-gamma signal transduction", *Transplantation*, 62: 1297-1301, 1996.

Leonard et al., "Conformation of guanine-8-oxoadenine base pairs in the crystal structure of d(CGCGAATT(O8A)GCG)", *Biochemistry*, 31(36): 8415-8420, 1992.

Levine et al., "Phase I-II trials of poly IC stabilized with poly-L-lysine",*Cancer Treatment Reports*, 62: 1907, 1978.

Levy et al., *Journal of Infectious Disease*, 133: A256, 1976.

Liau et al., "Tumor immunity within the central nervous system stimulated by recombinant Listeria monocytogenes vaccination", *Cancer Research*, 62(8): 2287-93, 2002.

Lipford et al., "CpG-containing synthetic oligonucleotides promote B and cytotoxic T cell responses to protein antigen: a new class of vaccine adjuvants", *European Journal of Immunology*, 27(9): 2340-4, 1997.

Lipford et al., "Immunostimulatory DNA: sequence-dependent production of potentially harmful or useful cytokines", *European Journal of Immunology*, 27: 3420-6, 1997.

Lipford et al., "Bacterial DNA as immune cell activator", *Trends Microbiological*, 6(12): 496-500, 1998.

Liu et al., "Immunostimulatory CpG oligodeoxynucleotides enhance the immune response to vaccine strategies involving granulocyte-macrophage colony-stimulating factor", *Blood*, 92(10): 3730-3736, 1998.

Loke et al., "Delivery of c-myc antisense phosphorothioate oligodeoxynucleotides to hematopoietic cells in culture by liposome fusion: specific reduction in c-myc protein expression correlates with inhibition of cell growth and DNA synthesis", *Current Topics Microbiological Immunology*, 141: 282, 1988.

Macaya et al., "Thrombin-binding DNA aptamer forms a unimolecular quadruplex structure in solution", *Proceedings of the National Academy of Science*, 90: 3745-9, 1993.

Malanchere-Bres et al., "CpG oligodeoxynucleotides with hepatitis B surface antigen (HBsAg) for vaccination in HBsAg-transgenic mice", *Journal of Virology*, 75(14): 6482-6491, 2001.

Maltese et al., "Sequence context of antisense RelA/NF-kappa B phosphorothioates determines specificity", *Nucleic Acids Research*, 23: 1146-51, 1995.

Manzel et al., "CpG-oligodeoxynucleotide-resistant variant of WEHI 231 cells", *Journal of Leukocyte Biology*, 66: 817, 1999.

Markiewicz et al., "Epitope spreading upon P815 tumor rejection triggered by vaccination with the single class I MHCc-restricted peptide PIA", *International Immunology*, 13(5): 625-32, 2001.

Matson et al., "Nonspecific suppression of [3H]thymidine incorporation by "control" oligonucleotides", *Antisense Research and Development*, 2(4): 325-30, 1992.

Matsukura et al., "Regulation of viral expression of human immunodeficiency virus in vitro by an antisense phosphorothioate oligodeoxynucleotide against rev (art/trs) in chronically infected cells", *Proceedings of the National Academy of Science USA*, 86: 4244-48, 1989.

McCluskie et al., "CpG DNA is a potent enhancer of systemic and mucosal immune responses against hepatitis B surface antigen with intranasal administration to mice", *Journal of Immunology*, 161: 4463-6, 1998.

McCluskie et al., *Vaccine*, 18: 231-237, 2000.

McCluskie et al., "Oral, intrarectal and intranasal immunizations using CpG and non-CpG oligodeoxynucleotides as adjuvants", *Vaccine*, 19: 413-422, 2001.

McCluskie et al., "CpG DNA is an effective oral adjuvant to protein antigens in mice", *Vaccine*, 19: 950, 2001.

McCluskie et al., "The potential of oligodeoxynucleotides as mucosal and parenteral adjuvants", *Vaccine*, 19: 2657-2660, 2001.

McCluskie et al., "The use of CpG DNA as a mucosal vaccine adjuvant", *Current Opinions Investigational Drugs*, 2(1):35-9, 2001.

McCluskie et al., "Mucosal immunization of mice using CpG DNA and/or mutants of the heat-labile enterotoxin of *Escherichia coli* as adjuvants", *Vaccine*, 19(27): 3759-68, 2001.

McCluskie et al., "The potential of CpG oligodeoxynucleotides as mucosal adjuvants", *Critical Reviews in Immunology*, 21(1-3): 103-20, 2001.

McCluskie et al., "Parenteral and mucosal prime-boost immunization strategies in mice with hepatitis B surface antigen and CpG DNA", *FEMS Immunology Medicine Microbiology*, 32(3): 179-85, 2002.

McCluskie et al., "Mucosal immunization with DNA vaccines", *Microbes and Infection*, 1(9): 685-98, 1999.

McCluskie et al., "Intranasal immunization of mice with CpG DNA induces strong systemic and mucosal responses that are influenced by other mucosal adjuvants and antigen distribution", *Molecular Medicine*, 6(10): 867-77, 2000.

McCluskie et al., "The role of CpG in DNA vaccines", *Springer Seminars in Immunopathology*, 22(1-2): 125-32, 2000.

McIntyre et al., "A sense phosphorothioate oligonucleotide directed to the initiation codon of transcription factor NF-kappa B p65 causes sequence-specific immune stimulation", *Antisense Research and Development*, 3(4): 309-22, 1993.

Messina et al., "Stimulation of in vitro murine lymphocyte proliferation by bacterial DNA", *Journal of Immunology*, 147(6): 1759-1764, 1991.

Michelson et al. "Poly(A).poly(U) as adjuvant in cancer treatment distribution and pharmacokinetics in rabbits", *Proceedings of Society of Experimental Biological Medicine*, 179: 180, 1985.

Moldoveanu et al., "CpG DNA, a novel immune enhancer for systemic and mucosal immunization with influenza virus", *Vaccine*, 16(11-12): 1216-1224, 1998.

New England Biolabs, 1988-1989 Catalog.

Nyce et al., "DNA antisense therapy for asthma in an animal model", *Nature*, 385: 721-725, 1997.

Okada et al., "Bone marrow-derived dendritic cells pulsed with a tumor-specific peptide elicit effective anti-tumor immunity against intracranial neoplasms", *International Journal of Cancer*, 78(2): 196-201, 1998.

Pal et al., "Immunization with the Chlamydia trachomatis mouse pneumonitis major outer membrane protein by use of CpG oligodeoxynucleotides as an adjuvant induces a protective immune response against an intranasal chlamydial challenge", *Infection and Immunity*, 70(9): 4812-7, 2002.

Park et al. "Adjuvant effect of polyadenylic.polyuridylic acid on antibody production of recombinant hepatitis B surface antigen in mice", *International Journal of Immunopharmacology*, 17(6): 513, 1995.

Payette et al., "History of vaccines and positioning of current trends", *Current Drugs Targets for Infection and Disorders*, 1(3): 241-7, 2001.

Pisetsky et al., "The immunologic properties of DNA", *Journal of Immunology*, 156(2): 421-3, 1996.

Pisetsky et al., "Stimulation of murine lymphocyte proliferation by a phosphorothioate oligonucleotide with antisense activity for herpes simplex virus", *Life Sciences*, 54(2): 101-107, 1994.

Pisetsky et al., "Immunologic consequences of nucleic acid therapy", *Antisense Research and Development*, 5(3):219-225, 1995.

Pisetsky et al., "Stimulation of in vitro proliferation of murine lymphocytes by synthetic oligodeoxynucleotides", *Molecular Biology Reports*, 18: 217-221, 1993.

Pisetsky et al., "The influence of base sequence on the immunostimulatory properties of DNA", *Immunity Research*, 19: 35-46, 1999.

Ranieri et al., "Dendritic cell/peptide cancer vaccines: clinical responsiveness and epitope spreading", *Immunology Investigations*, 29(2): 121-5, 2000.

Raz et al., "Preferential induction of a Th1 immune response and inhibition of specific IgE antibody formation by plasmid DNA immunization", *Proceedings of the National Academy of Science USA*, 93(10): 5141-5, 1996.

Roman et al., "Immunostimulatory DNA sequences function as T helper-1-promoting adjuvants", *Nature Medicine*, 3(8): 849-54, 1997.

Sajic et al., "Parameters of CpG oligodeoxynucleotide-induced protection against intravaginal HSV-2 challenge", *Journal of Medical Virology*, 71(4): 561-568, 2003.

Sarmiento et al., "In vivo toxicological effects of rel a antisense phosphorothioates in CD-1 mice", *Antisense Research and Development*, 4: 99-107, 1994.

Sato et al., "Immunostimulatory DNA sequences necessary for effective intradermal gene immunization", *Science*, 273: 352-354, 1996.

Schwartz et al., "CpG motifs in bacterial DNA cause inflammation in the lower respiratory tract", *Journal of Clinical Investigation*, 100(1): 68-73, 1997.

Sethi et al., "Postexposure prophylaxis against prion disease with a stimulator of innate immunity", *Lancet*, 360: 229-230, 2002.

Sparwasser et al., "Bacterial DNA and immunostimulatory CpG oligonucleotides trigger maturation and activation of murine dendritic cells", *European Journal of Immunology*, 28(6): 2045-54, 1998.

Sparwasser et al., "Macrophages sense pathogens via DNA motifs: induction of tumor necrosis factor-alpha-mediated shock", *European Journal of Immunology*, 27(7): 1671-9, 1997.

Stacey et al. "Immunostimulatory DNA as an adjuvant in vaccination against Leishmania major", *Infection and Immunity*, 67: 3719-3726, 1999.

Sun et al. *Journal of Experimental Medicine*, 188: 2335, 1998.

Sun et al. *Springer Seminars in Immunopathology*, 22: 77, 2000.

Talmadge et al., "Immunomodulatory effects in mice of polyinosinic-polycytidylic acid complexed with poly-L-lysine and carboxymethylcellulose", *Cancer Research*, 45(3): 1058-65, 1985.

Threadgill et al., "Mitogenic synthetic polynucleotides suppress the antibody response to a bacterial polysaccharide", *Vaccine*, 16(1): 76-82, 1998.

Tokunaga et al., "A synthetic single-stranded DNA, poly(dG,dC), induces interferon-alpha/beta and—gamma, augments natural killer activity, and suppresses tumor growth", *Japan Journal of Cancer Research*, 79(6): 682-6, 1988.

Tokunaga et al., "Synthetic oligonucleotides with particular base sequences from the cDNA encoding proteins of *Mycobacterium bovis* BCG induce interferons and activate natural killer cells", *Microbiological Immunology*, 36(1): 55-66, 1992.

Vanderlugt et al., "Epitope spreading in immune-mediated diseases: implications for immunotherapy", *Nature Reviews in Immunology*, 2(2): 85-95, 2002.

Waag et al., "Injection of inactivated phase I *Coxiella bumetii* increases non-specific resistance to infection and stimulates lymphokine production in mice", *Annual New York Academy of Science*, 590: 203-214, 1990.

Walker et al., *Proceedings of the National Academy of Science, USA*, 96: 6970-6975, 1999.

Warren et al., "APC stimulated by CpG oligodeoxynucleotide enhance activation of MHC class I-restricted T cells", *Journal of Immunology*, 165: 6244, 2000.

Weeratna et al., "Reduction of antigen expression from DNA vaccines by coadministered oligodeoxynucleotides", *Antisense & Nucleic Drug Development*, 8: 351-356, 1998.

Weeratna et al., "CPG ODN allows lower dose of antigen against hepatitis B surface antigen in BALB/c mice", *Immunology Cell Biology*, 81(1): 59-62, 2003.

Weeratna et al, "CpG ODN can re-direct the Th bias of established Th2 immune responses in adult and young mice", *FEMS Immunology Medicine Microbiology*, 32(1): 65-71, 2001.

Weeratna et al., "CpG DNA induces stronger immune responses with less toxicity than other adjuvants", *Vaccine*, 18(17): 1755-62, 2000.

Weeratna et al., "Priming of immune responses to hepatitis B surface antigen in young mice immunized in the presence of maternally derived antibodies", *FEMS Immunology Medicine Microbiology*, 30(3): 241-7, 2001.

Weiner et al., "Immunostimulatory oligodeoxynucleotides containing the CpG motif are effective as immune adjuvants in tumor antigen immunization", *Proceedings of the National Academy of Science USA*, 94(20): 10833-7, 1997.

Wernette et al., "CpG oligodeoxynucleotides stimulate canine and feline immune cell proliferation", *Veterinary Immunology and Immunopathology*, 84(3-4): 223-236, 2002.

Wooldridge et al. *Proceedings of American Association for Cancer Research*, 37: 477, 1996.

Wooldridge et al., "Immunostimulatory oligodeoxynucleotides containing CpG motifs enhance the efficacy of monoclonal antibody therapy of lymphoma", *Blood*, 89(8): 2994-2998, 1997.

Wu et al., "Receptor-mediated gene delivery and expression in vivo", *Journal of Biological Chemistry*, 263: 14621-14624, 1988.

Wyatt et al. "Combinatorially selected guanosine-quartet structure is a potent inhibitor of human immunodeficiency virus envelope-mediated cell fusion", *Proceedings of the National Academy of Science USa*, 91: 1356-60, 1994.

Yamamoto et al., "Lipofection of synthetic oligodeoxyribonucleotide having a palindromic sequence of AACGTT to murine splenocytes enhances interferon production and natural killer activity", *Microbiological Immunology*, 38(10): 831-836, 1994.

Yamamoto et al., "Unique palindromic sequences in synthetic oligonucleotides are required to induce IFN [correction of INF] and augment IFN-mediated [correction of INF] natural killer activity", *Journal of Immunology*, 148(12): 4072-4076, 1992.

Yamamoto et al., "[Commemorative lecture of receiving Imamura Memorial Prize. II. Mode of action of oligonucleotide fraction extracted from *Mycobacterium bovis* BCG]", *Kekkaku*, 69(9): 571-4, 1994.

Yamamoto et al., "Ability of oligonucleotides with certain palindromes to induce interferon production and augment natural killer cell activity is associated with their base length", *Antisense Research and Development*, 4(2): 119-123, 1994.

Yamamoto et al., "Synthetic oligonucleotides with certain palindromes stimulate interferon production of human peripheral blood lymphocytes in vitro", *Japan Journal of Cancer Research*, 85: 775-779, 1994.

Yi et al. "Rapid induction of mitogen-activated protein kinases by immune stimulatory CpG DNA", *Journal of Immunology*, 161: 4493, 1998.

Yi et al., "Rapid immune activation by CpG motifs in bacterial DNA. Systemic induction of IL-6 transcription through an antioxidant-sensitive pathway", *Journal of Immunology*, 157:5394-5402, 1996.

Yi et al., "IFN-gamma promotes Il-6 and IgM secretion in response to CpG motifs in bacterial DNA and oligodeoxynucleotides", *Journal of Immunology*, 156(2): 558-64, 1996.

Yi et al. "CpG oligodeoxyribonucleotides rescue mature spleen B cells from spontaneous apoptosis and promote cell cycle entry", *Journal of Immunology*, 160: 5898, 1998.

Zimmermann et al., "CpG oligodeoxynucleotides trigger protective and curative Th1 responses in lethal murine leishmaniasis", *Journal of Immunology*, 160(8): 3627-3630 1998.

Press Release, Jan. 2007, "Coley Pharmaceutical Group Updates Hepatitis C Drug Development Strategy".

Press Release, Jun. 2007, "Coley Pharmaceutical Group Announces Pfizer's Discontinuation of Clinical Trials for PF-3512676 Combined with Cytotoxic Chemotherapy in Advanced Non Small Cell Lung Cancer".

Bennett, Intracellular delivery of oligonucleotides with cationic liposomes. In: Delivery Strategies for Antisense Oligonucleotide Therapeutics. Akthar, Ed. 1995:223-32.

Bhagat et al., CpG penta- and hexadeoxyribonucleotides as potent immunomodulatory agents. Biochem Biophys Res Commun. Jan. 24, 2003;300(4):853-61.

Cho et al., Immunostimulatory DNA-based vaccines induce cytotoxic lymphocyte activity by a t-helper cell-independent mechanism. Nature. May 2000; 18:509-14.

Davis et al., DNA vaccines for prophylactic or therapeutic immunization against hepatitis B virus. Mt Sinai J Med. Mar. 1999;66(2):84-90. Review.

Horner et al., Immunostimulatory sequence oligodeoxynucleotide: A novel mucosal adjuvant. Clin Immunol. Apr. 2000;95(1 Pt 2):S19-29.

Klinman et al., CpG DNA: recognition by and activation of monocytes. Microbes Infect. Jul. 2002;4(9):897-901.

Krieg, Now I know my CpGs.Trends Microbiol. Jun. 2001;9(6):249-52.

Lee et al., Effects of a hexameric deoxyriboguanosine run conjugation into CpG oligodeoxynucleotides on their immunostimulatory potentials. J Immunol. Oct. 1, 2000;165(7):3631-9.

Li et al., Enhanced immune response to T-independent antigen by using CpG oligodeoxynucleotides encapsulated in liposomes. Vaccine. Oct. 12, 2001;20(1-2):148-57.

Lipford et al., Poly-guanosine motifs costimulate antigen-reactive CD8 T cells while bacterial CpG-DNA affect T-cell activation via antigen-presenting cell-derived cytokines. Immunology. Sep. 2000;101(1):46-52.

Maurer et al., CpG-DNA aided cross-presentation of soluble antigens by dendritic cells. Eur J Immunol. Aug. 2002;32(8):2356-64.

Norman et al., Liposome-mediated, nonviral gene transfer induces a systemic inflammatory response which can exacerbate pre-existing inflammation. Gene Ther. 2000;7:1425-30.

Oehen et al., Antiviral protection after DNA vaccination is short lived and not enhanced by CpG DNA. Immunology. Feb. 2000;99(2):163-9.

Oxenius et al., CpG-containing oligonucleotides are efficient adjuvants for induction of protective antiviral immune responses with T-cell peptide vaccines. J Virol. May 1999;73(5):4120-6.

Shirota et al., Novel roles of CpG oligodeoxynucleotides as a leader for the sampling and presentation of CpG-tagged antigen by dendritic cells. J Immunol. Jul. 1, 2001;167(1):66-74.

Tokunaga, Response of the organism to DNA—With a focus on immunostimulatory DNA. Kansen Ensho Meneki. 2001 Autumn; 31(3): 1-12. Japanese.

Uhlmann et al., Recent advances in the development of immunostimulatory oligonucleotides. Curr Opin Drug Discov Devel. Mar. 2003;6(2):204-17.

Von Hunolstein et al., The adjuvant effect of synthetic oligodeoxynucleotide containing CpG motif converts the anti-Haemophilus influenzae type b glycoconjugates into efficient anti-polysaccharide and anti-carrier polyvalent vaccines. Vaccine. Apr. 30, 2001;19(23-24):3058-66.

Whalen et al., DNA-mediated immunization to the hepatitis B surface antigen. Activation and entrainment of the immune response. Ann N Y Acad Sci. Nov. 27, 1995;772:64-76.

Whitmore et al., Systemic administration of LPD prepared with CpG oligonucleotides inhibits the growth of established pulmonary metastases by stimulating innate and acquired antitumor immune responses. Cam Immun Immunother. 2001;50:503-14.

Yu et al., 'Immunomers'—novel 3'-3'-linked CpG oligodeoxyribonucleotides as potent immunomodulatory agents. Nucleic Acids Res. Oct. 15, 2002;30(20):4460-9.

Yu et al., Modulation of immunostimulatory activity of CpG oligonucleotides by site-specific deletion of nucleobases. Bioorg Med Chem Lett. Sep. 3, 2001;11(17):2263-7.

Zhang et al., Antisense oligonucleotide inhibition of hepatitis C virus (HCV) gene expression in livers of mice infected with an HCV-vaccinia virus recombinant. Antimicrob Agents Chemother. Feb. 1999;43(2):347-53.

Zhao et al., Immunostimulatory activity of CpG containing phosphorothioate oligodeoxynucleotide is modulated by modification of a single deoxynucleoside. Bioorg Med Chem Lett. May 15, 2000;10(10):1051-4. Abstract Only.

Alexakis et al., Microencapsulation of DNA within alginate microspheres and crosslinked chitosan membranes for in vivo application. Appl Biochem Biotechnol. Jan. 1995;50(1):93-106.

Hartmann et al., Rational design of new CpG oligonucleotides that combine B cell activation with high IFN-alpha induction in plasmacytoid dendritic cells. Eur J Immunol. Jun. 2003;33(6):1633-41.

Kandimalla et al., Secondary structures in CpG oligonucleotides affect immunostimulatory activity. Biochem Biophys Res Commun. Jul. 11, 2003;306(4):948-53.

Lee et al., Effects of a hexameric deoxyriboguanosine run conjugation into CpG oligodeoxynucleotides on their immunostimulatory potentials. J Immunol. Oct. 1 2000;165(7):36319.

Mutwiri et al., Biological activity of immunostimulatory CpG DNA motifs in domestic animals. Vet Immunol Immunopathol. Jan. 30, 2003;91(2):89-103.

Storey et al., Anti-sense phosphorothioate oligonucleotides have both specific and non-specific effects on cells containing human papillomavirus type 16. Nucleic Acids Res. Aug. 11, 1991;19(15):4109-14.

Yamada et al., Effect of suppressive DNA on CpG-induced immune activation. J Immunol. Nov. 15, 2002;169(10):5590-4.

Yu et al., Potent CpG oligonucleotides containing phosphodiester linkages: in vitro and in vivo immunostimulatory properties. Biochem Biophys Res Commun. Sep. 13, 2000;297(1):83-90.

Zhang et al., Antisense oligonucleotide inhibition of hepatitis C virus (HCV) gene expression in livers of mice infected with an HCV-vaccinia virus recombinant. Antimicrob Agents Chemother. Feb. 1999;43(2):347-53.

Fathi et al., Oligonucleotides with novel, cationic backbone substituents: aminoethylphosphonates. Nucleic Acids Res, Dec. 11, 1994;22(24):5416-24.

Jiang et al., Synthetic vaccines: the role of adjuvants in immune targeting. Curr Med Chem. Aug. 2003;10(15):1423-39.

Joseph et al., Liposomal immunostimulatory DNA sequence (ISS-ODN): an efficient parenteral and mucosal adjuvant for influenza and hepatitis B vaccines. Vaccine. Sep. 10, 2002;20(27-28):3342-54.

Lyer et al., Modified oligonucleotides—synthesis, properties and applications. Curr Opin Mol Ther. Jun. 1999;1(3):344-58. Review.

Marshall et al., Identification of a novel CpG DNA class and motif that optimally stimulate B cell and plasmacytoid dendritic cell functions. J Leukoc Biol. Jun. 2003;73(6):781-92.

Scheule, The role of CpG motifs in immunostimulation and gene therapy. Adv Drug Deliv Rev. Nov. 15, 2000;44(2-3):119-34.

Verthelyi et al., CpG oligodeoxynucleotides as vaccine adjuvants in primates. J Immunol. Feb. 15, 2002;168(4):1659-63.

Vollmer et al., Identification of a new class of CpG oligonucleotides capable of inducing both B cell proliferation and high IFN-alpha secretion from PBMC of HCV chronic carriers. Antiv Ther. 2002;7:L115.

Vollmer, CpG motifs to modulate innate and adaptive immune responses. Int Rev Immunol, May-Aug. 2006;25(3-4):125-34. Abstract.

Wilson et al., Complex roles of CpG in liposomal delivery of DNA and oligonucleotides. Biosci Rep. Apr. 2002;22(2):309-22. Review.

Yu et al., 'Immunomers'—novel 3'-3'-linked CpG oligodeoxyribonucleotides as potent immunomodulatory agents. Nucleic Acids Res. Oct. 15, 2002;30(20):4460-9.

Agrawal, Importance of nucleotide sequence and chemical modifications of antisense oligonucleotides. Biochim Biophys Acta. Dec. 10, 1999;1489(1):53-68. Review.

Azuma et al., Development of immunoadjuvants for immunotherapy of cancer. Int Immunopharmacol. Jul. 2001;1(7):1249-59. Review.

Fearon et al., a minimal human immunostimulatory CpG motif that potently induces IFN-gamma and IFN-alpha production. Eur J Immunol. Aug. 2003;33(8):2114-22.

Ioannou et al., CpG-containing oligodeoxynucleotides, in combination with conventional adjuvants, enhance the magnitude and change the bias of the immune responses to a herpesvirus glycoprotein. Vaccine. 2002: 21; 127-37.

Jorgensen et al., CpG DNA induces protective antiviral immune responses in Atlantic salmon (*Salmo salar* L.). J Virol. Nov. 2003;77(21):11471-9.

Krieg et al., Identification of an oligodeoxynucleotide sequence motif that specifically inhibits phosphorylation by protein tyrosine kinases. Antisense Nucleic Acid Drug Dev. Apr. 1997;7(2):115-23.

Samani et al., Best minimally modified antisense oligonucleotides according to cell nuclease activity. Antisense Nucleic Acid Drug Dev. Jun. 2001;11(3):129-36.

Sonehara et al., Hexamer palindromic oligonucleotides with 5'-CG-3' motif(s) induce production of interferon. J Interferon Cytokine Res. Oct. 1996;16(10):799-803.

Uhlmann et al., Use of minimally modified antisense oligonucleotides for specific inhibition of gene expression. Methods Enzymol. 2000;313:268-84.

Uhlmann, Oligonucleotide technologies: synthesis, production, regulations and applications. Nov. 29-30, 2000, Hamburg, Germany. Expert Opin Biol Ther. Mar. 2001;1(2):319-28.

Wahlestedt et al., Potent and nontoxic antisense oligonucleotides containing locked nucleic acids. Proc Natl Acad Sci U S A. May 9, 2000;97(10):5633-8.

Yu et al, Immunostimulatory activity of CpG oligonucleotides containing non-ionic methylphosphonate linkages. Bioorg Med Chem. Nov. 2001;9(11):2803-8.

* cited by examiner

Example: A phosphodiester linkage between the C and G of the 5' CpG dinucleotide results in enhancement of potency of immune stimulation.

5' CPG NUCLEIC ACIDS AND METHODS OF USE

RELATED APPLICATIONS

This application claims priority under 35 U.S.C. §119(e) to U.S. Provisional Application Ser. No. 60/432,409, filed Dec. 11, 2002 and U.S. Ser. No. 60/506,108 filed Sep. 25, 2003, which are herein incorporated by reference in their entirety.

FIELD OF THE INVENTION

The present invention relates generally to immunostimulatory nucleic acids, compositions thereof and methods of using the immunostimulatory nucleic acids.

BACKGROUND OF THE INVENTION

Bacterial DNA has immune stimulatory effects to activate B cells and natural killer cells, but vertebrate DNA does not (Tokunaga, T., et al., 1988. *Jpn. J. Cancer Res.* 79:682-686; Tokunaga, T., et al., 1984, *JNCI* 72:955-962; Messina, J. P., et al., 1991, *J. Immunol.* 147:1759-1764; and reviewed in Krieg, 1998, In: Applied Oligonucleotide Technology, C. A. Stein and A. M. Krieg, (Eds.), John Wiley and Sons, Inc., New York, N.Y., pp. 431-448) and Krieg. A. M. CpG motifs in bacterial DNA and their immune effects (2002) Annu. Rev. Immunol. 20: 709-760. It is now understood that these immune stimulatory effects of bacterial DNA are a result of the presence of unmethylated CpG dinucleotides in particular base contexts (CpG motifs), which are common in bacterial DNA, but methylated and underrepresented in vertebrate DNA (Krieg et al, 1995 Nature 374:546-549; Krieg, 1999 Biochim. Biophys. Acta 93321:1-10). The immune stimulatory effects of bacterial DNA can be mimicked with synthetic oligodeoxynucleotides (ODN) containing these CpG motifs. Such CpG ODN have highly stimulatory effects on human and murine leukocytes, inducing B cell proliferation; cytokine and immunoglobulin secretion; natural killer (NK) cell lytic activity and IFN-γ secretion; and activation of dendritic cells (DCs) and other antigen presenting cells to express costimulatory molecules and secrete cytokines, especially the Th1-like cytokines that are important in promoting the development of Th1-like T cell responses. These immune stimulatory effects of native phosphodiester backbone CpG ODN are highly CpG specific in that the effects are dramatically reduced if the CpG motif is methylated, changed to a GpC, or otherwise eliminated or altered (Krieg et al, 1995 Nature 374:546-549; Hartmann et al, 1999 Proc. Natl. Acad. Sci USA 96:9305-10).

In early studies, it was thought that the immune stimulatory CpG motif followed the formula purine-purine-CpG-pyrimidine-pyrimidine (Krieg et al, 1995 Nature 374:546-549; Pisetsky, 1996 J. Immunol. 156:421-423; Hacker et al., 1998 EMBO J. 17:6230-6240; Lipford et al, 1998 Trends in Microbiol. 6:496-500). However, it is now clear that mouse lymphocytes respond quite well to phosphodiester CpG motifs that do not follow this "formula" (Yi et al., 1998 J. Immunol. 160:5898-5906) and the same is true of human B cells and dendritic cells (Hartmann et al, 1999 Proc. Natl. Acad. Sci USA 96:9305-10; Liang, 1996 J. Clin. Invest. 98:1119-1129). Nevertheless, the term "CpG motif" is generally used to refer to a hexamer motif in which the CpG dinucleotide is located at the center.

SUMMARY OF THE INVENTION

The invention involves the finding that specific sub-classes of CpG immunostimulatory oligonucleotides having a 5'CpG are highly effective in mediating immune stimulatory effects. These CpG nucleic acids are useful therapeutically and prophylactically for stimulating the immune system to treat cancer, infectious diseases, allergy, asthma and other disorders and to help protect against opportunistic infections following cancer chemotherapy. The strong yet balanced, cellular and humoral immune responses that result from CpG stimulation reflect the body's own natural defense system against invading pathogens and cancerous cells.

In particular, immunostimulatory CpG containing oligonucleotides having a 5'TCG motif, rather than the conventional hexamer motif have important therapeutic properties. It has been discovered that oligonucleotides having a '5TCG motif without any additional unmethylated CpG motifs have strong immunostimulatory capability. In one aspect the invention is a composition comprising an oligonucleotide: 5'TCGX$_1$X$_2$N$_1$3', wherein N$_1$ is 2-95 nucleotides and, when X$_1$ is C or A, X$_2$ is A, T, or C (SEQ. ID NO.: 61); when X$_1$ is T, X$_2$ is A or G (SEQ. ID NO.: 62); and when X$_1$ is G, X$_2$ is any nucleotide (SEQ. ID NO.: 63).

The invention, in other aspects, relates to an oligonucleotide comprising 5'TCGTN$_1$3' (SEQ. ID NO.: 64). In the oligonucleotide N$_1$ is 3-96 nucleotides, but when N$_1$ is 16 nucleotides N$_1$ does not include a C$_{12}$ (5'-CCCCCCCCCCCC-3' SEQ. ID NO.: 65), and when N$_1$ is 8 nucleotides N$_1$ is at least 50% C or 70% T (SEQ. ID NO.: 66).

According to other aspects, an oligonucleotide comprising 5'TCGAN$_1$3' (SEQ. ID NO.: 67) is provided. In the oligonucleotide N$_1$ is 3-96 nucleotides, but when N$_1$ is 19 nucleotides N$_1$ is at least 55% pyrimidine (SEQ. ID NO.: 68), and when N$_1$ is 8 nucleotides N$_1$ is at least 50% T or C (SEQ. ID NO.: 69).

According to other aspects, an oligonucleotide comprising 5'TCGN$_1$3' is provided. In the oligonucleotide N$_1$ is 10-96 nucleotides, and the C content of the oligonucleotide is less than or equal to 60%, and the A content of the oligonucleotide is less than or equal to 30%.

According to other aspects, an oligonucleotide is provided that comprises 5'TYZN$_1$3'. In the oligonucleotide N$_1$ is 4-97 nucleotides, and the oligonucleotide does not include an unmethylated CG motif. Y is a cytosine or modified cystosine. Z is a guanine or modified guanine. In one embodiment Y is 5'methyl cytosine, 5-methyl-deoxycytosine, 5-methyl-deoxyisocytosine, 5-hydroxy-deoxycytosine, deoxyuridine, N$_4$-ethyl-deoxycytosine, 2'-deoxyuridine, 5-fluoro-2'-dU, and dSpacer. In other embodiments Z is 7-deazaguanine, 7-deaza-7-substituted guanine (such as 7-deaza-7-(C2-C6) alkynylguanine), 7-deaza-8-substituted guanine, hypoxanthine, 2,6-diaminopurine, 2-aminopurine, purine, 8-substituted guanine such as 8-hydroxyguanine, and 6-thioguanine, Inosine, 2-aminopurine, nebularine, and dSpacer.

In the oligonucleotide formulas 5' refers to the free 5' end of the oligonucleotide and 3' refers to the free 3' end of the oligonucleotide.

In some embodiment the oligonucleotide has one of the following structures: 5' T*C*G*A*G*G*A*C*T*T*C*T*C*T*C*A*G*G*T*T 3' (SEQ. ID NO.: 50) or 5' T*C*G*T*T*T*T*T*T*T*T*T*T*T*T*T*T 3' (SEQ. ID NO.: 2) The * refers to a phosphorothioate linkage.

According to one embodiment the oligonucleotide includes at least 1 modified internucleotide linkage. In other embodiments the oligonucleotide includes at least 50% modified internucleotide linkages. Optionally all internucleotide linkages of the oligonucleotide are modified. The stabilized internucleotide linkage may be a phosphorothioate linkage.

In some embodiments the oligonucleotide is 20-100 nucleotides in length. In other embodiments it is 40 or less nucleotides in length.

$N_1$ is free of unmethylated CG motifs. $N_1$ may be defined by $N_2N_3$, such that $N_2$ is 8-94 nucleotides, or in some embodiments 8-40 nucleotides, and $N_3$ is 2-5 pyrimidines. In some embodiments $N_3$ is TTTTT, TTTT, TTT, or TT. $N_1$, according to other embodiments, may be at least 50% pyrimidine or at least 80% pyrimidine. In yet other embodiments $N_1$ is free of Poly-A and Poly-G sequences. In other embodiments $N_1$ is $TN_2$ and $N_2$ is 8-94 nucleotides.

The invention involves, in one aspect, the discovery that the 5' sequence of immunostimulatory nucleotides, their length and internucleotide linkage have specific influences on the cytokine profile of the induced immune response and that these discoveries can be used to design a subset of CpG immunostimulatory oligonucleotides that have improved immune stimulatory properties. The preferred CpG immunostimulatory oligonucleotides fall within one of the following 6 general formulas: 5'-$X_1$YR$M_1$-3', 5'-$X_2$CG$M_2$-3', 5'-$X_3$CG$M_3$-3', 5'-$X_4$CG$M_4$-3', 5'-$X_5$CG$M_5$-3' and 5'-TTG$M_6$-3'. The formulas define subsets of the class of CpG oligonucleotides which demonstrated excellent immune stimulating properties and yet do not include additional unmethylated CpG motifs. In the formulas 5' refers to the free 5' end of the oligonucleotide and 3' refers to the free 3' end of the oligonucleotide.

In one aspect of the invention the ODN has the general formula 5'-$X_1$YR$M_1$-3', wherein $X_1$ is a single nucleotide; Y is a cytosine or a modified cytosine; R is a guanine or a modified guanine; and $M_1$ is a nucleic acid of 1-3 nucleotides. According to other embodiments of the invention, the internucleotide linkages of the oligonucleotide are all stabilized phosphorothioate internucleotide linkages. In one embodiment, the internucleotide linkage between Y and R is a phosphodiester linkage in an Rp configuration. In some embodiments of the invention, the modified cytosine has a C5 substitution and/or the modified guanine has a C8 or C7 substitution. In certain embodiments of the invention, the substituted or modified C or G is selected from the group consisting of 5-substituted cytosines (e.g. 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g. N4-ethyl-cytosine), 5-aza-cytosine, 2-mercapto-cytosine, isocytosine, pseudo-isocytosine, cytosine analogs with condensed ring systems (e.g. N,N'-propylene cytosine or phenoxazine), and uracil and its derivatives (e.g. 5-fluoro-uracil, 5-bromo-uracil, 5-bromovinyl-uracil, 4-thio-uracil, 5-hydroxy-uracil, 5-propynyl-uracil), thymine derivatives (e.g. 2-thiothymine, 4-thiothymine, 6-substituted thymines), 7-deazaguanine, 7-deaza-7-substituted guanine (such as 7-deaza-7-($C_2$-$C_6$)alkynylguanine), 7-deaza-8-substituted guanine, 7-deaza-8-aza guanine, hypoxanthine, N2-substituted guanines (e.g. N2-methyl-guanine), 5-amino-3-methyl-3H,6H-thiazolo[4,5-d]pyrimidine-2,7-dione, 2,6-diaminopurine, 2-aminopurine, purine, indole, adenine, substituted adenines (e.g. N6-methyl-adenine, 8-oxo-adenine) 8-substituted guanine (e.g. 8-hydroxyguanine and 8-bromoguanine), and 6-thioguanine. In another embodiment of the invention, the base is substituted by a universal base (e.g. 4-methyl-indole, 5-nitro-indole, 3-nitropyrrole, P-base, and K-base), an aromatic ring system (e.g. benzimidazole or dichloro-benzimidazole, 1-methyl-1H-[1,2,4]triazole-3-carboxylic acid amide) an aromatic ring system (e.g. fluorobenzene or difluorobenzene) and a hydrogen atom (dSpacer). According to one embodiment of the invention the oligonucleotide is associated with a carrier linked to the 3' end of the oligonucleotide. In some embodiments, the carrier is selected from the group consisting of a microparticle, dendrimer, liposome, cationic complex, and antigen. In yet another embodiment of the invention, the ODN is administered to the subject along with an antigen. In still another embodiment the CpG immunostimulatory oligonucleotides are useful for treating subjects in combination with the administration of a therapeutic protocol to the subject. In some embodiments of the invention, the therapeutic protocol is surgery.

In some embodiments the oligonucleotide is not associated with a carrier. In other embodiments the oligonucleotide is in a multimerized complex. Optionally the multimerized complex includes the oligonucleotide linked by a multimerization unit to a second oligonucleotide. The second oligonucleotide may have the formula 5'-$X_1$YR$M_1$-3'.

In one aspect the immunostimulatory oligonucleotide of the invention has the general formula 5'-$X_2$YR$M_2$-3' with a multimerization unit linked to the 3' end of the oligonucleotide. $X_2$ is a nucleic acid that consists of a single nucleotide, or a dinucleotide or a trinucleotide that does not comprise a CG dinucleotide. Y is a cytosine or a modified cytosine. R is a guanine or a modified guanine. $M_2$ is a nucleic acid of 0-27 nucleotides. In some embodiments the immunostimulatory oligonucleotides have the following structures: 5'-TCG-3', 5'-TCGT-3', 5'-UCG-3', 5'-UCGT-3'. In yet another embodiment $M_2$ is free of a CG dinucleotide. According to another embodiment of the invention $X_2$ is a single nucleotide, and $X_2$ is a pyrimidine. According to other embodiments of the invention, the internucleotide linkages of the oligonucleotide are all stabilized phosphodiester internucleotide linkages.

In some embodiments the multimerization unit is a carrier selected from the group consisting of a microparticle, dendrimer, liposome, cationic complex, cholesterol and antigen. In other embodiments the multimerization unit is a linker between the 3' end of the oligonucleotide and a second oligonucleotide.

In yet another embodiment of the invention, the ODN is administered to the subject along with an antigen. In still another embodiment the CpG immunostimulatory oligonucleotides are useful for treating subjects in combination with the administration of a therapeutic protocol to the subject. In some embodiments of the invention, the therapeutic protocol is surgery.

According to another aspect of the invention the immunostimulatory oligonucleotide has the general formula 5'-$X_3$CG$M_3$-3', wherein $X_3$ is a single nucleotide that does not comprise a CG dinucleotide; $M_3$ is a nucleic acid of 3-27 nucleotides that is free of a CG dinucleotide, and $M_3$ has at least one of the following properties: is free of a TC dinucleotide, is at least 30% T nucleotides, consists of A, T, and G or is free of a CCTTCC hexamer having at least one modified internucleotide linkage. In some embodiments $M_3$ has at least 35%, 40%, 45%, 50%, 55%, 60%, 65%, 70%, 75%, 80%, 85%, 90%, 95% or 100% T or modified versions thereof.

In another aspect the immunostimulatory oligonucleotide has the general formula 5'-$X_4$CG$M_4$-3', wherein $X_4$ is a dinucleotide that does not comprise a CG dinucleotide, and $M_4$ is a nucleic acid of 2-26 nucleotides that is free of a CG dinucleotide and it has at least one of the following properties: is free of a TG or a GT dinucleotide, is at least 38% T nucleotides or consists of A and T. In some embodiments $M_4$ has at least 40%, 45%, 50%, 55%, 60%, 65%, 70%, 75%, 80%, 85%, 90%, 95% or 100% A or T or modified versions thereof.

In yet another aspect the immunostimulatory oligonucleotide has the general formula 5'-$X_5$CG$M_5$-3', $X_5$ is a trinucleotide that does not comprise a CG dinucleotide; $M_5$ is a nucleic acid of 1-25 nucleotides that is free of a CG dinucleotide, and wherein $M_5$ has at least one of the following properties: is free of a CT dinucleotide and does not include at least one phosphorothioate linkage, is at least 41% T nucleotides, or consists of A and C. In some embodiments $M_4$ has at least 45%, 50%, 55%, 60%, 65%, 70%, 75%, 80%, 85%, 90%, 95% or 100% T or modified versions thereof.

According to another aspect of the invention the immunostimulatory oligonucleotide has the general formula 5'-TTG$M_6$-3', $M_6$ is a nucleic acid that consists of 5-21 nucleotides, wherein $M_6$ does not comprise a CG dinucleotide, wherein $M_6$ is comprised of at least 30% T nucleotides, and wherein said nucleotide is 10-24 nucleotides in length. In some embodiments $M_4$ has at least 35%, 40%, 45%, 50%, 55%, 60%, 65%, 70%, 75%, 80%, 85%, 90%, 95% or 100% T or modified versions thereof.

In some embodiments the oligonucleotide has one of the following structures:

```
5'-T*C*G*T*T*T*T*T*T*T*T*T*T-3'      (SEQ. ID NO.: 32)

5'-T*T*C*G*T*T*T*T*T*T*T*T*T*      (SEQ. ID NO.: 27)
T*T*T-3'

5'-T*T*T*C*G*T*T*T*T*T*T*T*T*      (SEQ. ID NO.: 28)
T*T*T-3'.
```

The symbol * refers to the presence of a stabilized internucleotide linkage and _: refers to the presence of a phosphodiester linkage.

An oligonucleotide comprising: 5'-$X_6$CG$M_7$-3' is provided according to an aspect of the invention. 5' designates the 5' end of the oligonucleotide and 3' designates the 3' end of the oligonucleotide. $X_6$ is 1-3 nucleotides and does not include a CG dinucleotide. $M_7$ is a nucleic acid of 6-27 nucleotides and includes at least three CG dinucleotides and is at least 50% T nucleotides. In one embodiment $M_7$ is 16-18 nucleotides in length.

In some embodiments $M_7$ includes at least four CG dinucleotides. In other embodiments at least one CG dinucleotide includes a phosphodiester internucleotide linkage. Optionally at least three CG dinucleotides includes a phosphodiester internucleotide linkage. The oligonucleotide may be selected from the group consisting of SEQ ID NO. 33, 34, 35, 36, and 37.

In another aspect the invention is an oligonucleotide comprising: 5'-'TTG$M_8$-3' wherein 5' designates the 5' end of the oligonucleotide and 3' designates the 3' end of the oligonucleotide, wherein $M_7$ is a nucleic acid of 6-18 nucleotides and includes at least one CG dinucleotide and is at least 50% T nucleotides. Optionally $M_8$ is 14 nucleotides in length.

The immunostimulatory oligonucleotides generally have a length in the range of between 3 and 35 nucleotides. In some embodiments the length is in the range of 4-6, 3-32, 6-30, or 10-24 nucleotides or any integer range therebetween.

According to one embodiment the oligonucleotide includes at least 1 modified internucleotide linkage. In other embodiments the oligonucleotide includes at least 50% modified internucleotide linkages. Optionally all internucleotide linkages of the oligonucleotide are modified. The stabilized internucleotide linkage may be a phosphorothioate linkage.

In another aspect, the invention relates to a method for treating allergy or asthma. The method is performed by administering to a subject having or at risk of having allergy or asthma an immunostimulatory CpG oligonucleotide described herein in an effective amount to treat allergy or asthma. In one embodiment the oligonucleotide is administered to a mucosal surface, such as a respiratory tissue. In other embodiments the oligonucleotide is administered in an aerosol formulation. Optionally the oligonucleotide is administered intranasally. In other embodiments the subject has or is at risk of developing allergic asthma.

A method for inducing cytokine production is provided according to another aspect of the invention. The method is performed by administering to a subject an immunostimulatory CpG oligonucleotide described herein in an effective amount to induce a cytokine selected from the group consisting of IP10, IL6, IL 8, IL12, IL18, TNF, IFN-α, chemokines, and IFN-γ.

In another aspect the invention is a composition of the CpG immunostimulatory oligonucleotides described herein in combination with an antigen or other therapeutic compound, such as an anti-microbial agent or an anti-cancer agent. The anti-microbial agent may be, for instance, an anti-viral agent, an anti-parasitic agent, an anti-bacterial agent or an anti-fungal agent.

The composition may optionally include a pharmaceutical carrier and/or be formulated in a delivery device. In some embodiments the delivery device is selected from the group consisting of cationic lipids, cell permeating proteins, and sustained release devices. In one embodiment the sustained release device is a biodegradable polymer or a microparticle.

According to another aspect of the invention a method of stimulating an immune response is provided. The method involves administering a CpG immunostimulatory oligonucleotide to a subject in an amount effective to induce an immune response in the subject. Preferably the CpG immunostimulatory oligonucleotide is administered orally, locally, in a sustained release device, mucosally, systemically, parenterally, or intramuscularly. When the CpG immunostimulatory oligonucleotide is administered to the mucosal surface it may be delivered in an amount effective for inducing a mucosal immune response or a systemic immune response. In preferred embodiments the mucosal surface is an oral, nasal, rectal, vaginal, or ocular surface.

In some embodiments the method includes exposing the subject to an antigen wherein the immune response is an antigen-specific immune response. In some embodiments the antigen is selected from the group consisting of a tumor antigen, a viral antigen, a bacterial antigen, a parasitic antigen and a peptide antigen.

CpG immunostimulatory oligonucleotides are capable of provoking a broad spectrum of immune response. For instance these CpG immunostimulatory oligonucleotides can be used to redirect a Th2 to a Th1 immune response. CpG immunostimulatory oligonucleotides may also be used to activate an immune cell, such as a lymphocyte (e.g., B and T cells), a dendritic cell, and an NK cell. The activation can be performed in vivo, in vitro, or ex vivo, i.e., by isolating an immune cell from the subject, contacting the immune cell with an effective amount to activate the immune cell of the CpG immunostimulatory oligonucleotide and re-administering the activated immune cell to the subject. In some embodiments the dendritic cell presents a cancer antigen. The dendritic cell can be exposed to the cancer antigen ex vivo.

The immune response produced by CpG immunostimulatory oligonucleotides may also result in induction of cytokine production, e.g., production of IP10, IL6, IL 8, IL12, IL18, TNF, IFN-α, chemokines, and IFN-γ.

In still another embodiment, the CpG immunostimulatory oligonucleotides are useful for treating cancer in a subject having or at risk of developing a cancer. The cancer may be selected from the group consisting of biliary tract cancer, breast cancer, cervical cancer, choriocarcinoma, colon cancer, endometrial cancer, gastric cancer, intraepithelial neoplasms, lymphomas, liver cancer, lung cancer (e.g. small cell and non-small cell), melanoma, neuroblastomas, oral cancer, ovarian cancer, pancreatic cancer, prostate cancer, rectal cancer, sarcomas, thyroid cancer, and renal cancer, as well as other carcinomas and sarcomas. In some important embodiments, the cancer is selected from the group consisting of bone cancer, brain and CNS cancer, connective tissue cancer, esophageal cancer, eye cancer, Hodgkin's lymphoma, larynx cancer, oral cavity cancer, skin cancer, and testicular cancer.

CpG immunostimulatory oligonucleotides may also be used for increasing the responsiveness of a cancer cell to a cancer therapy (i.e., an anti-cancer therapy), optionally when the CpG immunostimulatory oligonucleotide is administered in conjunction with an anti-cancer therapy. The anti-cancer therapy may be, for instance, a chemotherapy, a vaccine (e.g., an in vitro primed dendritic cell vaccine or a cancer antigen vaccine) or an immunotherapeutic agent such as an antibody based therapy. This latter therapy may also involve administering an antibody specific for a cell surface antigen of, for example, a cancer cell, wherein the immune response results in antibody dependent cellular cytotoxicity (ADCC). In one embodiment, the antibody may be selected from the group consisting of Ributaxin, Herceptin, Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260, ANA Ab, SMART 1D10 Ab, SMART ABL 364 Ab and ImmuRAIT-CEA.

Thus, according to some aspects of the invention, a subject having cancer or at risk of having a cancer is administered a CpG immunostimulatory oligonucleotide and an anti-cancer therapy. In some embodiments, the anti-cancer therapy is selected from the group consisting of a chemotherapeutic agent, an immunotherapeutic agent and a cancer vaccine.

In still another embodiment of the methods directed to treating cancer, the subject may be further administered interferon-α.

In other aspects, the invention is a method for inducing an innate immune response by administering to the subject a CpG immunostimulatory oligonucleotide in an amount effective for activating an innate immune response.

According to another aspect of the invention a method for treating a viral or retroviral infection is provided. The method involves administering to a subject having or at risk of having a viral or retroviral infection, an effective amount for treating the viral or retroviral infection of any of the compositions of the invention. In some embodiments the virus is caused by a hepatitis virus e.g., hepatitis B, hepatitis C, HIV, herpes virus, or papillomavirus.

A method for treating a bacterial infection is provided according to another aspect of the invention. The method involves administering to a subject having or at risk of having a bacterial infection, an effective amount for treating the bacterial infection of any of the compositions of the invention. In one embodiment the bacterial infection is due to an intracellular bacteria.

In another aspect the invention is a method for treating a parasite infection by administering to a subject having or at risk of having a parasite infection, an effective amount for treating the parasite infection of any of the compositions of the invention. In one embodiment the parasite infection is due to an intracellular parasite. In another embodiment the parasite infection is due to a non-helminthic parasite.

In some embodiments the subject is a human and in other embodiments the subject is a non-human vertebrate such as a dog, cat, horse, cow, pig, turkey, goat, fish, monkey, chicken, rat, mouse, or sheep.

In another aspect the invention relates to a method for inducing a TH1 immune response by administering to a subject any of the compositions of the invention in an effective amount to produce a TH1 immune response.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE DRAWINGS

The present invention may be more easily and completely understood when taken in conjunction with the accompanying figures.

DETAILED DESCRIPTION

Figure 1:
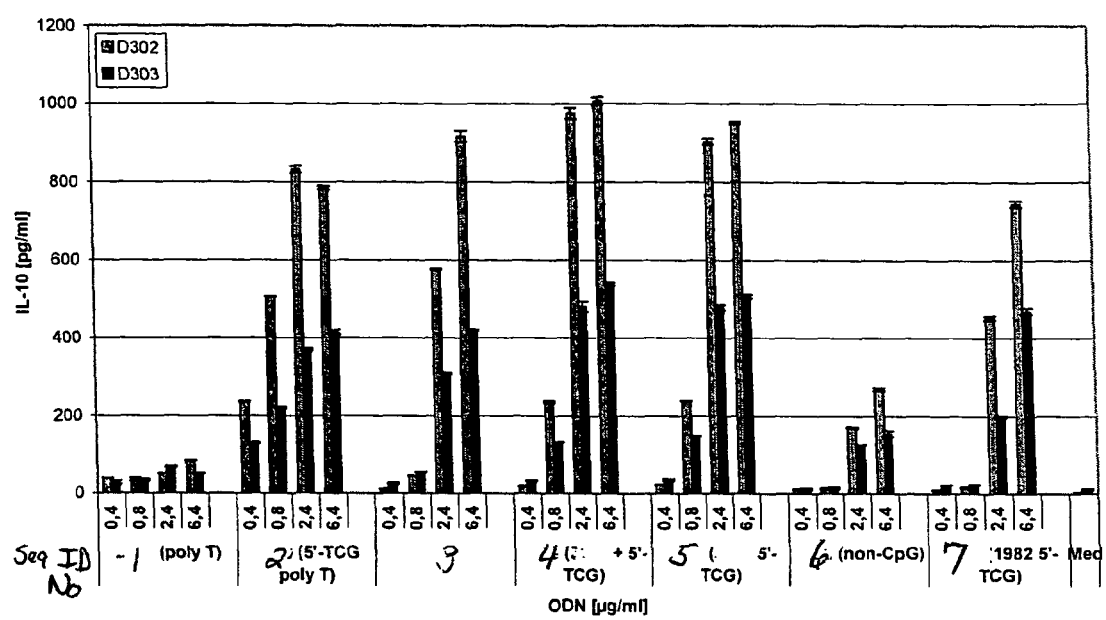
FIG. 1 is a bar graph depicting the effect of a 5'-TCG motif on the immunostimulatory activity of non-CpG or CpG ODNs through induction of IL-10.

The invention in one aspect involves the finding that specific sub-classes of CpG immunostimulatory oligonucleotides having a 5'TCG are highly effective in mediating immune stimulatory effects. These CpG nucleic acids are useful therapeutically and prophylactically for stimulating the immune system to treat cancer, infectious diseases, allergy, asthma and other disorders and to help protect against opportunistic infections following cancer chemotherapy. The strong yet balanced, cellular and humoral immune responses that result from CpG stimulation reflect the body's own natural defense system against invading pathogens and cancerous cells.

The invention involves, in one aspect, the discovery that a subset of CpG immunostimulatory oligonucleotides have improved immune stimulatory properties. The preferred CpG immunostimulatory oligonucleotides fall within one of the following 5 general formulas: 5'TCGX$_1$X$_2$N$_1$3', 5'TCGTN$_1$3', 5'TCGAN$_1$3', 5'TCGN$_1$3' and 5'TYZN$_1$3' (SEQ. ID NO.: 61-69). X$_1$ and X$_2$ refer to single nucleotides.

The formulas define subsets of the class of CpG oligonucleotides which demonstrated excellent immune stimulating properties and yet do not include additional unmethylated CpG motifs. In the formulas 5' refers to the free 5' end of the oligonucleotide and 3' refers to the free 3' end of the oligonucleotide.

N$_1$ encompasses a variable set of nucleotide sequences. The nucleotide sequences may range from 2-97 nucleotides in length or any integer range therebetween. The findings of the invention are based in part on the discovery of the importance of the positional effects of CpG or YpZ motif. It has been discovered that oligonucleotides having a 5'TCG or 5' TYZ without any additional unmethylated CpG motifs therein are strong immunostimulatory capability. The remainder of the oligonucleotide may be any combination of nucleotides or modified nucleotides as long as the 5' end of the molecule includes the requisite motif.

It has also been discovered that some sequences of N$_1$, when combined with the 5'TCG or 5' TYZ produce molecules having even greater immunostimulatory activity. For instance, when N$_1$ is at least 50% pyrimidine the oligonucleotide produces enhanced Th1 biased immune induction. In some embodiments N$_1$ is at least 55%, 60%, 65%, 70%, 75%, 80%, 85%, 90%, 95%, or 100 pyrimidine, e.g. C or T. A pyrimidine is T or C or modified versions thereof. In some embodiments the 3' most nucleotides of N$_1$ are pyrimidines. For instance the 3' end may be TTTTT, TTTT, TTT, TT, T, CCCCC, CCCC, CCC, CC, C, CTT, CCTT, or any other possible combination of pyrimidines. In some limited embodiments N$_1$ is free of a C$_{12}$ (5'-CCCCCCCCCCCC-3' (SEQ. ID NO.: 65)).

The invention involves, in one aspect, the discovery that the 5' sequence of immunostimulatory nucleotides, their length and internucleotide linkage have specific influences on the cytokine profile of the induced immune response and that these discoveries can be used to design a subset of CpG immunostimulatory oligonucleotides that have improved immune stimulatory properties. The preferred CpG immunostimulatory oligonucleotides fall within one of the following 6 general formulas: 5'-X$_1$YRM$_1$-3', 5'-X$_2$CGM$_2$-3', 5'-X$_3$CGM$_3$-3', 5'-X$_4$CGM$_4$-3', 5'-X$_5$CGM$_5$-3' and 5'-TTGM$_6$-3'.

The formulas define subsets of the class of CpG oligonucleotides which demonstrated excellent immune stimulating properties and yet do not include additional unmethylated CpG motifs. In the formulas 5' refers to the free 5' end of the oligonucleotide and 3' refers to the free 3' end of the oligonucleotide.

In the preferred embodiment with the general formula 5'-X$_1$YRM$_1$-3', X$_1$ is a single nucleotide; Y is a cytosine or a modified cytosine; R is a guanine or a modified guanine; and M$_1$ is a nucleic acid of 1-3 nucleotides. For example, such a oligonucleotide can be In the preferred embodiment with the general formula 5'-X$_2$CGM$_2$-3', X$_2$ is a nucleic acid that consists of a single nucleotide, or a dinucleotide or a trinucleotide that does not comprise a CG dinucleotide; and M$_2$ is a nucleic acid of 0-27 nucleotides. In some embodiments the oligonucleotides have the following structures: 5'-TCG-3', 5'-TCGT-3', 5'-UCG-3', 5'-UCGT-3'. In other preferred embodiments M$_2$ is free of a CG dinucleotide.

In the preferred embodiment with the general formula 5'-X$_3$CGM$_3$-3', X$_3$ is a single nucleotide that does not comprise a CG dinucleotide; M$_3$ is a nucleic acid of 3-27 nucleotides that is free of a CG dinucleotide, and M$_3$ has at least one of the following properties: is free of a TC dinucleotide, is at least 30% T nucleotides, consists of A, T, and G or is free of a CCTTCC hexamer having at least one modified internucleotide linkage. In some embodiments M$_3$ has at least 35%, 40%, 45%, 50%, 55%, 60%, 65%, 70%, 75%, 80%, 85%, 90%, 95% or 100% T or modified versions thereof.

In the preferred embodiment with the general formula 5'-X$_4$CGM$_4$-3', X$_4$ is a dinucleotide that does not comprise a CG dinucleotide, and M$_4$ is a nucleic acid of 2-26 nucleotides that is free of a CG dinucleotide and it has at least one of the following properties: is free of a TG or a GT dinucleotide, is at least 38% T nucleotides or consists of A and T. In some embodiments M$_4$ has at least 40%, 45%, 50%, 55%, 60%, 65%, 70%, 75%, 80%, 85%, 90%, 95% or 100% A or T or modified versions thereof.

In the preferred embodiment with the general formula 5'-X$_5$CGM$_5$-3', X$_5$ is a trinucleotide that does not comprise a CG dinucleotide; M$_5$ is a nucleic acid of 1-25 nucleotides that is free of a CG dinucleotide, and wherein M$_5$ has at least one of the following properties: is free of a CT dinucleotide and does not include at least one phosphorothioate linkage, is at least 41% T nucleotides, or consists of A and C. In some embodiments M$_4$ has at least 45%, 50%, 55%, 60%, 65%, 70%, 75%, 80%, 85%, 90%, 95% or 100% T or modified versions thereof.

In the preferred embodiment with the general formula 5'-TTGM$_6$-3', M$_6$ is a nucleic acid that consists of 5-21 nucleotides, wherein M$_6$ does not comprise a CG dinucleotide, wherein M$_6$ is comprised of at least 30% T nucleotides, and wherein said nucleotide is 10-24 nucleotides in length. In some embodiments M$_4$ has at least 35%, 40%, 45%, 50%, 55%, 60%, 65%, 70%, 75%, 80%, 85%, 90%, 95% or 100% T or modified versions thereof.

In some embodiment the oligonucleotide has one of the following structures:

```
5'-T*C*G*T*T*T*T*T*T*T*T*T*T-3'      (SEQ. ID NO.: 32)

5'-T*T*T*C*G*T*T*T*T*T*T*T*T*T*      (SEQ. ID NO.: 27)

T*T*T-3'

5'-T*T*T*T*C*G*T*T*T*T*T*T*T*T*      (SEQ. ID NO.: 28)

T*T*T-3'.
```

The symbol * refers to the presence of a stabilized internucleotide linkage and refers to the presence of a phosphodiester linkage.

The oligonucleotides may have one or two accessible 5' ends. Since the importance of the 5'TCG and 5'TYZ motif has been discovered, it also possible to create modified oligonucleotides having two such 5' ends. This may be achieved, for instance by attaching two oligonucleotides through a 3'-3' linkage to generate an oligonucleotide having one or two accessible 5' ends. Such a structure might have a formula such as 5'TCGN$_1$-N$_1$GCT5' (SEQ. ID NO.: 13). The 3'3'-linkage may be a phosphodiester, phosphorothioate or any other modified internucleoside bridge. Methods for accomplishing such linkages are known in the art. For instance, such linkages have been described in Seliger, H.; et al., Oligonucleotide analogs with terminal 3'-3'- and 5'-5'-internucleotidic linkages as antisense inhibitors of viral gene expression, Nucleosides & Nucleotides (1991), 10(1-3), 469-77 and Jiang, et al., Pseudo-cyclic oligonucleotides: in vitro and in vivo properties, Bioorganic & Medicinal Chemistry (1999), 7(12), 2727-2735.

Additionally, 3'3'-linked ODNs where the linkage between the 3'-terminal nucleosides is not a phosphodiester, phosphorothioate or other modified bridge, can be prepared using an additional spacer, such as tri- or tetra-ethylenglycol phosphate moiety (Durand, M. et al, Triple-helix formation by an oligonucleotide containing one (dA)12 and two (dT)12 sequences bridged by two hexaethylene glycol chains, Biochemistry (1992), 31(38), 9197-204, U.S. Pat. Nos. 5,658, 738, and 5,668,265). Alternatively, the non-nucleotidic linker may be derived from ethanediol, propanediol, or from an abasic deoxyribose (dSpacer) unit (Fontanel, Marie Laurence et al., Sterical recognition by T4 polynucleotide kinase of non-nucleosidic moieties 5'-attached to oligonucleotides; Nucleic Acids Research (1994), 22(11), 2022-7) using standard phosphoramidite chemistry. The non-nucleotidic linkers can be incorporated once or multiple times, or combined with each other allowing for any desirable distance between the 3'-ends of the two ODNs to be linked.

The oligonucleotide in some embodiments does not include an unmethylated CG motif, other than the 5'TCG.

In some embodiment the oligonucleotide has one of the following structures: 5'

```
T*C*G*A*G*G*A*C*T*T*C*T*C*T*C*A*  (SEQ. ID NO.: 50)
G*G*T*T,

T*C*G*C*C*C*C*C*C*C*C*C*C*C*C*  (SEQ. ID NO.: 51)
C,

T*C*G*T*T*T*T*T*T*T*T*T*T*T*T*  (SEQ. ID NO.: 13)
T*T*T*T*T,

T*C*G*U*U*U*U*U*U*U*U*U*U*U*U*  (SEQ. ID NO.: 48)
U,

T*C_G*T*T*T*T*T*T*T*T*T*T*T*T*  (SEQ. ID NO.: 25)
T,

T*C*G*T*T*T*T*T*T*T*T*T*T*T*T*  (SEQ. ID NO.: 14)
T3'.
```

The symbol * refers to the presence of a stabilized internucleotide linkage and _: refers to the presence of a phosphodiester linkage.

The immunostimulatory oligonucleotides generally have a length in the range of between 7 and 100 nucleotides. In some embodiments the length is in the range of 7-40, 13-100, 13-40, 13-30, 15-50, or 15-30 nucleotides or any integer range therebetween.

In some preferred embodiments the oligonucleotide is associated with a carrier linked to the 3' end by, but not limited to, the aforementioned linkers and methods. The carrier can be selected from but not limited to the group consisting of microparticles, dendrimers, liposomes, cationic complexes and antigens.

The terms "nucleic acid" and "oligonucleotide" are used interchangeably to mean multiple nucleotides (i.e., molecules comprising a sugar (e.g., ribose or deoxyribose) linked to a phosphate group and to an exchangeable organic base, which is either a substituted pyrimidine (e.g., cytosine (C), thymine (T) or uracil (U)) or a substituted purine (e.g., adenine (A) or guanine (G)). As used herein, the terms "nucleic acid" and "oligonucleotide" refer to oligoribonucleotides as well as oligodeoxyribonucleotides. The terms "nucleic acid" and "oligonucleotide" shall also include polynucleosides (i.e., a polynucleotide minus the phosphate) and any other organic base containing polymer. Nucleic acid molecules can be obtained from existing nucleic acid sources (e.g., genomic or cDNA), but are preferably synthetic (e.g., produced by nucleic acid synthesis).

The terms "nucleic acid" and "oligonucleotide" also encompass nucleic acids or oligonucleotides with substitutions or modifications, such as in the bases and/or sugars. For example, they include nucleic acids having backbone sugars that are covalently attached to low molecular weight organic groups other than a hydroxyl group at the 2' position and other than a phosphate group or hydroxy group at the 5' position. Thus modified nucleic acids may include a 2'-O-alkylated ribose group. In addition, modified nucleic acids may include sugars such as arabinose or 2'-fluoroarabinose instead of ribose. Thus the nucleic acids may be heterogeneous in backbone composition thereby containing any possible combination of polymer units linked together such as peptide-nucleic acids (which have an amino acid backbone with nucleic acid bases). Other examples are described in more detail below.

The immunostimulatory oligonucleotides of the instant invention can encompass various chemical modifications and substitutions, in comparison to natural RNA and DNA, involving a phosphodiester internucleoside bridge, a β-D-ribose unit and/or a natural nucleoside base (adenine, guanine, cytosine, thymine, uracil). Examples of chemical modifications are known to the skilled person and are described, for example, in Uhlmann E et al. (1990) *Chem Rev* 90:543; "Protocols for Oligonucleotides and Analogs" Synthesis and Properties & Synthesis and Analytical Techniques, S. Agrawal, Ed, Humana Press, Totowa, USA 1993; Crooke S T et al. (1996) *Annu Rev Pharmacol Toxicol* 36:107-129; and Hunziker J et al. (1995) *Mod Synth Methods* 7:331-417. An oligonucleotide according to the invention may have one or more modifications, wherein each modification is located at a particular phosphodiester internucleoside bridge and/or at a particular β-D-ribose unit and/or at a particular natural nucleoside base position in comparison to an oligonucleotide of the same sequence which is composed of natural DNA or RNA.

For example, the oligonucleotides may comprise one or more modifications and wherein each modification is independently selected from:
  a) the replacement of a phosphodiester internucleoside bridge located at the 3' and/or the 5' end of a nucleoside by a modified internucleoside bridge, b) the replacement of phosphodiester bridge located at the 3' and/or the 5' end of a nucleoside by a dephospho bridge, c) the replacement of a sugar phosphate unit from the sugar phosphate backbone by another unit, d) the replacement of a β-D-ribose unit by a modified sugar unit, and e) the replacement of a natural nucleoside base by a modified nucleoside base.

More detailed examples for the chemical modification of an oligonucleotide are as follows.

The oligonucleotides may include modified internucleotide linkages, such as those described in a or b above. These modified linkages may be partially resistant to degradation (e.g., are stabilized). A "stabilized oligonucleotide molecule" shall mean an oligonucleotide that is relatively resistant to in vivo degradation (e.g. via an exo- or endo-nuclease) resulting form such modifications. Oligonucleotides having phosphorothioate linkages, in some embodiments, may provide maximal activity and protect the oligonucleotide from degradation by intracellular exo- and endo-nucleases.

A phosphodiester internucleoside bridge located at the 3' and/or the 5' end of a nucleoside can be replaced by a modified internucleoside bridge, wherein the modified internucleoside bridge is for example selected from phosphorothioate, phosphorodithioate, $NR^1R^2$-phosphoramidate, boranophosphate, α-hydroxybenzyl phosphonate, phosphate-$(C_1-C_{21})$-O-alkyl ester, phosphate-$[(C_6-C_{12})$aryl-$(C_1-C_{21})$-O-alkyl]ester, $(C_1-C_8)$alkylphosphonate and/or $(C_6-C_{12})$arylphosphonate bridges, $(C_7-C_{12})$-α-hydroxymethyl-aryl (e.g., disclosed in WO 95/01363), wherein $(C_6-C_{12})$aryl, $(C_6-C_{20})$aryl and $(C_6-C_{14})$aryl are optionally substituted by halogen, alkyl, alkoxy, nitro, cyano, and where $R^1$ and $R^2$ are, independently of each other, hydrogen, $(C_1-C_{18})$-alkyl, $(C_6-C_{20})$-aryl, $(C_6-C_{14})$-aryl-$(C_1-C_8)$-alkyl, preferably hydrogen, $(C_1-C_8)$-alkyl, preferably $(C_1-C_4)$-alkyl and/or methoxyethyl, or $R^1$ and $R^2$ form, together with the nitrogen atom carrying them, a 5-6-membered heterocyclic ring which can additionally contain a further heteroatom from the group O, S and N.

The replacement of a phosphodiester bridge located at the 3' and/or the 5' end of a nucleoside by a dephospho bridge (dephospho bridges are described, for example, in Uhlmann E and Peyman A in "Methods in Molecular Biology", Vol. 20, "Protocols for Oligonucleotides and Analogs", S. Agrawal, Ed., Humana Press, Totowa 1993, Chapter 16, pp. 355 ff), wherein a dephospho bridge is for example selected from the dephospho bridges formacetal, 3'-thioformacetal, methylhydroxylamine, oxime, methylenedimethylhydrazo, dimethylenesulfone and/or silyl groups.

A sugar phosphate unit (i.e., a β-D-ribose and phosphodiester internucleoside bridge together forming a sugar phosphate unit) from the sugar phosphate backbone (i.e., a sugar phosphate backbone is composed of sugar phosphate units) can be replaced by another unit, wherein the other unit is for example suitable to build up a "morpholino-derivative" oligomer (as described, for example, in Stirchak E P et al. (1989) *Nucleic Acids Res* 17:6129-41), that is, e.g., the replacement by a morpholino-derivative unit; or to build up a polyamide nucleic acid ("PNA"; as described for example, in Nielsen P E et al. (1994) *Bioconjug Chem* 5:3-7), that is, e.g., the replacement by a PNA backbone unit, e.g., by 2-aminoethylglycine. The oligonucleotide may have other carbohydrate backbone modifications and replacements, such as peptide nucleic acids with phosphate groups (PHONA), locked nucleic acids (LNA), and oligonucleotides having backbone sections with alkyl linkers or amino linkers. The alkyl linker may be branched or unbranched, substituted or unsubstituted, and chirally pure or a racemic mixture.

A β-ribose unit or a β-D-2'-deoxyribose unit can be replaced by a modified sugar unit, wherein the modified sugar unit is for example selected from β-D-ribose, α-D-2'-deoxyribose, L-2'-deoxyribose, 2'-F-2'-deoxyribose, 2'-F-arabinose, 2'-O-$(C_1-C_6)$alkyl-ribose, preferably 2'-O-$(C_1-C_6)$ alkyl-ribose is 2'-O-methylribose, 2'-O-$(C_2-C_6)$alkenylribose, 2'-[O-$(C_1-C_6)$alkyl-O-$(C_1-C_6)$alkyl]-ribose, 2'-$NH_2$-2'-deoxyribose, β-D-xylofuranose, α-arabinofuranose, 2,4-dideoxy-β-D-erythro-hexo-pyranose, and carbocyclic (described, for example, in Froehler J (1992) *Am Chem Soc* 114:8320) and/or open-chain sugar analogs (described, for example, in Vandendriessche et al. (1993) *Tetrahedron* 49:7223) and/or bicyclosugar analogs (described, for example, in Tarkov M et al. (1993) *Helv Chim Acta* 76:481).

In some embodiments the sugar is 2'-O-methylribose, particularly for one or both nucleotides linked by a phosphodiester or phosphodiester-like internucleoside linkage.

Nucleic acids also include substituted purines and pyrimidines such as C-5 propyne pyrimidine and 7-deaza-7-substituted purine modified bases. Wagner R W et al. (1996) *Nat Biotechnol* 14:840-4. Purines and pyrimidines include but are not limited to adenine, cytosine, guanine, and thymine, and other naturally and non-naturally occurring nucleobases, substituted and unsubstituted aromatic moieties.

A modified base is any base which is chemically distinct from the naturally occurring bases typically found in DNA and RNA such as T, C, G, A, and U, but which share basic chemical structures with these naturally occurring bases. The modified nucleoside base may be, for example, selected from hypoxanthine, uracil, dihydrouracil, pseudouracil, 2-thiouracil, 4-thiouracil, 5-aminouracil, 5-$(C_1-C_6)$-alkyluracil, 5-$(C_2-C_6)$-alkenyluracil, 5-$(C_2-C_6)$-alkynyluracil, 5-(hydroxymethyl)uracil, 5-chlorouracil, 5-fluorouracil, 5-bromouracil, 5-hydroxycytosine, 5-$(C_1-C_6)$-alkylcytosine, 5-$(C_2-C_6)$-alkenylcytosine, 5-$(C_2-C_6)$-alkynylcytosine, 5-chlorocytosine, 5-fluorocytosine, 5-bromocytosine, $N^2$-dimethylguanine, 2,4-diamino-purine, 8-azapurine, a substituted 7-deazapurine, preferably 7-deaza-7-substituted and/or 7-deaza-8-substituted purine, 5-hydroxymethylcytosine, N4-alkylcytosine, e.g., N4-ethylcytosine, 5-hydroxydeoxycytidine, 5-hydroxymethyldeoxycytidine, N4-alkyldeoxycytidine, e.g., N4-ethyldeoxycytidine, 6-thiodeoxyguanosine, and deoxyribonucleosides of nitropyrrole, C5-propynylpyrimidine, and diaminopurine e.g., 2,6-diaminopurine, inosine, 5-methylcytosine, 2-aminopurine, 2-amino-6-chloropurine, hypoxanthine or other modifications of a natural nucleoside bases. This list is meant to be exemplary and is not to be interpreted to be limiting.

In particular formulas described herein a set of modified bases is defined. For instance the letter Y is used to refer to a nucleotide containing a cytosine or a modified cytosine. A modified cytosine as used herein is a naturally occurring or non-naturally occurring pyrimidine base analog of cytosine which can replace this base without impairing the immunostimulatory activity of the oligonucleotide. Modified cytosines include but are not limited to 5-substituted cytosines (e.g. 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g. N4-ethyl-cytosine), 5-aza-cytosine, 2-mercapto-cytosine, isocytosine, pseudo-isocytosine, cytosine analogs with condensed ring systems (e.g. N,N'-propylene cytosine or phenoxazine), and uracil and its derivatives (e.g. 5-fluorouracil, 5-bromo-uracil, 5-bromovinyl-uracil, 4-thio-uracil, 5-hydroxy-uracil, 5-propynyl-uracil). Some of the preferred cytosines include 5-methyl-cytosine, 5-fluoro-cytosine, 5-hydroxy-cytosine, 5-hydroxymethyl-cytosine, and N4-ethyl-cytosine. In another embodiment of the invention, the cytosine base is substituted by a universal base (e.g. 3-nitropyrrole, P-base), an aromatic ring system (e.g. fluorobenzene or difluorobenzene) or a hydrogen atom (dSpacer). The letter Z is used to refer to guanine or a modified guanine base. A modified guanine as used herein is a naturally occurring or non-naturally occurring purine base analog of guanine which can replace this base without impairing the immunostimulatory activity of the oligonucleotide. Modified guanines include but are not limited to 7-deazaguanine, 7-deaza-7-substituted guanine (such as 7-deaza-7-($C_2$-$C_6$)alkynylguanine), 7-deaza-8-substituted guanine, hypoxanthine, N2-substituted guanines (e.g. N2-methyl-guanine), 5-amino-3-methyl-3H,6H-thiazolo[4,5-d]pyrimidine-2,7-dione, 2,6-diaminopurine, 2-aminopurine, purine, indole, adenine, substituted adenines (e.g. N6-methyl-adenine, 8-oxo-adenine) 8-substituted guanine (e.g. 8-hydroxyguanine and 8-bromoguanine), and 6-thioguanine. In another embodiment of the invention, the guanine base is substituted by a universal base (e.g. 4-methyl-indole, 5-nitro-indole, and K-base), an aromatic ring system (e.g. benzimidazole or dichloro-benzimidazole, 1-methyl-1H-[1,2,4]triazole-3-carboxylic acid amide) or a hydrogen atom (dSpacer).

For use in the instant invention, the oligonucleotides of the invention can be synthesized de novo using any of a number of procedures well known in the art. For example, the b-cyanoethyl phosphoramidite method (Beaucage, S. L., and Caruthers, M. H., *Tet. Let.* 22:1859, 1981); nucleoside H-phosphonate method (Garegg et al., *Tet. Let.* 27:4051-4054, 1986; Froehler et al., *Nucl. Acid. Res.* 14:5399-5407, 1986; Garegg et al., *Tet. Let.* 27:4055-4058, 1986, Gaffney et al., *Tet. Let.* 29:2619-2622, 1988). These chemistries can be performed by a variety of automated nucleic acid synthesizers available in the market. These oligonucleotides are referred to as synthetic oligonucleotides. An isolated oligonucleotide generally refers to an oligonucleotide which is separated from components which it is normally associated with in nature. As an example, an isolated oligonucleotide may be one which is separated from a cell, from a nucleus, from mitochondria or from chromatin.

The immunostimulatory nucleic acid molecules of the instant invention can have phosphodiester internuclotide linkages. A phosphodiester internucleotide linkage is the type of linkage characteristic of nucleic acids found in nature. As shown in FIG. 20, the phosphodiester internucleotide linkage includes a phosphorus atom flanked by two bridging oxygen atoms and bound also by two additional oxygen atoms, one charged and the other uncharged. Phosphodiester internucleotide linkage is particularly preferred when it is important to reduce the tissue half-life of the oligonucleotide.

A phosphodiester-like internucleotide linkage is a phosphorus-containing bridging group that is chemically and/or diastereomerically similar to phosphodiester. Measures of similarity to phosphodiester include susceptibility to nuclease digestion and ability to activate RNAse H. Thus for example phosphodiester, but not phosphorothioate, oligonucleotides are susceptible to nuclease digestion, while both phosphodiester and phosphorothioate oligonucleotides activate RNAse H. In a preferred embodiment the phosphodiester-like internucleotide linkage is boranophosphate (or equivalently, boranophosphonate) linkage. U.S. Pat. Nos. 5,177,198; 5,859,231; 6,160,109; 6,207,819; Sergueev et al., (1998) *J Am Chem Soc* 120:9417-27. In another preferred embodiment the phosphodiester-like internucleotide linkage is diasteromerically pure Rp phosphorothioate. It is believed that diasteromerically pure Rp phosphorothioate is more susceptible to nuclease digestion and is better at activating RNAse H than mixed or diastereomerically pure Sp phosphorothioate. Stereoisomers of CpG oligonucleotides are the subject of co-pending U.S. patent application Ser. No. 09/361,575 filed Jul. 27, 1999, and published PCT application PCT/US99/17100 (WO 00/06588). It is to be noted that for purposes of the instant invention, the term "phosphodiester-like internucleotide linkage" specifically excludes phosphorodithioate and methylphosphonate internucleotide linkages.

The immunostimulatory nucleic acid molecules of the instant invention can have chimeric backbone. For purposes of the instant invention, a chimeric backbone refers to a partially stabilized backbone, wherein at least one internucleotide linkage is phosphodiester or phosphodiester-like, and wherein at least one other internucleotide linkage is a stabilized internucleotide linkage, wherein the at least one phosphodiester or phosphodiester-like linkage and the at least one stabilized linkage are different. Since boranophosphonate linkages have been reported to be stabilized relative to phosphodiester linkages, for purposes of the chimeric nature of the backbone, boranophosphonate linkages can be classified either as phosphodiester-like or as stabilized, depending on the context. For example, a chimeric backbone according to the instant invention could in one embodiment include at least one phosphodiester (phosphodiester or phosphodiester-like) linkage and at least one boranophosphonate (stabilized) linkage. In another embodiment a chimeric backbone according to the instant invention could include boranophosphonate (phosphodiester or phosphodiester-like) and phosphorothioate (stabilized) linkages. A "stabilized internucleotide linkage" shall mean an internucleotide linkage that is relatively resistant to in vivo degradation (e.g., via an exo- or endonuclease), compared to a phosphodiester internucleotide linkage. Preferred stabilized internucleotide linkages include, without limitation, phosphorothioate, phosphorodithioate, methylphosphonate, and methylphosphorothioate. Other stabilized internucleotide linkages include, without limitation: peptide, alkyl, dephospho, and others as described above.

Modified backbones such as phosphorothioates may be synthesized using automated techniques employing either phosphoramidate or H-phosphonate chemistries. Aryl- and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described (e.g., Uhlmann, E. and Peyman, A., *Chem. Rev.* 90:544, 1990; Goodchild, J., *Bioconjugate Chem.* 1:165, 1990).

CpG phosphorothioate oligonucleotides with strong stimulatory activity in the mouse system tend to show lower activity on human and other non-rodent immune cells. In the examples the development of a potent human CpG motif and the characterization of its effects and mechanisms of action on human PBMC, e.g., B-cells, and plasmacytoid dendritic cells is described. DNA containing these 5'TCG or 5'TYZ CpG motifs strongly stimulated human peripheral blood cells to produce IL-10, IL-6, IP-10 and IFN-α. The 5'TCG containing ODN could be further optimized by selecting ODNs of a particular length. For instance, ODNs of 22 nucleotides in length are more stimulatory than shorter ODN.

It has been discovered according to the invention that the subsets of CpG immunostimulatory oligonucleotides have dramatic immune stimulatory effects on human cells such as PBMC, suggesting that these CpG immunostimulatory oligonucleotides are effective therapeutic agents for human vaccination, cancer immunotherapy, asthma immunotherapy, general enhancement of immune function, enhancement of hematopoietic recovery following radiation or chemotherapy, and other immune modulatory applications.

As used herein, the terms treat, treated, or treating when used with respect to a disorder such as an infectious disease, cancer, allergy, or asthma refers to a prophylactic treatment which increases the resistance of a subject to development of the disease (e.g., to infection with a pathogen) or, in other words, decreases the likelihood that the subject will develop the disease (e.g., become infected with the pathogen) as well as a treatment after the subject has developed the disease in order to fight the disease (e.g., reduce or eliminate the infection) or prevent the disease from becoming worse.

Thus the CpG immunostimulatory oligonucleotides are useful in some aspects of the invention as a vaccine for the treatment of a subject having or at risk of developing allergy or asthma, an infection with an infectious organism or a cancer in which a specific cancer antigen has been identified. The CpG immunostimulatory oligonucleotides can also be given alone without the antigen or allergen for protection against infection, allergy or cancer or may be administered with other therapeutic agents. Repeated doses may allow longer term protection. A subject at risk as used herein is a subject who has any risk of exposure to an infection causing pathogen or a cancer or an allergen or a risk of developing cancer. For instance, a subject at risk may be a subject who is planning to travel to an area where a particular type of infectious agent is found or it may be a subject who through lifestyle or medical procedures is exposed to bodily fluids which may contain infectious organisms or directly to the organism or even any subject living in an area where an infectious organism or an allergen has been identified. Subjects at risk of developing infection also include general populations to which a medical agency recommends vaccination with a particular infectious organism antigen. If the antigen is an allergen and the subject develops allergic responses to that particular antigen and the subject may be exposed to the antigen, i.e., during pollen season, then that subject is at risk of exposure to the antigen. A subject at risk of developing an allergy to asthma includes those subjects that have been identified as having an allergy or asthma but that don't have the active disease during the CpG immunostimulatory oligonucleotide treatment as well as subjects that are considered to be at risk of developing these diseases because of genetic or environmental factors.

A subject at risk of developing a cancer is one who has a high probability of developing cancer. These subjects include, for instance, subjects having a genetic abnormality, the presence of which has been demonstrated to have a correlative relation to a higher likelihood of developing a cancer and subjects exposed to cancer causing agents such as tobacco, asbestos, or other chemical toxins, or a subject who has previously been treated for cancer and is in apparent remission. When a subject at risk of developing a cancer is treated with a CpG immunostimulatory oligonucleotide and optionally an antigen specific for the type of cancer to which the subject is at risk of developing, the subject may be able to kill the cancer cells as they develop. If a tumor begins to form in the subject, the subject will develop an innate immune response or a specific immune response against the tumor antigen.

In addition to the use of the CpG immunostimulatory oligonucleotides for prophylactic treatment, the invention also encompasses the use of the CpG immunostimulatory oligonucleotides for the treatment of a subject having an infection, an allergy, asthma, or a cancer.

A subject having an infection is a subject that has been exposed to an infectious pathogen and has acute or chronic detectable levels of the pathogen in the body. The CpG immunostimulatory oligonucleotides can be used with or without an antigen or other therapeutic to mount an innate or an antigen specific systemic or mucosal immune response that is capable of reducing the level of or eradicating the infectious pathogen. An infectious disease, as used herein, is a disease arising from the presence of a foreign microorganism in the body. It is particularly important to develop effective vaccine strategies and treatments to protect the body's mucosal surfaces, which are the primary site of pathogenic entry.

A subject having an allergy is a subject that is capable of developing an allergic reaction in response to an allergen. An allergy refers to acquired hypersensitivity to a substance (allergen). Allergic conditions include but are not limited to eczema, allergic rhinitis or coryza, hay fever, conjunctivitis, bronchial asthma, allergic asthma, urticaria (hives) and food allergies, and other atopic conditions.

Allergies are generally caused by IgE antibody generation against harmless allergens. The cytokines that are induced by systemic or mucosal administration of CpG immunostimulatory oligonucleotides are predominantly of a class called Th1 (examples are IL-12, IP-10, IFN-α and IFN-γ) and these induce both humoral and cellular immune responses. The other major type of immune response, which is associated with the production of IL-4 and IL-5 cytokines, is termed a Th2 immune response. In general, it appears that allergic diseases are mediated by Th2 type immune responses. Based on the ability of the CpG immunostimulatory oligonucleotides described herein to shift the immune response in a subject from a predominant Th2 (which is associated with production of IgE antibodies and allergy) to a balanced Th2/Th1 response (which is protective against allergic reactions), an effective dose for inducing an immune response of a CpG immunostimulatory oligonucleotide can be administered to a subject to treat asthma and allergy.

Thus, the CpG immunostimulatory oligonucleotides have significant therapeutic utility in the treatment of allergic conditions and asthma. Th2 cytokines, especially IL-4 and IL-5 are elevated in the airways of asthmatic subjects. These cytokines promote important aspects of the asthmatic inflammatory response, including IgE isotype switching, eosinophil chemotaxis and activation and mast cell growth. Th1 cytokines, especially IFN-γ and IL-12, can suppress the formation of Th2 clones and production of Th2 cytokines. Asthma refers to a disorder of the respiratory system characterized by inflammation, narrowing of the airways and increased reactivity of the airways to inhaled agents. Asthma is frequently, although not exclusively associated with atopic or allergic symptoms. Thus, asthma includes allergic asthma and nonallergic asthma.

A subject having a cancer is a subject that has detectable cancerous cells. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas. In one embodiment the cancer is hairy cell leukemia, chronic myelogenous leukemia, cutaneous T-cell leukemia, multiple myeloma, follicular lymphoma, malignant melanoma, squamous cell carcinoma, renal cell carcinoma, prostate carcinoma, bladder cell carcinoma, or colon carcinoma, CNS cancer, connective tissue cancer, esophageal cancer, eye cancer, Hodgkin's lymphoma, larynx cancer, oral cavity cancer, skin cancer, and testicular cancer, as well as other carcinomas and sarcomas.

A subject shall mean a human or vertebrate animal including but not limited to a dog, cat, horse, cow, pig, sheep, goat, turkey, chicken, primate, e.g., monkey, and fish (aquaculture species), e.g. salmon. Thus, the compounds may be used to treat cancer and tumors, infections, and allergy/asthma in human and non human subjects. Cancer is one of the leading causes of death in companion animals (i.e., cats and dogs).

In the instances when the CpG oligonucleotide is administered with an antigen, the subject may be exposed to the antigen. As used herein, the term exposed to refers to either the active step of contacting the subject with an antigen or the passive exposure of the subject to the antigen in vivo. Methods for the active exposure of a subject to an antigen are well-known in the art. In general, an antigen is administered directly to the subject by any means such as intravenous, intramuscular, oral, transdermal, mucosal, intranasal, intratracheal, or subcutaneous administration. The antigen can be administered systemically or locally. Methods for administering the antigen and the CpG immunostimulatory oligonucleotide are described in more detail below. A subject is passively exposed to an antigen if an antigen becomes available for exposure to the immune cells in the body. A subject may be passively exposed to an antigen, for instance, by entry of a foreign pathogen into the body or by the development of a tumor cell expressing a foreign antigen on its surface.

The methods in which a subject is passively exposed to an antigen can be particularly dependent on timing of administration of the CpG immunostimulatory oligonucleotide. For instance, in a subject at risk of developing a cancer or an infectious disease or an allergic or asthmatic response, the subject may be administered the CpG immunostimulatory oligonucleotide on a regular basis when that risk is greatest, i.e., during allergy season or after exposure to a cancer causing agent. Additionally the CpG immunostimulatory oligonucleotide may be administered to travelers before they travel to foreign lands where they are at risk of exposure to infectious agents. Likewise the CpG immunostimulatory oligonucleotide may be administered to soldiers or civilians at risk of exposure to biowarfare to induce a systemic or mucosal immune response to the antigen when and if the subject is exposed to it.

An antigen as used herein is a molecule capable of provoking an immune response. Antigens include but are not limited to cells, cell extracts, proteins, polypeptides, peptides, polysaccharides, polysaccharide conjugates, peptide and non-peptide mimics of polysaccharides and other molecules, small molecules, lipids, glycolipids, carbohydrates, viruses and viral extracts and muticellular organisms such as parasites and allergens. The term antigen broadly includes any type of molecule which is recognized by a host immune system as being foreign. Antigens include but are not limited to cancer antigens, microbial antigens, and allergens.

A cancer antigen as used herein is a compound, such as a peptide or protein, associated with a tumor or cancer cell surface and which is capable of provoking an immune response when expressed on the surface of an antigen presenting cell in the context of an MHC molecule. Cancer antigens can be prepared from cancer cells either by preparing crude extracts of cancer cells, for example, as described in Cohen, et al., 1994, *Cancer Research,* 54:1055, by partially purifying the antigens, by recombinant technology, or by de novo synthesis of known antigens. Cancer antigens include but are not limited to antigens that are recombinantly expressed, an immunogenic portion thereof, or a whole tumor or cancer cell. Such antigens can be isolated or prepared recombinantly or by any other means known in the art.

As used herein, the terms "cancer antigen" and "tumor antigen" are used interchangeably to refer to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses.

A microbial antigen as used herein is an antigen of a microorganism and includes but is not limited to virus, bacteria, parasites, and fungi. Such antigens include the intact microorganism as well as natural isolates and fragments or derivatives thereof and also synthetic compounds which are identical to or similar to natural microorganism antigens and induce an immune response specific for that microorganism. A compound is similar to a natural microorganism antigen if it induces an immune response (humoral and/or cellular) to a natural microorganism antigen. Such antigens are used routinely in the art and are well known to those of ordinary skill in the art.

Examples of viruses that have been found in humans include but are not limited to: Retroviridae (e.g. human immunodeficiency viruses, such as HIV-1 (also referred to as HTLV-III, LAV or HTLV-III/LAV, or HIV-III; and other isolates, such as HIV-LP: Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus;

Poxviridae (variola viruses, vaccinia viruses, pox viruses); and Iridoviridae (e.g. African swine fever virus); and unclassified viruses (e.g. the agent of delta hepatitis (thought to be a defective satellite of hepatitis B virus), Hepatitis C; Norwalk and related viruses, and astroviruses).

Both gram negative and gram positive bacteria serve as antigens in vertebrate animals. Such gram positive bacteria include, but are not limited to, *Pasteurella* species, *Staphylococci* species, and *Streptococcus* species. Gram negative bacteria include, but are not limited to, *Escherichia coli*, *Pseudomonas* species, and *Salmonella* species. Specific examples of infectious bacteria include but are not limited to, *Helicobacter pyloris, Borelia burgdorferi, Legionella pneumophilia, Mycobacteria* sps (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Rickettsia*, and *Actinomyces israeli*.

Examples of fungi include *Cryptococcus neoformans, Histoplasma capsulatum, Coccidioides immitis, Blastomyces dermatitidis, Chlamydia trachomatis, Candida albicans*.

Other infectious organisms (i.e., protists) include *Plasmodium* spp. such as *Plasmodium falciparum, Plasmodium malariae, Plasmodium ovale*, and *Plasmodium vivax* and *Toxoplasma gondii*. Blood-borne and/or tissues parasites include *Plasmodium* spp., *Babesia microti, Babesia divergens, Leishmania tropica, Leishmania* spp., *Leishmania braziliensis, Leishmania donovani, Trypanosoma gambiense* and *Trypanosoma rhodesiense* (African sleeping sickness), *Trypanosoma cruzi* (Chagas' disease), and *Toxoplasma gondii*.

Other medically relevant microorganisms have been described extensively in the literature, e.g., see C. G. A Thomas, *Medical Microbiology*, Bailliere Tindall, Great Britain 1983, the entire contents of which is hereby incorporated by reference.

An allergen refers to a substance (antigen) that can induce an allergic or asthmatic response in a susceptible subject. The list of allergens is enormous and can include pollens, insect venoms, animal dander dust, fungal spores and drugs (e.g. penicillin). Examples of natural, animal and plant allergens include but are not limited to proteins specific to the following genuses: *Canine* (*Canis familiaris*); *Dermatophagoides* (e.g. *Dermatophagoides farinae*); *Felis* (*Felis domesticus*); *Ambrosia* (*Ambrosia artemiisfolia*; *Lolium* (e.g. *Lolium perenne* or *Lolium multiflorum*); *Cryptomeria* (*Cryptomeria japonica*); *Alternaria* (*Alternaria alternata*); Alder; *Alnus* (*Alnus gultinoasa*); *Betula* (*Betula verrucosa*); *Quercus* (*Quercus alba*); *Olea* (*Olea europa*); *Artemisia* (*Artemisia vulgaris*); *Plantago* (e.g. *Plantago lanceolata*); *Parietaria* (e.g. *Parietaria officinalis* or *Parietaria judaica*); *Blattella* (e.g. *Blattella germanica*); *Apis*(e.g. *Apis multiflorum*); *Cupressus* (e.g. *Cupressus sempervirens, Cupressus arizonica* and *Cupressus macrocarpa*); *Juniperus* (e.g. *Juniperus sabinoides, Juniperus virginiana, Juniperus communis* and *Juniperus ashei*); *Thuya* (e.g. *Thuya orientalis*); *Chamaecyparis* (e.g. *Chamaecyparis obtusa*); *Periplaneta* (e.g. *Periplaneta americana*); *Agropyron* (e.g. *Agropyron repens*); *Secale* (e.g. *Secale cereale*); *Triticum* (e.g. *Triticum aestivum*); *Dactylis* (e.g. *Dactylis glomerata*); *Festuca* (e.g. *Festuca elatior*); *Poa* (e.g. *Poa pratensis* or *Poa compressa*); *Avena* (e.g. *Avena sativa*); *Holcus* (e.g. *Holcus lanatus*); *Anthoxanthum* (e.g. *Anthoxanthum odoratum*); *Arrhenatherum* (e.g. *Arrhenatherum elatius*); *Agrostis* (e.g. *Agrostis alba*); *Phleum* (e.g. *Phleum pratense*); *Phalaris* (e.g. *Phalaris arundinacea*); *Paspalum* (e.g. *Paspalum notatum*); *Sorghum* (e.g. *Sorghum halepensis*); and *Bromus* (e.g. *Bromus inermis*).

The antigen may be substantially purified. The term substantially purified as used herein refers to an antigen, i.e., a polypeptide which is substantially free of other proteins, lipids, carbohydrates or other materials with which it is naturally associated. One skilled in the art can purify polypeptide antigens using standard techniques for protein purification. The substantially pure polypeptide will often yield a single major band on a non-reducing polyacrylamide gel. In the case of partially glycosylated polypeptides or those that have several start codons, there may be several bands on a non-reducing polyacrylamide gel, but these will form a distinctive pattern for that polypeptide. The purity of the polypeptide antigen may also be determined by amino-terminal amino acid sequence analysis. Other types of antigens such as polysaccharides, small molecule, mimics etc are included within the invention and may optionally be substantially pure.

The oligonucleotides of the invention may be administered to a subject with an anti-microbial agent. An anti-microbial agent, as used herein, refers to a naturally-occurring or synthetic compound which is capable of killing or inhibiting infectious microorganisms. The type of anti-microbial agent useful according to the invention will depend upon the type of microorganism with which the subject is infected or at risk of becoming infected. Anti-microbial agents include but are not limited to anti-bacterial agents, anti-viral agents, anti-fungal agents and anti-parasitic agents. Phrases such as "anti-infective agent", "anti-bacterial agent", "anti-viral agent", "anti-fungal agent", "anti-parasitic agent" and "parasiticide" have well-established meanings to those of ordinary skill in the art and are defined in standard medical texts. Briefly, anti-bacterial agents kill or inhibit bacteria, and include antibiotics as well as other synthetic or natural compounds having similar functions. Antibiotics are low molecular weight molecules which are produced as secondary metabolites by cells, such as microorganisms. In general, antibiotics interfere with one or more bacterial functions or structures which are specific for the microorganism and which are not present in host cells. Anti-viral agents can be isolated from natural sources or synthesized and are useful for killing or inhibiting viruses. Anti-fungal agents are used to treat superficial fungal infections as well as opportunistic and primary systemic fungal infections. Anti-parasitic agents kill or inhibit parasites.

Examples of anti-parasitic agents, also referred to as parasiticides useful for human administration include but are not limited to albendazole, amphotericin B, benznidazole, bithionol, chloroquine HCl, chloroquine phosphate, clindamycin, dehydroemetine, diethylcarbamazine, diloxanide furoate, eflornithine, furazolidaone, glucocorticoids, halofantrine, iodoquinol, ivermectin, mebendazole, mefloquine, meglumine antimoniate, melarsoprol, metrifonate, metronidazole, niclosamide, nifurtimox, oxamniquine, paromomycin, pentamidine isethionate, piperazine, praziquantel, primaquine phosphate, proguanil, pyrantel pamoate, pyrimethanmine-sulfonamides, pyrimethanmine-sulfadoxine, quinacrine HCl, quinine sulfate, quinidine gluconate, spiramycin, stibogluconate sodium (sodium antimony gluconate), suramin, tetracycline, doxycycline, thiabendazole, tinidazole, trimethroprim-sulfamethoxazole, and tryparsamide some of which are used alone or in combination with others.

Antibacterial agents kill or inhibit the growth or function of bacteria. A large class of antibacterial agents is antibiotics. Antibiotics, which are effective for killing or inhibiting a wide range of bacteria, are referred to as broad spectrum antibiotics. Other types of antibiotics are predominantly effective against the bacteria of the class gram-positive or gram-negative. These types of antibiotics are referred to as narrow spectrum antibiotics. Other antibiotics which are effective against a single organism or disease and not against other types of bacteria, are referred to as limited spectrum antibiotics. Antibacterial agents are sometimes classified based on their primary mode of action. In general, antibacterial agents are cell wall synthesis inhibitors, cell membrane inhibitors, protein synthesis inhibitors, nucleic acid synthesis or functional inhibitors, and competitive inhibitors.

Antiviral agents are compounds which prevent infection of cells by viruses or replication of the virus within the cell. There are many fewer antiviral drugs than antibacterial drugs because the process of viral replication is so closely related to DNA replication within the host cell, that non-specific antiviral agents would often be toxic to the host. There are several stages within the process of viral infection which can be blocked or inhibited by antiviral agents. These stages include, attachment of the virus to the host cell (immunoglobulin or binding peptides), uncoating of the virus (e.g. amantadine), synthesis or translation of viral mRNA (e.g. interferon), replication of viral RNA or DNA (e.g. nucleoside analogues), maturation of new virus proteins (e.g. protease inhibitors), and budding and release of the virus.

Nucleotide analogues are synthetic compounds which are similar to nucleotides, but which have an incomplete or abnormal deoxyribose or ribose group. Once the nucleotide analogues are in the cell, they are phosphorylated, producing the triphosphate form which competes with normal nucleotides for incorporation into the viral DNA or RNA. Once the triphosphate form of the nucleotide analogue is incorporated into the growing nucleic acid chain, it causes irreversible association with the viral polymerase and thus chain termination. Nucleotide analogues include, but are not limited to, acyclovir (used for the treatment of herpes simplex virus and varicella-zoster virus), gancyclovir (useful for the treatment of cytomegalovirus), idoxuridine, ribavirin (useful for the treatment of respiratory syncitial virus), dideoxyinosine, dideoxycytidine, zidovudine (azidothymidine), imiquimod, and resimiquimod.

The interferons are cytokines which are secreted by virus-infected cells as well as immune cells. The interferons function by binding to specific receptors on cells adjacent to the infected cells, causing the change in the cell which protects it from infection by the virus. α and β-interferon also induce the expression of Class I and Class II MHC molecules on the surface of infected cells, resulting in increased antigen presentation for host immune cell recognition. α and β-interferons are available as recombinant forms and have been used for the treatment of chronic hepatitis B and C infection. At the dosages which are effective for anti-viral therapy, interferons have severe side effects such as fever, malaise and weight loss.

Anti-viral agents useful in the invention include but are not limited to immunoglobulins, amantadine, interferons, nucleoside analogues, and protease inhibitors. Specific examples of anti-virals include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

Anti-fungal agents are useful for the treatment and prevention of infective fungi. Anti-fungal agents are sometimes classified by their mechanism of action. Some anti-fungal agents function as cell wall inhibitors by inhibiting glucose synthase. These include, but are not limited to, basiungin/ECB. Other anti-fungal agents function by destabilizing membrane integrity. These include, but are not limited to, immidazoles, such as clotrimazole, sertaconzole, fluconazole, itraconazole, ketoconazole, miconazole and voriconacole, as well as FK 463, amphotericin B, BAY 38-9502, MK 991, pradimicin, UK 292, butenafine, and terbinafine. Other anti-fungal agents function by breaking down chitin (e.g. chitinase) or immunosuppression (501 cream).

CpG immunostimulatory oligonucleotides can be combined with other therapeutic agents such as adjuvants to enhance immune responses. The CpG immunostimulatory oligonucleotide and other therapeutic agent may be administered simultaneously or sequentially. When the other therapeutic agents are administered simultaneously they can be administered in the same or separate formulations, but are administered at the same time. The other therapeutic agents are administered sequentially with one another and with CpG immunostimulatory oligonucleotide, when the administration of the other therapeutic agents and the CpG immunostimulatory oligonucleotide is temporally separated. The separation in time between the administration of these compounds may be a matter of minutes or it may be longer. Other therapeutic agents include but are not limited to adjuvants, cytokines, antibodies, antigens, etc.

The compositions of the invention may also be administered with non-nucleic acid adjuvants. A non-nucleic acid adjuvant is any molecule or compound except for the CpG immunostimulatory oligonucleotides described herein which can stimulate the humoral and/or cellular immune response. Non-nucleic acid adjuvants include, for instance, adjuvants that create a depo effect, immune stimulating adjuvants, and adjuvants that create a depo effect and stimulate the immune system.

The CpG immunostimulatory oligonucleotides are also useful as mucosal adjuvants. It has previously been discovered that both systemic and mucosal immunity are induced by mucosal delivery of CpG nucleic acids. Thus, the oligonucleotides may be administered in combination with other mucosal adjuvants.

Immune responses can also be induced or augmented by the co-administration or co-linear expression of cytokines (Bueler & Mulligan, 1996; Chow et al., 1997; Geissler et al., 1997; Iwasaki et al., 1997; Kim et al., 1997) or co-stimulatory molecules such as B7 (Iwasaki et al., 1997; Tsuji et al., 1997) with the CpG immunostimulatory oligonucleotides. The term cytokine is used as a generic name for a diverse group of soluble proteins and peptides which act as humoral regulators at nano- to picomolar concentrations and which, either under normal or pathological conditions, modulate the functional activities of individual cells and tissues. These proteins also mediate interactions between cells directly and regulate processes taking place in the extracellular environment. Examples of cytokines include, but are not limited to IP-10, IL-1, IL-2, IL-4, IL-5, IL-6, IL-7, IL-10, IL-12, IL-15, IL-18, granulocyte-macrophage colony stimulating factor (GM-CSF), granulocyte colony stimulating factor (G-CSF), interferon-γ (γ-IFN), IFN-α, tumor necrosis factor (TNF), TGF-β, FLT-3 ligand, and CD40 ligand. In addition to cytokines the CpG oligonucleotides may be used in combination with antibodies against certain cytokines, such as anti-IL-10 and anti-TGF-β, as well as Cox inhibitors, i.e. COX-1 and COX-2 inhibitors.

The oligonucleotides are also useful for redirecting an immune response from a Th2 immune response to a Th1 immune response. This results in the production of a relatively balanced Th1/Th2 environment. Redirection of an immune response from a Th2 to a Th1 immune response can be assessed by measuring the levels of cytokines produced in response to the nucleic acid (e.g., by inducing monocytic cells and other cells to produce Th1 cytokines, including IL-12, IFN-γ and GM-CSF). The redirection or rebalance of the immune response from a Th2 to a Th1 response is particularly useful for the treatment of asthma. For instance, an effective amount for treating asthma can be that amount; useful for redirecting a Th2 type of immune response that is associated with asthma to a Th1 type of response or a balanced Th1/Th2 environment. Th2 cytokines, especially IL-4 and IL-5 are elevated in the airways of asthmatic subjects. The CpG immunostimulatory oligonucleotides described herein cause an increase in Th1 cytokines which helps to rebalance the immune system, preventing or reducing the adverse effects associated with a predominately Th2 immune response.

The CpG immunostimulatory oligonucleotides have the unique capability to promote cell survival, differentiation, activation and maturation of dendritic cells, and are useful for in vitro, in vivo, and ex vivo methods involving dendritic cells.

CpG immunostimulatory oligonucleotides also increase natural killer cell lytic activity and antibody dependent cellular cytotoxicity (ADCC). ADCC can be performed using a CpG immunostimulatory oligonucleotide in combination with an antibody specific for a cellular target, such as a cancer cell. When the CpG immunostimulatory oligonucleotide is administered to a subject in conjunction with the antibody the subject's immune system is induced to kill the tumor cell. The antibodies useful in the ADCC procedure include antibodies which interact with a cell in the body. Many such antibodies specific for cellular targets have been described in the art and many are commercially available.

The CpG immunostimulatory oligonucleotides may also be administered in conjunction with an anti-cancer therapy. Anti-cancer therapies include cancer medicaments, radiation and surgical procedures. As used herein, a "cancer medicament" refers to an agent which is administered to a subject for the purpose of treating a cancer. As used herein, "treating cancer" includes preventing the development of a cancer, reducing the symptoms of cancer, and/or inhibiting the growth of an established cancer. In other aspects, the cancer medicament is administered to a subject at risk of developing a cancer for the purpose of reducing the risk of developing the cancer. Various types of medicaments for the treatment of cancer are described herein. For the purpose of this specification, cancer medicaments are classified as chemotherapeutic agents, immunotherapeutic agents, cancer vaccines, hormone therapy, and biological response modifiers.

Additionally, the methods of the invention are intended to embrace the use of more than one cancer medicament along with the CpG immunostimulatory oligonucleotides. As an example, where appropriate, the CpG immunostimulatory oligonucleotides may be administered with both a chemotherapeutic agent and an immunotherapeutic agent. Alternatively, the cancer medicament may embrace an immunotherapeutic agent and a cancer vaccine, or a chemotherapeutic agent and a cancer vaccine, or a chemotherapeutic agent, an immunotherapeutic agent and a cancer vaccine all administered to one subject for the purpose of treating a subject having a cancer or at risk of developing a cancer.

The chemotherapeutic agent may be selected from the group consisting of methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS farnesyl transferase inhibitor, farnesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, ISI641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Paclitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT (Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, Iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26) and Vindesine sulfate, but it is not so limited.

The immunotherapeutic agent may be selected from the group consisting of Ributaxin, Herceptin, Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260, ANA Ab, SMART ID10 Ab, SMART ABL 364 Ab and ImmuRAIT-CEA, but it is not so limited.

The cancer vaccine may be selected from the group consisting of EGF, Anti-idiotypic cancer vaccines, Gp75 antigen, GMK melanoma vaccine, MGV ganglioside conjugate vaccine, Her2/neu, Ovarex, M-Vax, O-Vax, L-Vax, STn-KHL theratope, BLP25 (MUC-1), liposomal idiotypic vaccine, Melacine, peptide antigen vaccines, toxin/antigen vaccines, MVA-based vaccine, PACIS, BCG vacine, TA-HPV, TA-CIN, DISC-virus and ImmuCyst/TheraCys, but it is not so limited.

The use of CpG immunostimulatory oligonucleotides in conjunction with immunotherapeutic agents such as monoclonal antibodies is able to increase long-term survival through a number of mechanisms including significant enhancement of ADCC (as discussed above), activation of natural killer (NK) cells and an increase in IFNα levels. The nucleic acids when used in combination with monoclonal antibodies serve to reduce the dose of the antibody required to achieve a biological result.

The invention also includes methods for inducing antigen non-specific innate immune activation and broad spectrum resistance to infectious challenge using the CpG immunostimulatory oligonucleotides. The term innate immune activation as used herein refers to the activation of immune cells other than memory B cells and for instance can include the activation of NK cells, T cells and/or other immune cells that can respond in an antigen independent fashion. A broad spectrum resistance to infectious challenge is induced because the immune cells are in active form and are primed to respond to any invading compound or microorganism. The cells do not have to be specifically primed against a particular antigen. This is particularly useful in biowarfare, and the other circumstances described above such as travelers.

The CpG immunostimulatory oligonucleotides may be directly administered to the subject or may be administered in conjunction with a nucleic acid delivery complex. A nucleic acid delivery complex shall mean a nucleic acid molecule associated with (e.g. ionically or covalently bound to; or encapsulated within) a targeting means (e.g. a molecule that results in higher affinity binding to target cell. Examples of nucleic acid delivery complexes include nucleic acids associated with a sterol (e.g. cholesterol), a lipid (e.g. a cationic lipid, virosome or liposome), or a target cell specific binding agent (e.g. a ligand recognized by target cell specific receptor). Preferred complexes may be sufficiently stable in vivo to prevent significant uncoupling prior to internalization by the target cell. However, the complex can be cleavable under appropriate conditions within the cell so that the oligonucleotide is released in a functional form.

The CpG immunostimulatory oligonucleotide and/or the antigen and/or other therapeutics may be administered alone (e.g., in saline or buffer) or using any delivery vehicles known in the art. For instance the following delivery vehicles have been described: Cochleates (Gould-Fogerite et al., 1994, 1996); Emulsomes (Vancott et al., 1998, Lowell et al., 1997); ISCOMs (Mowat et al., 1993, Carlsson et al., 1991, Hu et., 1998, Morein et al., 1999); Liposomes (Childers et al., 1999, Michalek et al., 1989, 1992, de Haan 1995a, 1995b); Live bacterial vectors (e.g., *Salmonella, Escherichia coli, Bacillus calmatte-guerin, Shigella, Lactobacillus*) (Hone et al., 1996, Pouwels et al., 1998, Chatfield et al., 1993, Stover et al., 1991, Nugent et al., 1998); Live viral vectors (e.g., Vaccinia, adenovirus, Herpes Simplex) (Gallichan et al., 1993, 1995, Moss et al., 1996, Nugent et al., 1998, Flexner et al., 1988, Morrow et al., 1999); Microspheres (Gupta et al., 1998, Jones et al., 1996, Maloy et al., 1994, Moore et al., 1995, O'Hagan et al., 1994, Eldridge et al., 1989); Nucleic acid vaccines (Fynan et al., 1993, Kuklin et al., 1997, Sasaki et al., 1998, Okada et al., 1997, Ishii et al., 1997); Polymers (e.g. carboxymethylcellulose, chitosan) (Hamajima et al., 1998, Jabbal-Gill et al., 1998); Polymer rings (Wyatt et al., 1998); Proteosomes (Vancott et al., 1998, Lowell et al., 1988, 1996, 1997); Sodium Fluoride (Hashi et al., 1998); Transgenic plants (Tacket et al., 1998, Mason et al., 1998, Haq et al., 1995); Virosomes (Gluck et al., 1992, Mengiardi et al., 1995, Cryz et al., 1998); Virus-like particles (Jiang et al., 1999, Leibl et al., 1998). Other delivery vehicles are known in the art.

The term effective amount of a CpG immunostimulatory oligonucleotide refers to the amount necessary or sufficient to realize a desired biologic effect. For example, an effective amount of a CpG immunostimulatory oligonucleotide administered with an antigen for inducing mucosal immunity is that amount necessary to cause the development of IgA in response to an antigen upon exposure to the antigen, whereas that amount required for inducing systemic immunity is that amount necessary to cause the development of IgG in response to an antigen upon exposure to the antigen. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular CpG immunostimulatory oligonucleotide being administered the size of the subject, or the severity of the disease or condition. One of ordinary skill in the art can empirically determine the effective amount of a particular CpG immunostimulatory oligonucleotide and/or antigen and/or or other therapeutic agent without necessitating undue experimentation.

Subject doses of the compounds described herein for mucosal or local delivery typically range from about 0.1 µg to 10 mg per administration, which depending on the application could be given daily, weekly, or monthly and any other amount of time therebetween or as otherwise required. More typically mucosal or local doses range from about 10 µg to 5 mg per administration, and most typically from about 100 µg to 1 mg, with 2-4 administrations being spaced days or weeks apart. More typically, immune stimulant doses range from 1 µg to 10 mg per administration, and most typically 10 µg to 1 mg, with daily or weekly administrations. Subject doses of the compounds described herein for parenteral delivery for the purpose of inducing an antigen-specific immune response, wherein the compounds are delivered with an antigen but not another therapeutic agent are typically 5 to 10,000 times higher than the effective mucosal dose for vaccine adjuvant or immune stimulant applications, and more typically 10 to 1,000 times higher, and most typically 20 to 100 times higher. Doses of the compounds described herein for parenteral delivery for the purpose of inducing an innate immune response or for increasing ADCC or for inducing an antigen specific immune response when the CpG immunostimulatory oligonucleotides are administered in combination with other therapeutic agents or in specialized delivery vehicles typically range from about 1.0 µg to 100 mg per administration, which depending on the application could be given daily, weekly, or monthly and any other amount of time therebetween or as otherwise required. More typically parenteral doses for these purposes range from about 100 µg to 50 mg per administration, and most typically from about 200 µg to 2 mg, with 2-4 administrations being spaced days or weeks apart. In some embodiments, however, parenteral doses for these purposes may be used in a range of 5 to 10,000 times higher than the typical doses described above.

For any compound described herein the therapeutically effective amount can be initially determined from animal models. A therapeutically effective dose can also be determined from human data for other CpG oligonucleotides which have been tested in humans (human clinical trials are ongoing) and for compounds which are known to exhibit similar pharmacological activities, such as other adjuvants, e.g., LT and other antigens for vaccination purposes. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the CpG immunostimulatory oligonucleotide an/or other therapeutics can be administered to a subject by any mode that delivers the compound to the desired surface, e.g., local, mucosal, systemic. Administering the pharmaceutical composition of the present invention may be accomplished by any means known to the skilled artisan. Preferred routes of administration include but are not limited to oral, parenteral, intramuscular, intranasal, sublingual, intratracheal, inhalation, ocular, vaginal, and rectal.

For oral administration, the compounds (i.e., CpG immunostimulatory oligonucleotides, antigens and/or other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

The compounds may be administered by inhalation to pulmonary tract, especially the bronchi and more particularly into the alveoli of the deep lung, using standard inhalation devices. The compounds may be delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. An inhalation apparatus may be used to deliver the compounds to a subject. An inhalation apparatus, as used herein, is any device for administering an aerosol, such as dry powdered form of the compounds. This type of equipment is well known in the art and has been described in detail, such as that description found in Remington: The Science and Practice of Pharmacy, 19$^{th}$ Edition, 1995, Mac Publishing Company, Easton, Pa., pages 1676-1692. Many U.S. patents also describe inhalation devices, such as U.S. Pat. No. 6,116,237.

"Powder" as used herein refers to a composition that consists of finely dispersed solid particles. Preferably the compounds are relatively free flowing and capable of being dispersed in an inhalation device and subsequently inhaled by a subject so that the compounds reach the lungs to permit penetration into the alveoli. A "dry powder" refers to a powder composition that has a moisture content such that the particles are readily dispersible in an inhalation device to form an aerosol. The moisture content is generally below about 10% by weight (% w) water, and in some embodiments is below about 5% w and preferably less than about 3% w. The powder may be formulated with polymers or optionally may be formulated with other materials such as liposomes, albumin and/or other carriers.

Aerosol dosage and delivery systems may be selected for a particular therapeutic application by one of skill in the art, such as described, for example in Gonda, I. "Aerosols for delivery of therapeutic and diagnostic agents to the respiratory tract," in Critical Reviews in Therapeutic Drug Carrier Systems, 6:273-313 (1990), and in Moren, "Aerosol dosage forms and formulations," in Aerosols in Medicine. Principles, Diagnosis and Therapy, Moren, et al., Eds., Esevier, Amsterdam, 1985.

The compounds, when it is desirable to deliver them systemically, may be formulated for parenteral administration by injection, e.g., by bolus injection or continuous infusion.

Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, Science 249:1527-1533, 1990, which is incorporated herein by reference.

The CpG immunostimulatory oligonucleotides and optionally other therapeutics and/or antigens may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of a CpG immunostimulatory oligonucleotide and optionally antigens and/or other therapeutic agents optionally included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Materials and Methods:
Oligodeoxynucleotides All ODNs were provided by Coley Pharmaceutical GmbH (Langenfeld, Germany). ODNs were diluted in phosphate-buffered saline (Sigma, Germany), and stored at −20° C. All dilutions were carried out using pyrogen-free reagents. The ODNs used in the studies described below are shown in Table 1.

TABLE 1

| Sequences of ODNs shown in the drawings. | |
|---|---|
| T*T*T*T*T*T*T*T*T*T*T*T*T*T*T*T* T*T | (SEQ. ID NO.: 1) |
| T*C*G*T*T*T*T*T*T*T*T*T*T*T*T*T *T | (SEQ. ID NO.: 2) |
| T*G*A*C*T*G*T*G*A*A*C*G*T*T*C*G* A*G*A*T*G*A | (SEQ. ID NO.: 3) |
| T*C*G*T*G*A*C*T*G*T*G*A*A*C*G*T* T*C*G*A*G*A*T*G*A | (SEQ. ID NO.: 4) |
| T*C*G*C*T*G*T*G*A*A*C*G*T*T*C*G* A*G*A*T*G*A | (SEQ. ID NO.: 5) |
| T*C*C*A*G*G*A*C*T*T*C*T*C*T*C*A* G*G*T*T | (SEQ. ID NO.: 6) |

TABLE 1-continued

Sequences of ODNs shown in the drawings.

T*C*G*T*C*C*A*G*G*A*C*T*T*C*T*C* (SEQ. ID NO.: 7)
T*C*A*G*G*T*T

T*T*T*T*T*T*T*T*T*T*T*T*T*T*T*T* (SEQ. ID NO.: 8)
T

T*C*G*A*A*A*A*A*A*A*A*A*A*A*A*A* (SEQ. ID NO.: 9)
A

T*G*C*T*T*T*T*T*T*T*T*T*T*T*T*T* (SEQ. ID NO.: 10)
T

T*T*T*T*T*T*T*T*T*T*T*T*T*T*T*C* (SEQ. ID NO.: 11)
G

C*G*T*T*T*T*T*T*T*T*T*T*T*T*T*T* (SEQ. ID NO.: 12)
T

T*C*G*T*T*T*T*T*T*T*T*T*T*T*T*T* (SEQ. ID NO.: 13)
T*T*T*T*T

A*C*G*T*T*T*T*T*T*T*T*T*T*T*T*T* (SEQ. ID NO.: 14)
T

C*C*G*T*T*T*T*T*T*T*T*T*T*T*T*T* (SEQ. ID NO.: 15)
T

G*C*G*T*T*T*T*T*T*T*T*T*T*T*T*T* (SEQ. ID NO.: 16)
T

T*T*G*T*T*T*T*T*T*T*T*T*T*T*T*T* (SEQ. ID NO.: 17)
T

T*G*T*C*G*T*T*G*T*C*G*T*T*G*T*C* (SEQ. ID NO.: 18)
G*T*T*G*T*C*G*T*T

T*C*G*T*C*G*T*T*G*T*C*G*T*T*G*T* (SEQ. ID NO.: 19)
C*G*T*T*G*T*C*G*T*T

T*C*C*A*T*G*A*C*G*T*T*C*C*T*G*A* (SEQ. ID NO.: 20)
C*G*T*T

T*C*G*A*T*G*A*C*G*T*T*C*C*T*G*A* (SEQ. ID NO.: 21)
C*G*T*T

T*C*G*T*C*G*T*C*C*A*G*G*A*C*T*T* (SEQ. ID NO.: 22)
C*T*C*T*C*A*G*G*T*T

T*C*G*T*C*G*C*T*G*T*G*A*A*C*G*T* (SEQ. ID NO.: 23)
T*C*G*A*G*A*T*G*A

T*C*G*T*G*A*C*T*G*T*G*A*A*C*G*T* (SEQ. ID NO.: 24)
T*C*G*A*G*A*T*G*A

T*C_G*T*T*T*T*T*T*T*T*T*T*T*T*T* (SEQ. ID NO.: 25)
T

T*C*G*T*C*G*T*T*T*T*G*T*C*G*T*T* (SEQ. ID NO.: 26)
T*T*G*T*C*G*T*T

T*T*C*G*T*T*T*T*T*T*T*T*T*T*T*T* (SEQ. ID NO.: 27)
T

T*T*T*C*G*T*T*T*T*T*T*T*T*T*T*T* (SEQ. ID NO.: 28)
T

T*T*T*T*C*G*T*T*T*T*T*T*T*T*T*T* (SEQ. ID NO.: 29)
T

T*T*T*T*T*C*G*T*T*T*T*T*T*T*T*T* (SEQ. ID NO.: 30)
T

T*C*C*A*G*G*A*C*T*T*C*T*C*T*C*A* (SEQ. ID NO.: 31)
G*G*T*T

T*C*G*T*T*T*T*T*T*T*T*T*T (SEQ. ID NO.: 32)
T*C_G*T*C_G*T*T*T*T_G*T*C_G*T*T (SEQ. ID NO.: 33)
T*T*C_G*T*C_G*T*T*T*C_G*T*C_G*T* (SEQ. ID NO.: 34)
T

T*T*C_G*T*C_G*T*T*T*T_G*T*C_G*T* (SEQ. ID NO.: 35)
T

T*T*C*G*T*C*G*T*T*T*C*G*T*C*G*T* (SEQ. ID NO.: 36)
T

T*T*T*C_G*T*C_G*T*T*T*C_G*T*C_G*T (SEQ. ID NO.: 37)
*T

T*T*G_C*T*C_G*T*T*T*C_G*T*C_G*T*T (SEQ. ID NO.: 38)
T*T*G_C*T*G_C*T*T*T*C_G*T*C_G*T*T (SEQ. ID NO.: 39)
T*T*G_C*T*G_C*T*T*T*G_C*T*G_C*T*T (SEQ. ID NO.: 40)
T*C*G*A*A*A*A*A*A*A*A*A*T*A*A* (SEQ. ID NO.: 41)
A

T*C*G*A*A*A*A*A*A*A*A*T*T*A*A* (SEQ. ID NO.: 42)
A

T*C*G*A*A*A*A*A*A*A*T*T*T*A*A* (SEQ. ID NO.: 43)
A

T*C*G*A*A*A*A*A*T*T*T*T*T*A*A* (SEQ. ID NO.: 44)
A

T*C*G*A*A*A*A*T*T*T*T*T*T*T*T* (SEQ. ID NO.: 45)
A

T*C*G*T*A*A*A*A*A*A*A*A*A*A*A* (SEQ. ID NO.: 46)
A

T*C*G*T*T*T*A*A*A*A*A*A*A*A*A* (SEQ. ID NO.: 47)
A

TABLE 1-continued

Sequences of ODNs shown in the drawings.

T*C*G*U*U*U*U*U*U*U*U*U*U*U*U* (SEQ. ID NO.: 48)
U

U*U*U*U*U*U*U*U*U*U*U*U*U*U*U* (SEQ. ID NO.: 49)
U

T*C*G*A*G*G*A*C*T*T*C*T*C*T*C*A* (SEQ. ID NO.: 50)
G*G*T*T

T*C*G*C*C*C*C*C*C*C*C*C*C*C*C* (SEQ. ID NO.: 51)
C

T*C*G*T*C*G*A*G*C*G*T*G*C*G*C*C* (SEQ ID NO. 52)
A*T

T*C*G*C*C*C*A*G*C*G*T*G*C*G*C*C* (SEQ ID NO. 53)
A*T

U*C*G*T*T*T*T*T*T*T*T*T*T*T*T* (SEQ. ID NO.: 54)
T

T*C*U*T*T*T*T*T*T*T*T*T*T*T*T* (SEQ. ID NO.: 55)
T

T*U*G*T*T*T*T*T*T*T*T*T*T*T*T* (SEQ. ID NO.: 56)
T

T*C*G*T*T*T*T*T*T*T*T*T*T*T (SEQ ID NO. 57)

T*T*C*G*T*T*T*T*T*T*T*T*T*T*T* (SEQ ID NO. 58)
T

T*T*T*T*T*T*T*T*T*C*G*T*T*T*T*T* (SEQ ID NO. 59)
T

T*C*T*C*C*C*A*G*C*G*T*G*C*G*C*C* (SEQ ID NO. 60)
A*T

*: Phosphorothioate linkage;
_: Phosphodiester linkage.

Cell purification Peripheral blood buffy coat preparations from healthy male and female human donors were obtained from the German Red Cross (Rathingen, Germany) or from the Blood Bank of the University of Düsseldorf (Germany) and from these, PBMC were purified by centrifugation over Ficoll-Hypaque (Sigma). The purified PBMC were either used fresh (for most assays) or were suspended in freezing medium and stored at −70° C. When required, aliquots of these cells were thawed, washed and resuspended in RPMI 1640 culture medium supplemented with 5% (v/v) heat inactivated human AB serum (BioWhittaker, Belgium) or 10% (v/v) heat inactivated FCS, 1.5 mM L-glutamine, 100 U/ml penicillin and 100 μg/ml streptomycin (all from Sigma).

Cytokine detection Thawed or fresh PBMC were resuspended at a concentration of $3\times10^6$/ml to $5\times10^6$/ml and added to plates which had previously received nothing or ODN in a variety of concentrations. The cells were cultured in a humidified incubator at 37° C. Culture supernatants were collected after the indicated time points. If not used immediately, supernatants were frozen at −20° C. until required. Amounts of cytokines in the supernatants were assessed using commercially available ELISA Kits or in-house ELISA developed using commercially available antibodies (e.g. from Becton Dickinson, Germany).

Example 1

5'-TCG Enhances Immunostimulatory Activity of Non-CpG or CpG ODNs (IL-10)

Human PBMC of two representative donors were incubated for 48 h with the indicated ODNs (FIG. 1). Supernatants were harvested and IL-10 measured by ELISA as described in Materials and Methods. The activity of non-CpG ODNs such as poly T ODNs or another non-CpG ODN, SEQ. ID NO.: 6, were strongly enhanced by adding a TCG trinucleotide to the 5' end. CpG ODNs lacking a 5'-TCG such as SEQ. ID NO.: 3, (Magone et al., Eur. J. Immunol. 2000; 30: 1841-1850) could also be modified to exhibit higher potency and/or efficacy with the addition of a 5'TCG.

Example 2

TCG Enhances Immunostimulatory Activity of Non-CpG or CpG ODNs (IFN-α)

Figure 2:
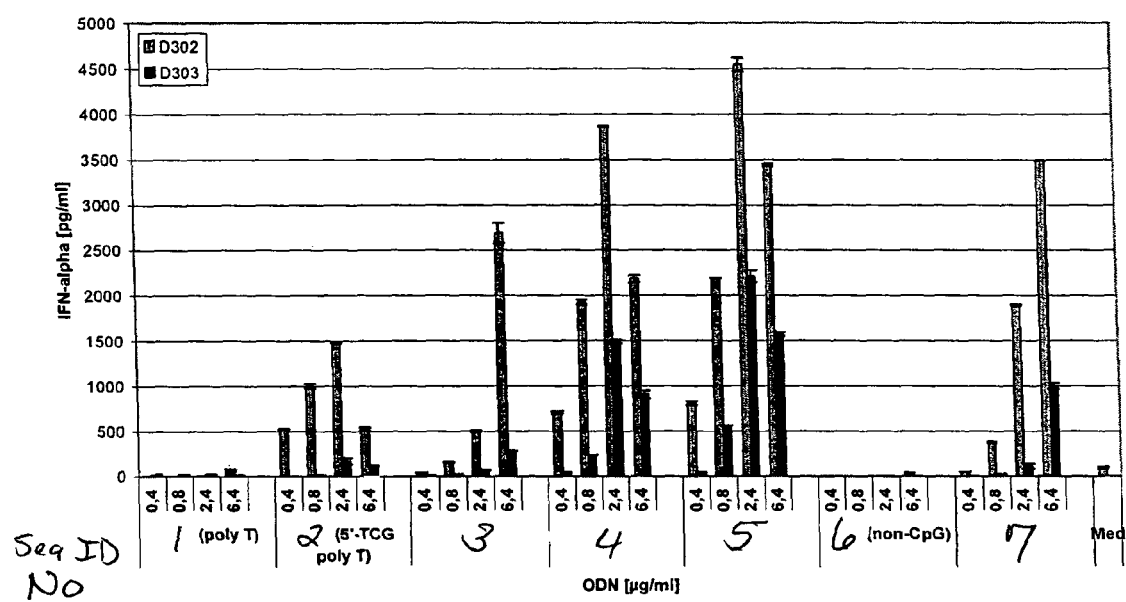
FIG. 2 is a bar graph depicting effect of a 5'-TCG motif on the immunostimulatory activity of non-CpG or CpG ODNs through induction of IFN-α.

Human PBMC of two representative donors were incubated for 48 h with the indicated ODNs (FIG. 2). Supernatants were harvested and IFN-α measured by ELISA as described in Materials and Methods. The effects of a 5'-TCG modification for the same ODNs as shown in FIG. 1 are demonstrated in this IFN-α assay.

Example 3

Enhancement of the Immune Response is Dependent on the CpG Dinucleotide

Figure 3:
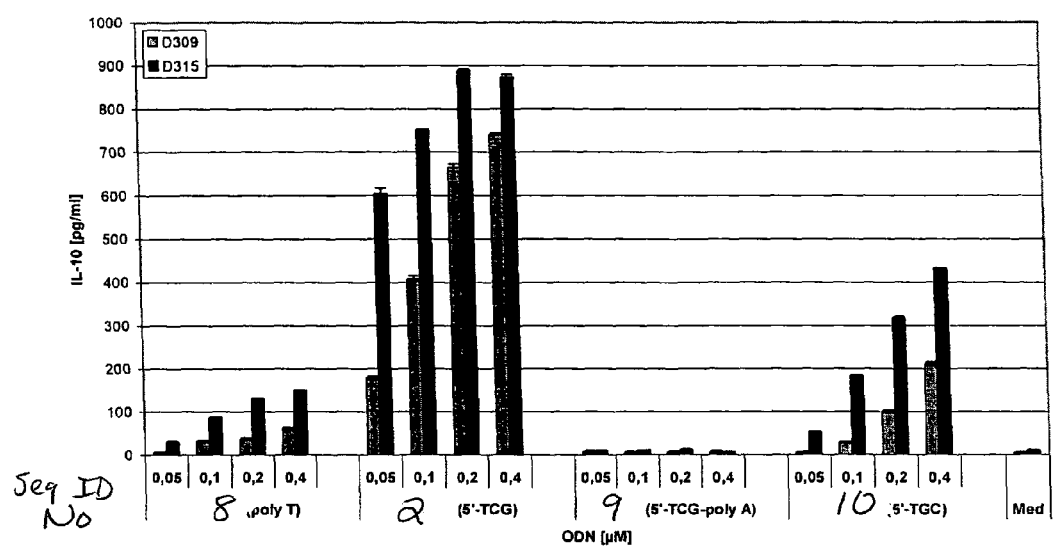
FIG. 3 is a bar graph depicting the effect of a 5'TCG on Poly-A and Poly-T sequences.

Human PBMC of two representative donors were incubated for 48 h with the indicated ODNs (FIG. 3). Supernatants were harvested and IL-10 measured by ELISA as described in Materials and Methods. Shown are the effect of a 5'-TCG, SEQ. ID NO.: 2, and a poly T sequence, SEQ. ID NO.: 8. Although a 5'-TGC, SEQ. ID NO.: 10, may have some minimal effect, the 5'-TCG modification clearly resulted in a much stronger potentiation of cytokine secretion. A 5'-TCG modification of a 17mer poly A ODN did not appear to have an effect, SEQ. ID NO.: 9. Similar results were obtained for interferon secretion. In contrast to the 5'-TCG plus poly A ODN a 5'-TCG ODN in a poly uracil context lead to enhancement of IL-10 secretion (Shown in FIG. 6).

Example 4

Figure 4:
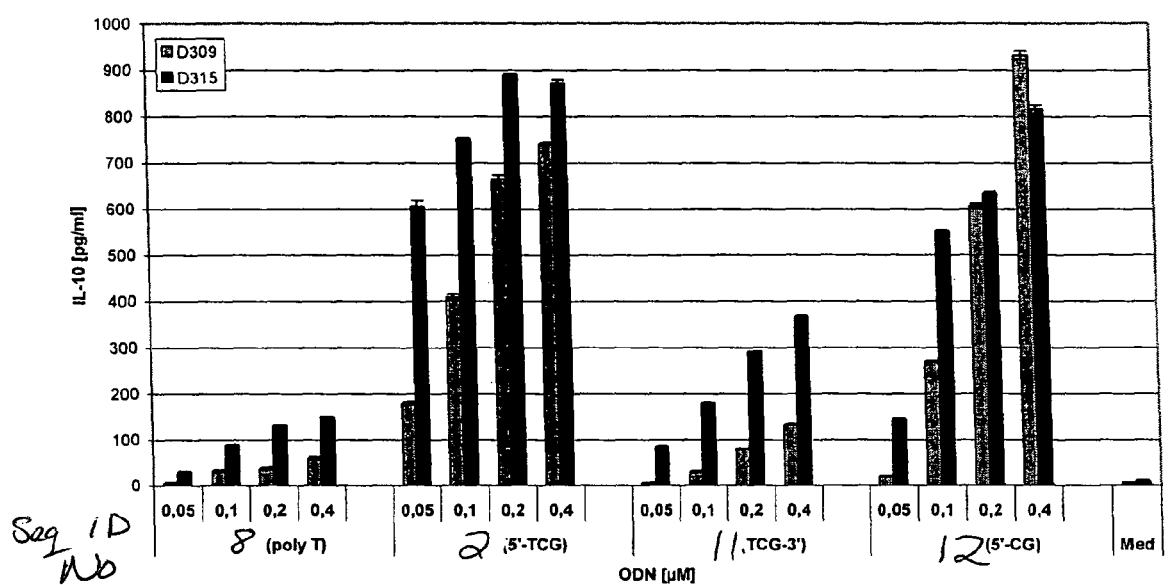
FIG. 4 is a bar graph depicting the effect of shifting the CpG dinucleotide from the 5' to the 3' end of an ODN.

Shifting the CpG Dinucleotide from the 5' to the 3' End of an ODN Results in Graded Loss of Immunostimulatory Capability Human PBMC of two representative donors were incubated for 48 h with the indicated ODNs (FIG. 4). Supernatants were harvested and IL-10 measured by ELISA as described in Materials and Methods. The CpG dinucleotide at the 5' end of an ODN resulted in enhanced IL-10 secretion, SEQ. ID NO.: 2. Shifting the CpG to the 3' end, SEQ. ID NO.: 11, of a poly T ODN resulted in strongly reduced cytokine secretion. A 5'-CG, SEQ. ID NO.: 12, had also a potentiating effect although a 5'-TCG was more efficient in enhancing the cytokine response. Similar results were obtained for interferon secretion.

Example 5

Figure 5:
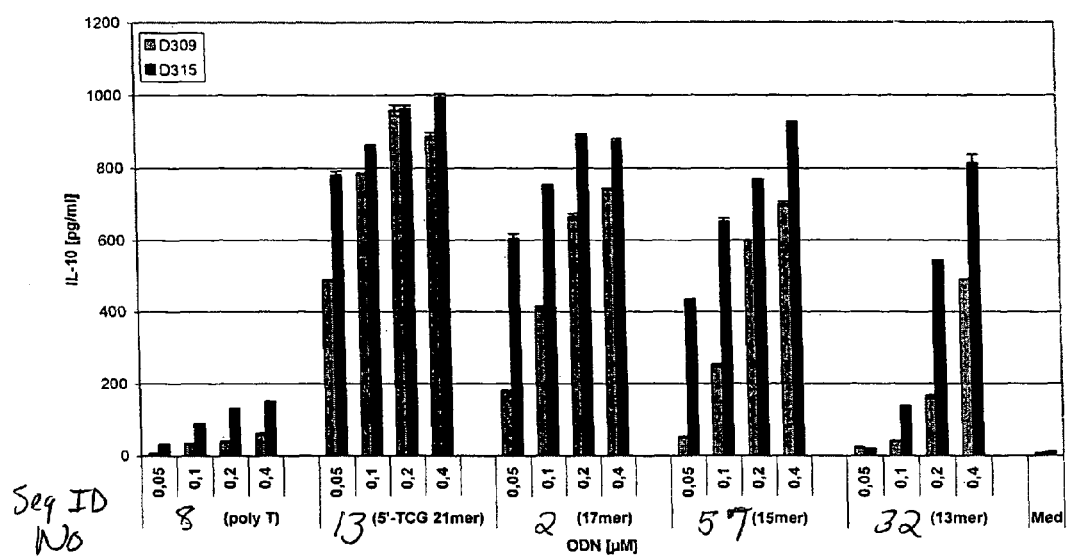
FIG. 5 is a bar graph demonstrating that the length of an ODN has an effect on stimulatory activity in addition to a 5'-TCG.

The Length of an ODN has an Effect on Stimulatory Activity in Addition to a 5'-TCG Human PBMC of two representative donors were incubated for 48 h with the indicated ODNs (FIG. 5). Supernatants were harvested and IL-10 measured by ELISA as described in Materials and Methods. The data demonstrate that the length of a CpG ODN plays a role in the stimulatory activity in addition to the 5'-TCG ODNs. A 21mer is more potent and efficient than a 17mer which is more potent than a 15mer or a 13mer.

Example 6

Figure 6:
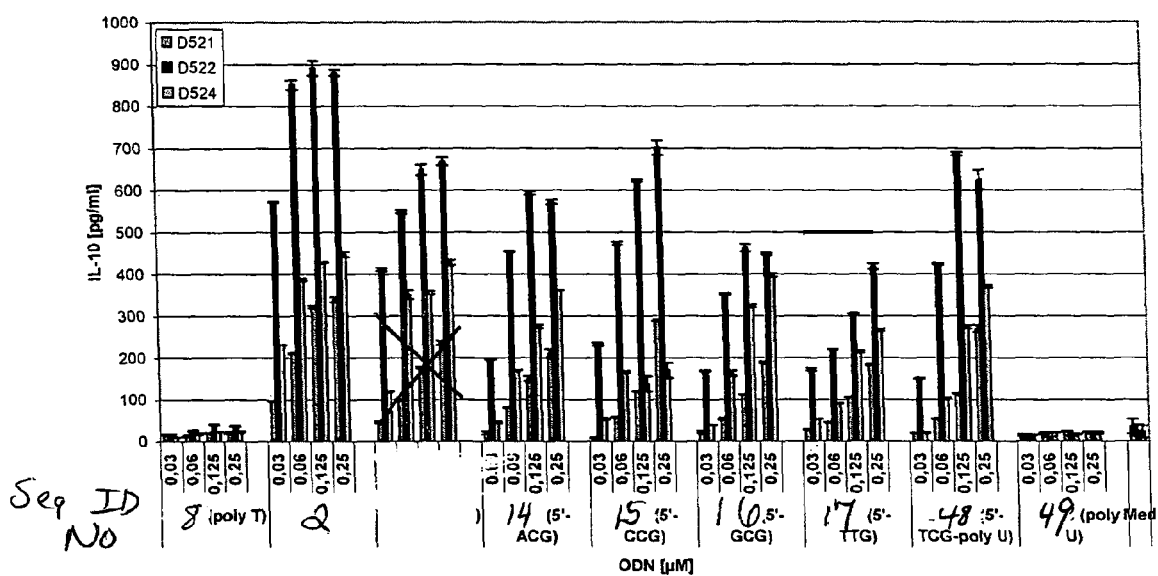
FIG. 6 is a bar graph depicting the effect of other 5' modifications in addition to 5'-TCG.

A 5'-TCG is the Most Stimulatory 5' Modification, but Other Modifications Also Lead to Enhanced Immunostimulation Human PBMC of three representative donors were incubated for 48 h with the indicated ODNs (FIG. 6). Supernatants were harvested and IL-10 measured by ELISA as described in Materials and Methods. A 5'-TCG is clearly the most potent 5' modification as demonstrated in the above experiment. Nevertheless, other 5' modifications were also able to enhance the stimulatory capability of poly T ODNs on human cells. Surprisingly, a 5'-TC alone was able to enhance cytokine secretion. Other 5' trinucleotides such as ACG, CCG and GCG lead also to enhanced IL-10 secretion although the 5'-TCG showed the strongest effects. Even a 5'-TTG was shown be more stimulatory than a purely poly T ODN. In addition, specific modifications of the sequence 3' to the 5'-TCG retained immunostimulation. In contrast to the 5'-TCG plus poly A ODN (FIG. 3) a 5'-TCG ODN in a poly uracil context lead to enhancement of IL-10 secretion.

Example 7

Figure 7A:
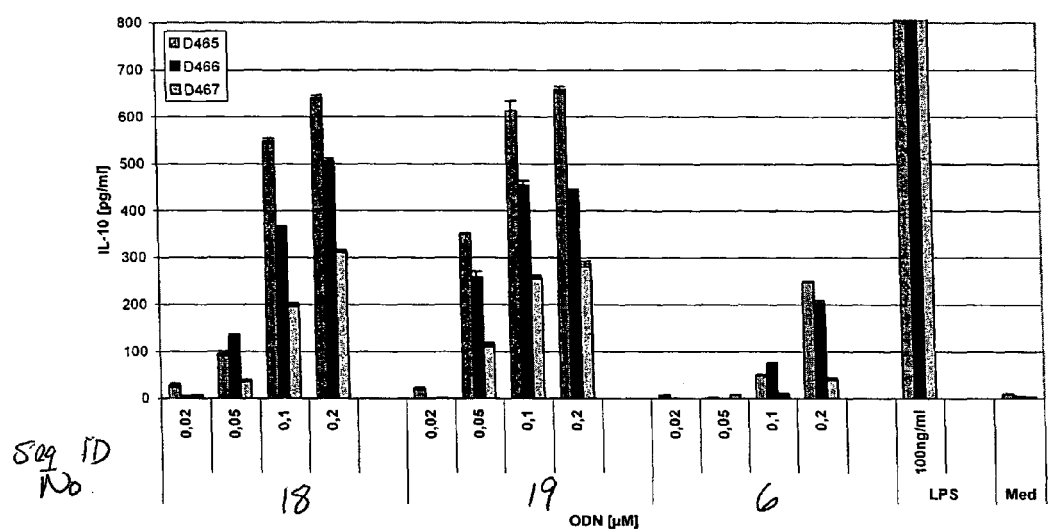
FIG. 7 is a set of bar graphs depicting the effect of a 5'-TCG modification on stimulatory capability of CpG ODNs as shown by different cellular effects: 7A (IL-10 induction) 7B (IFN-α induction) and 7C (IL-6 induction).
Figure 7B:
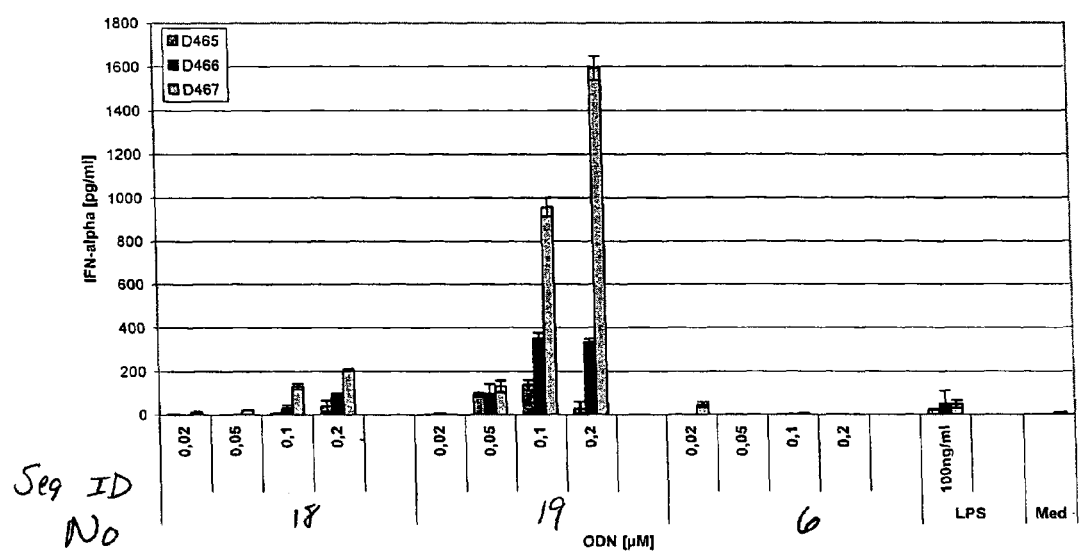
Figure 7C:
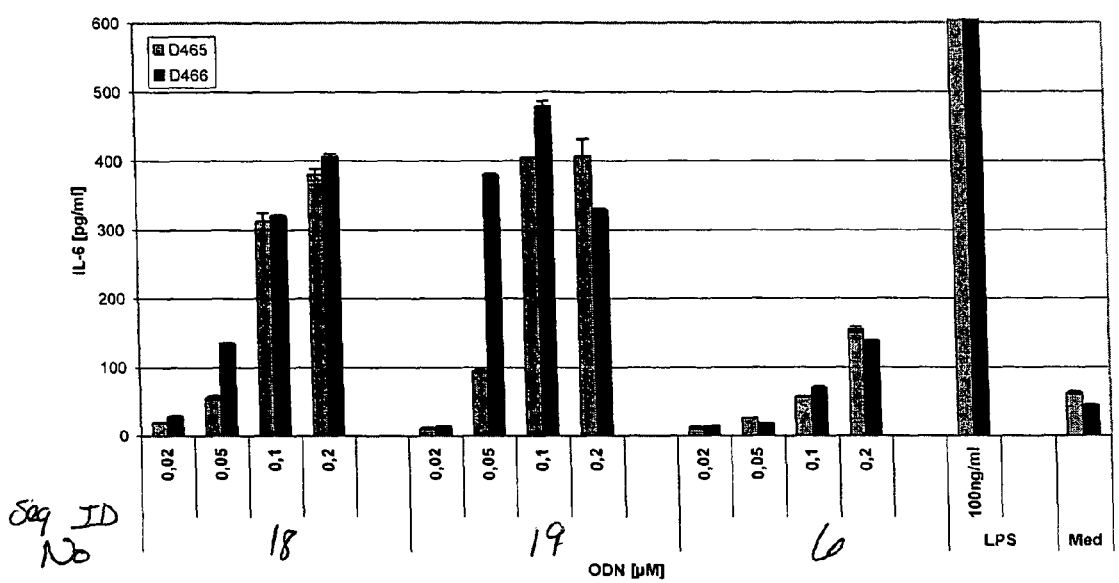

The 5'-TCG Modification Enhances the Stimulatory Capability of CpG ODNs as Shown by Different Cellular Effects a. Human PBMC of three representative donors were incubated for 48 h with the indicated ODNs ands supernatants were harvested and IL-10 measured by ELISA as described in Materials and Methods (FIG. 7A).
b. Human PBMC of three representative donors were incubated for 48 h with the indicated ODNs and supernatants were harvested and IFN-α measured by ELISA as described in Materials and Methods (FIG. 7B).
c. Human PBMC of two representative donors were incubated for 20 h with the indicated ODNs and supernatants were harvested and IL-6 measured by ELISA as described in Materials and Methods (FIG. 7C).
FIG. 7A to 7C demonstrate that the 5'-TCG is able to enhance the stimulatory capacity of an ODN in a variety of assays. The parent CpG ODN SEQ. ID NO.: 18 does not have a CpG dinucleotide directly at the 5' end. Modifying the sequence with a 5'-TCG, SEQ. ID NO.: 19, also enhanced the activity of the CpG ODN.

Example 8

IL-10 Secretion Induced by ODN with 5'-TCG

Figure 8:
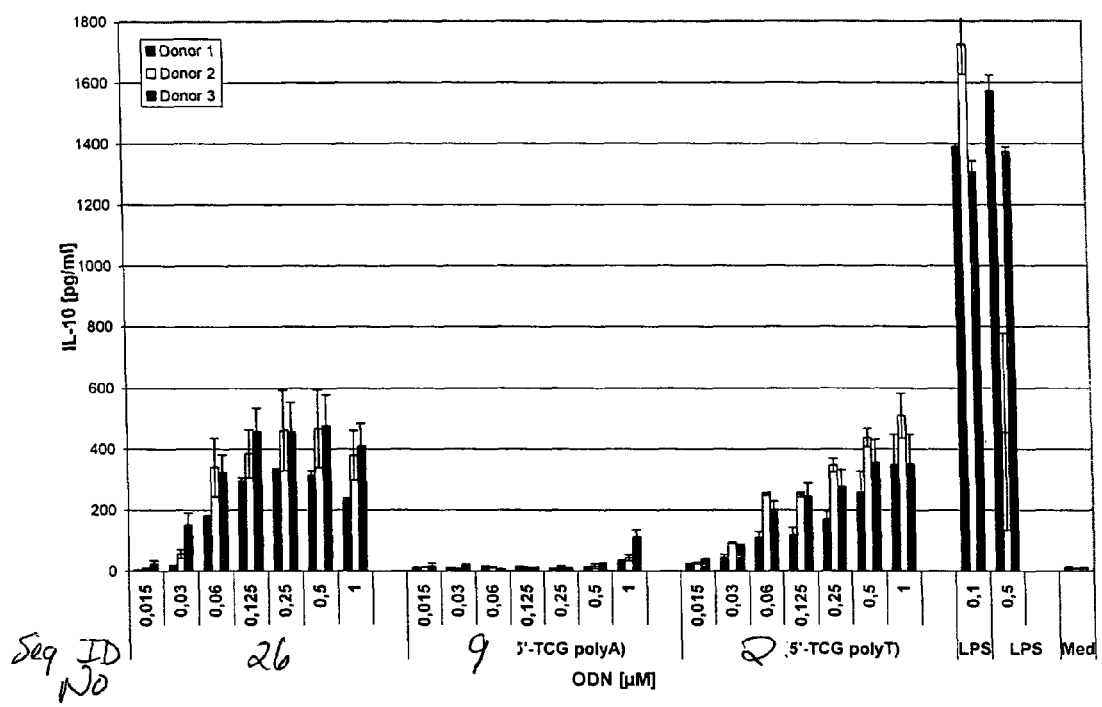
FIG. 8 is a set of bar graphs that shows IL-10 secretion induced by ODN with 5'-TCG.

Human PBMC were incubated with increasing concentrations of the indicated ODN's for 48 h. Supernatant was harvested and IL-10 measured by ELISA as described in Materials and Methods. Shown is the result for three individual donors. This experiment was a dose response study that investigated the contribution of thymidines 3' of the 5'-TCG trinucleotide with ODN concentrations up to 1 µM. As shown in FIG. 8, at 1 µM low stimulation of cytokine secretion (IL-10) can be observed with SEQ. ID NO.: 9 (5'-TCG plus poly A).

Example 9

IL-10 Secretion Induced by ODN with 5'-TCG and Increasing Numbers of Thymidines

Figure 9:
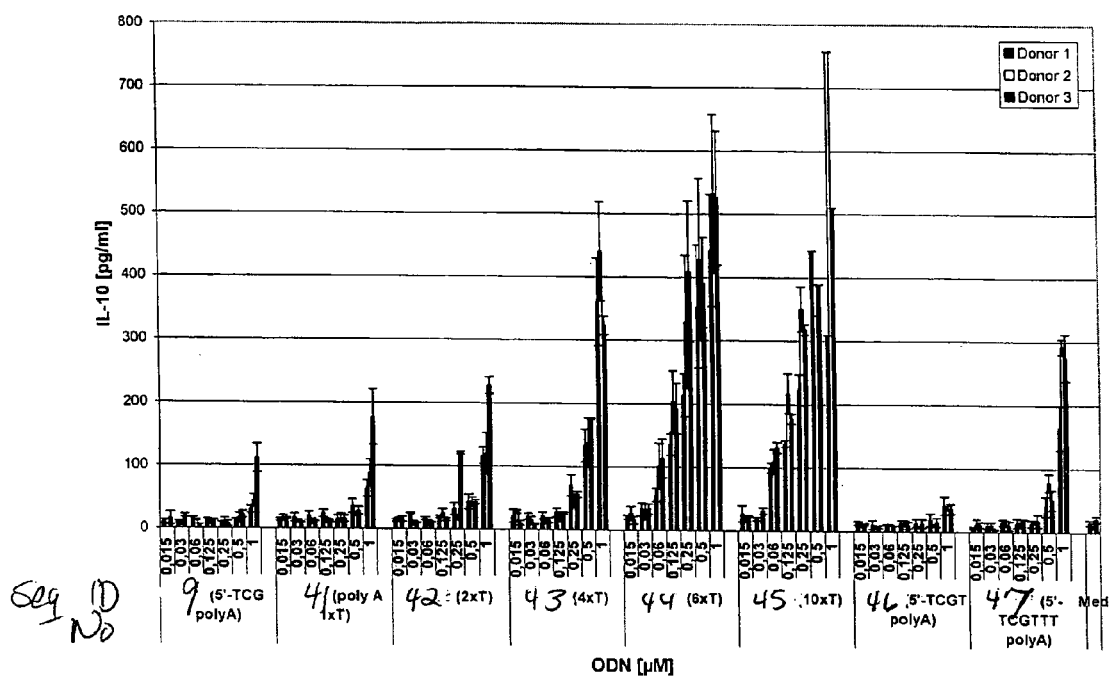
FIG. 9 is a set of bar graphs that shows IL-10 secretion induced by ODN with 5'-TCG and increasing numbers of thymidines.

Human PBMC were incubated with the indicated ODN for 48 h. Supernatant was harvested and IL-10 measured by ELISA as described in Materials and Methods. Shown is the result for three individual donors. To investigate whether the addition of thymidines to the 3' tail of ODN's would increase in vitro cytokine production, the ODN's were modified by exchanging increasing numbers of adenosines to thymidines. The addition of only one thymidine to the poly A tail led to an increase of immunostimulation as can be observed with SEQ. ID NO.: 41 (FIG. 9). Adding more thymidines led to further increase of IL-10 production, dependent on the number of thymidines. A 5'-TCG was sufficient to enhance immunostimulation by phosphorothioate ODN independent of the nucleotide sequence. Nevertheless, an increasing number of pyrimidines further contributed to this stimulation. Only two to four thymidines 3' of the 5'-TCG (here: about at least 20% thymidines) were sufficient to lead to a significant increase of cytokine secretion (SEQ. ID NO.: 42 and SEQ. ID NO.: 43).

Example 10

Figure 10A:
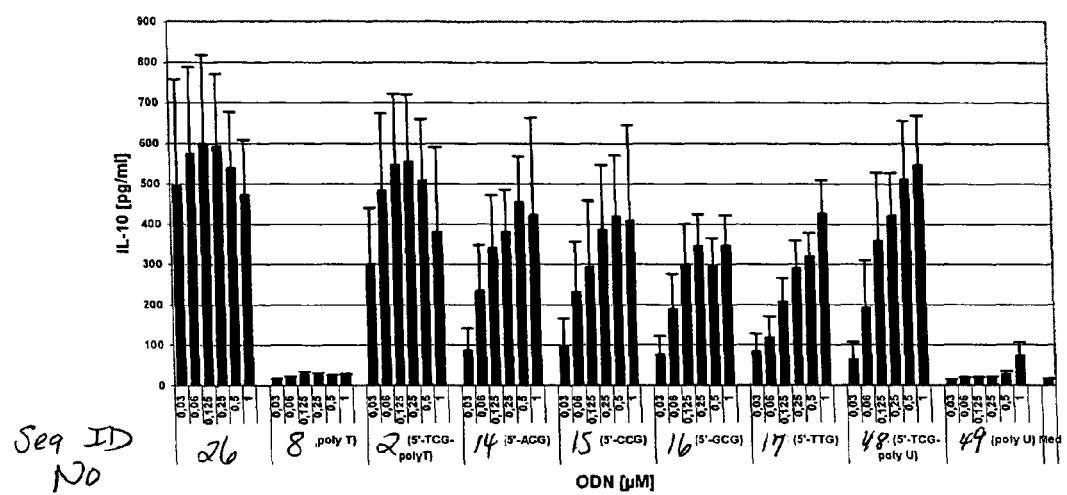
FIG. 10A is a set of bar graphs that depicts ODN's with a 5'-TCG as the most potent and efficient ODN's to induce a strong Th1-mediated immune response: 10A (IL-10 induction).

ODN with a 5'-TCG are the Most Potent and Efficient ODN to Induce a Strong Th1-Mediated Immune Response Human PBMC of three representative donors were incubated for 48 h with the indicated ODN concentrations (FIGS. 10A and 10B). Supernatants were harvested and IL-10 and IFN-α measured by ELISA as described in Materials and Methods. Shown is the Mean±SEM. The 5'-TCG led to the most potent and efficient immune stimulation of all ODN tested (in terms of the B cell related cytokine IL-10). Nevertheless, when the potential of ODN's with different 5' ends to induce the Th1 related cytokine IFN-α was measured, it was observed that only the 5'-TCG supported strong secretion of this cytokine (FIG. 10B).

Example 11

Figure 11:
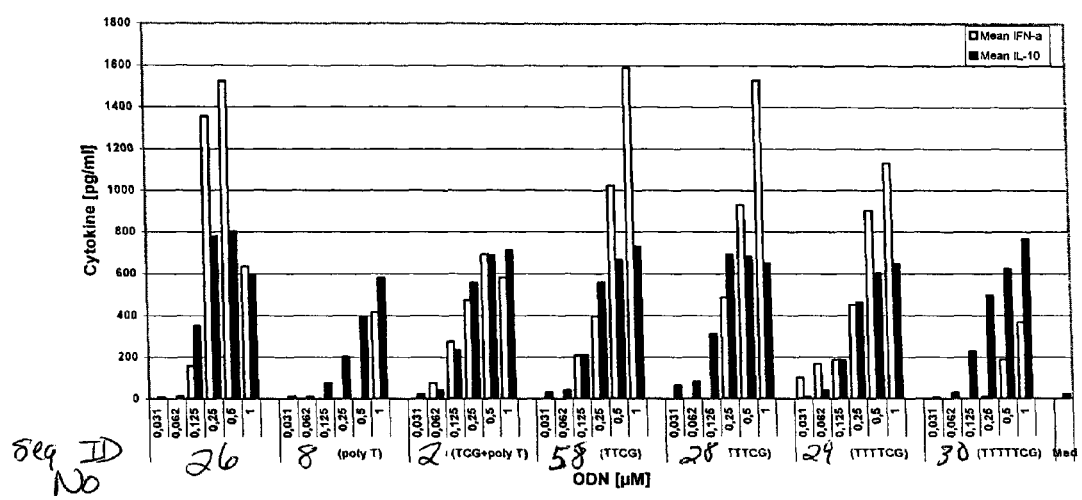
FIG. 11 is a set of bar graphs that depicts how the position of CpG dinucleotides in immune stimulatory ODN determines the strength of type I IFN secretion.

The Position of CpG Dinucleotides in Immune Stimulatory ODN Determines the Strength of type I IFN Secretion Human PBMC of three representative donors were incubated for 48 h with the indicated ODN concentrations. Supernatants were harvested and IFN-α measured by ELISA as described in Materials and Methods. Shown is the Mean. Shifting the CpG dinucleotide (essential for efficient immune stimulation) from the 5' to the 3' end led to a graded loss of immune stimulation (measured as secretion of the B cell related cytokine IL-10). FIG. 11 demonstrates that the position of the CpG also strongly influences the strength of type I IFN secretion. Surprisingly, shifting the CpG only one to three positions to the 3' end led to strongly enhanced IFN-α secretion especially with ODN SEQ. ID NO.: 27 and SEQ. ID NO.: 28. Shifting further to the 3' end led to strong decrease of IFN-α secretion below the level of SEQ. ID NO.: 2 (5'-TCG).

Example 12

Type I IFN Secretion Induced by Short 5'-TCG ODN

Figure 12:
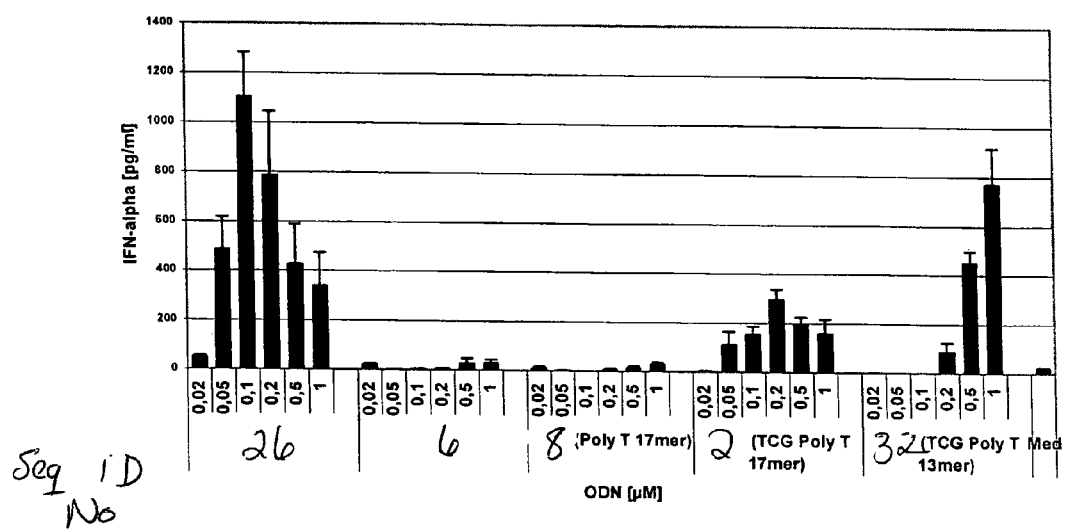
FIG. 12 is a set of bar graphs that shows type I IFN secretion induced by short 5'-TCG ODN's.

Human PBMC of three representative donors were incubated for 48 h with the indicated ODN concentrations. Supernatants were harvested and IFN-α measured by ELISA as described in Materials and Methods. Shown is the Mean±SEM. Previous findings have shown decrease of immune stimulation (measured as IL-10 secretion) upon shortening of the ODN's length. Nevertheless, when the secretion of IFN-α by shortened ODN's (e.g. 13mer SEQ. ID NO.: 32 with 5'-TCG) was measured, surprisingly a strongly increased IFN-α secretion compared to the 17mer SEQ. ID NO.: 2 was observed (FIG. 12).

Example 13

Figure 13A:
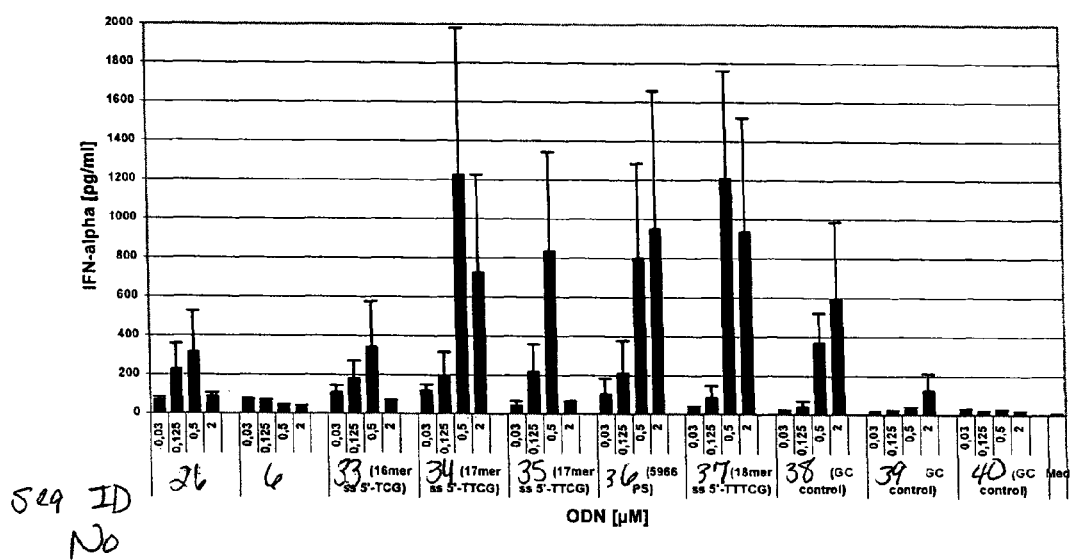
FIG. 13 is a set of bar graphs that shows the in vitro immune stimulation by a panel of newly generated CpG ODN's according to the observations described herein: 13A (IL-10 induction) and 13B (IFN-α induction).
Figure 13B:
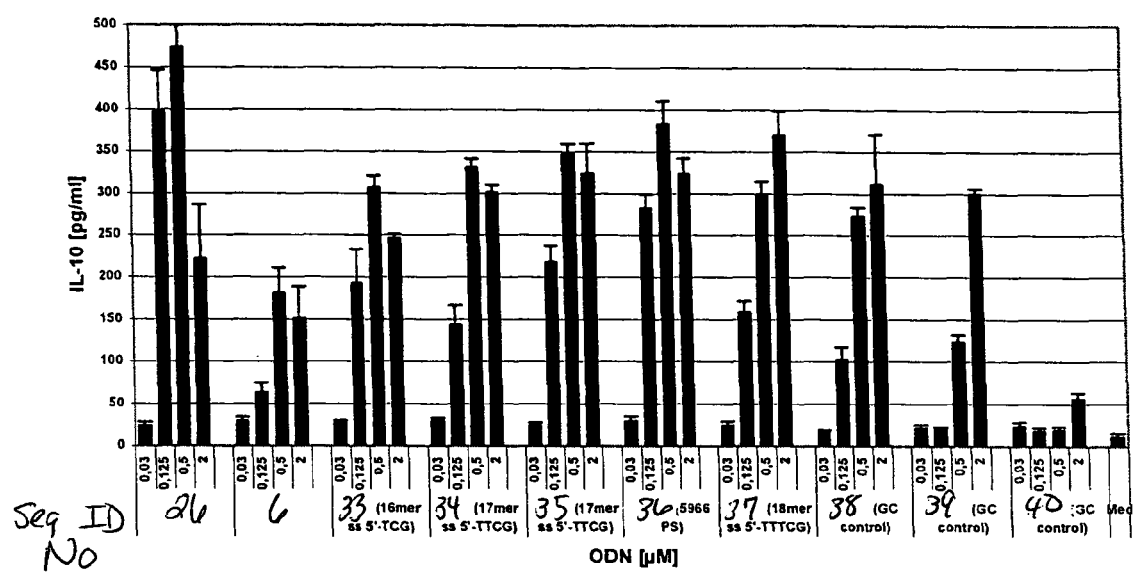

In Vitro Immune Stimulation by a Panel of Newly Generated CpG ODN According to the Observations Described Herein The important observations that were described in the previous examples were:
 a. A 5' TCG supports efficient and potent IFN-α (a Th1 related cytokine) as well as IL-10 secretion (a B cell related cytokine);
 b. Shifting the CpG dinucleotide from the 5' to the 3' end led first to an increase of type I IFN secretion and further 3' shifts led to a decrease (B cell activation was only decreased or only slightly changed by CpG shifts);
 c. Shortening an ODN with a 5'-TCG led to a strong increase in the potential to induce IFN-α (in contrast to other effects, e.g. secretion of IL-10);

These observations were combined and a panel of short CpG ODN's was created that were tested for their potential to induce the secretion of IFN-α as well as to activate B cells. Human PBMC of three representative donors were incubated for 48 h with the indicated ODN concentrations. Supernatants were harvested and IL-10 and IFN-α measured by ELISA as described in Materials and Methods. Shown is the Mean±SEM. As demonstrated in FIG. 13A ODN's were generated with lengths below 20 nucleotides that induced more efficient IFN-α secretion than a typical 24mer B-Class ODN, SEQ. ID NO.: 26. The difference between ODN SEQ. ID NO.: 36 (PS) and SEQ. ID NO.: 35 (semi-soft) in FIG. 13A indicated a shift of the bell-shaped curve to lower ODN concentrations (down-turn of the activation curve can be observed at lower ODN concentrations with SEQ. ID NO.: 35). In addition, loss of single to all CpG dinucleotides as in SEQ. ID NO.: 38 to SEQ. ID NO.: 40 led to a decrease of cytokine secretion, confirming that the observed effects were CpG-dependent. FIG. 13B (and FIG. 14) demonstrate that such short ODN were perfectly able to induce the activation of B cells (measured as CD80 up-regulation on CD19-positive B cells as well as secretion of the cytokine IL-10 produced by B cells).

Example 14

Short CpG ODN are Perfectly able to Induce Efficient B Cell Stimulation

Figure 14:
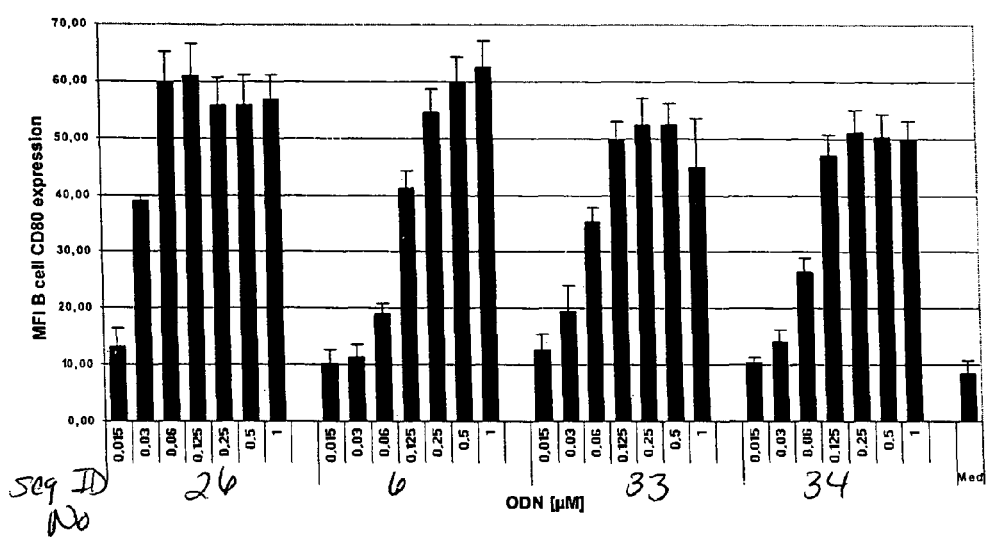
FIG. 14 is a set of bar graphs depicting B cell stimulation by short CpG ODN's.

Human PBMC of three representative donors were incubated for 24 h with the indicated ODN concentrations and cells harvested and stained for CD19, CD14 and CD80. Expression of CD80 on CD19-positive B cells was measured by flow cytometry as described. FIG. 14 demonstrates that such short ODN were perfectly able to induce the activation of B cells (measured as CD80 up-regulation on CD19-positive B cells as well as secretion of the cytokine IL-10 produced by B cells).

Example 15

Figure 15:
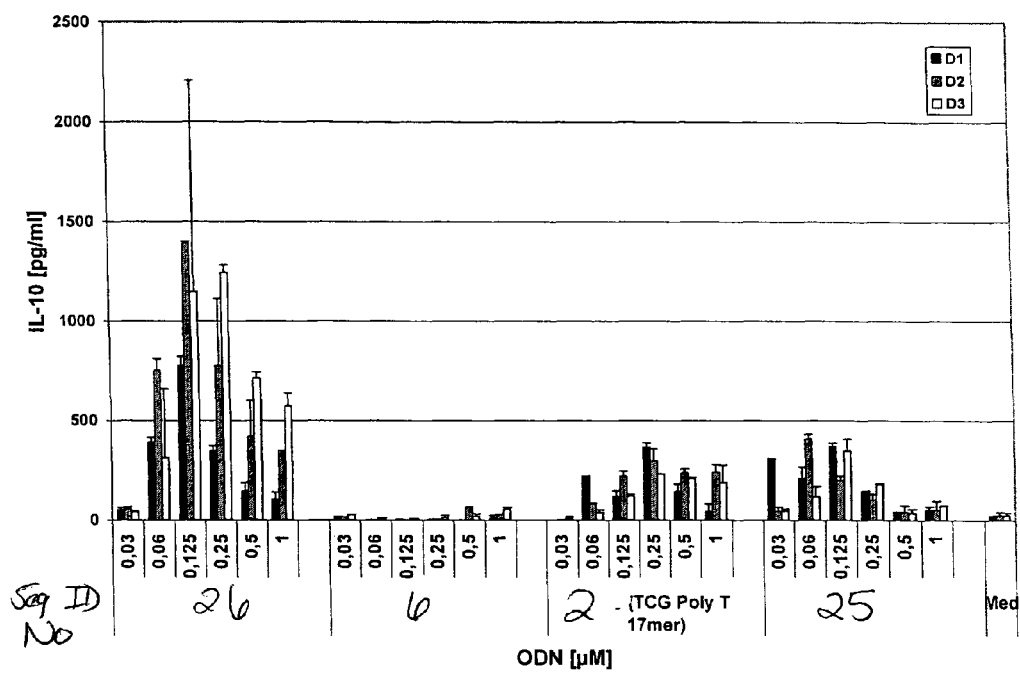
FIG. 15 is a bar graph that shows IL-10 induction by a panel of CpG ODN's and which demonstrates that some ODN having phosphodiester linkage between C and G have increased potency.

A Phosphodiester Linkage Between the C and G of the 5' CpG Dinucleotide Results in Enhancement of Potency of Immune Stimulation Human PBMC of three representative donors were incubated with the indicated ODN concentrations for 48 h. Supernatants were harvested and IL-10 measured by ELISA as described above. The introduction of a phosphodiester linkage between the CpG dinucleotide in an ODN with a 5'-TCG, SEQ. ID NO.: 25, led to a shift of the IL-10 secretion to lower ODN concentrations compared to an ODN with an unmodified 5'-TCG (SEQ. ID NO.: 2). The data is shown in FIG. 15. A similar result was obtained for IFN-alpha secretion.

Example 16

Modifications of the T Preceeding the 5'-CG are Allowed

Figure 16:
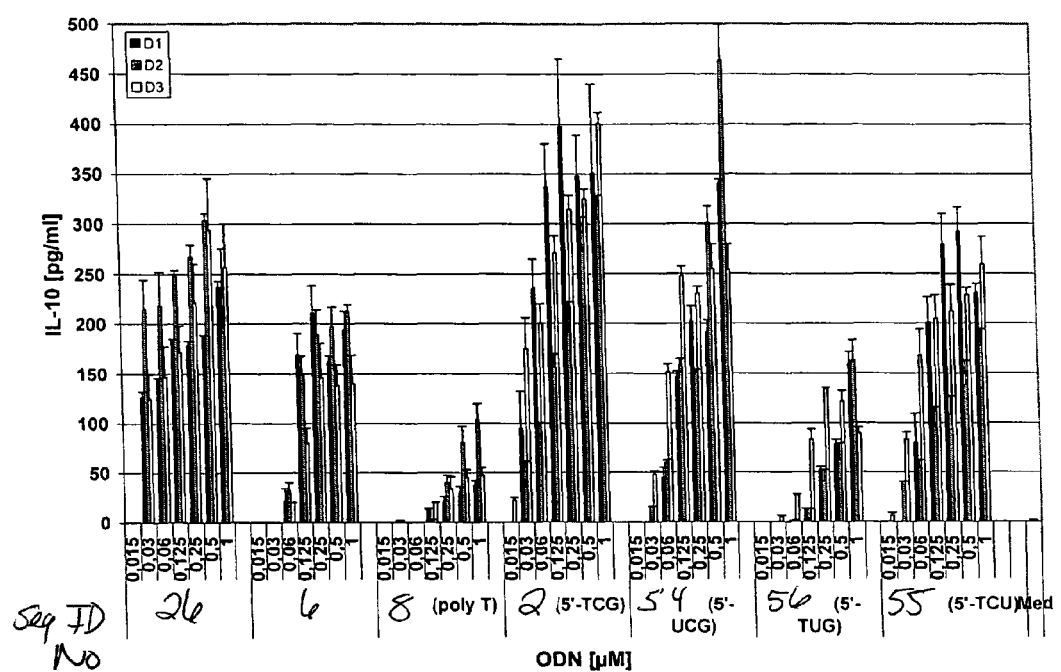
FIG. 16 is a bar graph that shows IL-10 induction by a panel of CpG ODN's and which demonstrates that some ODN having a modified 5' TCG induce IL-10.

Human PBMC of three representative donors were incubated with the indicated ODN concentrations for 48 h. Supernatants were harvested and IL-10 measured by ELISA as described above. The result shown in FIG. 16 demonstrate that:
 1. an ODN with a 5'-UCG (SEQ. ID NO. 54) induced similar strong cytokine secretion as an ODN with a 5'-TCG (SEQ. ID NO.: 2). Both ODN were superior to a pure poly T ODN (SEQ. ID NO.: 8). This result suggests that a variety of chemical modified nucleotides 5' to the CpG are allowed to induce an enhanced immune stimulation.
 2. ODN with a 5'-TCU (SEQ. ID NO. 55) or 5'-TUG (SEQ. ID NO. 56) also demonstrated enhanced cytokine secretion when compared to a poly T ODN (SEQ. ID NO.: 8). Nevertheless, a 5'-TCG was superior to these two modifications and the 5'-TCU induced more efficient IL-10 secretion than the 5'-TUG. These results suggest that a variety of chemical modifications at the CpG dinucleotide are allowed to induce enhanced immune stimulation.

The foregoing written specification is considered to be sufficient to enable one skilled in the art to practice the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

We claim:

1. An isolated oligonucleotide comprising:
   5'TCGX$_1$X$_2$N$_1$3'
   wherein X$_1$ is any nucleotide, X$_2$ is A, T, or C when X$_1$ is C or A, X$_2$ is A or G when X$_1$ is T, X$_2$ is any nucleotide when X$_1$ is G, N$_1$ is 2-95 nucleotides, wherein the CG dinucleotide is an unmethylated CG dinucleotide, wherein 5' designates the 5' end of the oligonucleotide and 3' designates the 3' end of the oligonucleotide, and wherein N$_1$ does not include an unmethylated CG motif, wherein the oligonucleotide is 13-100 nucleotides in length.

2. The oligonucleotide of claim 1, wherein the oligonucleotide includes at least 1 modified internucleotide linkage.

3. The oligonucleotide of claim 1, wherein the oligonucleotide includes at least 50% modified internucleotide linkage.

4. The oligonucleotide of claim 1, wherein all internucleotide linkages of the oligonucleotide are modified.

5. The oligonucleotide of claim 2, wherein the stabilized internucleotide linkage is a phosphorothioate linkage.

6. The oligonucleotide of claim 1, wherein N$_1$ is N$_2$N$_3$ and wherein N$_2$ is 8-40 nucleotides and N$_3$ is 2-5 pyrimidines.

7. The oligonucleotide of claim 6, wherein N$_3$ is TTTTT.

8. The oligonucleotide of claim 6, wherein N$_3$ is TT.

9. The oligonucleotide of claim 1, wherein N$_1$ is at least 50% pyrimidine.

10. The oligonucleotide of claim 1, wherein N$_1$ is at least 80% pyrimidine.

11. The oligonucleotide of claim 1, wherein N$_1$ is free of Poly-A and Poly-G sequences.

12. The oligonucleotide of claim 1, wherein N$_1$ is TN$_2$ and wherein N$_2$ is 8-94 nucleotides.

13. The oligonucleotide of claim 1, wherein the oligonucleotide has a 3'-3' linkage with one or two accessible 5' ends.

14. The oligonucleotide of claim 13, wherein the oligonucleotide has two accessible 5' ends, each of which are 5'TCG.

15. A method for inducing cytokine production, comprising:
   administering to a subject an oligonucleotide of claim 1 in an effective amount to induce a cytokine selected from the group consisting of, IFN-α and IL-10.

* * * * *

SEQUENCE LISTING

<160> NUMBER OF SEQ ID NOS: 69

<210> SEQ ID NO 1
<211> LENGTH: 18
<212> TYPE: DNA
<213> ORGANISM: Artificial
<220> FEATURE:
<223> OTHER INFORMATION: Synthetic oligonucleotide

<400> SEQUENCE: 1
tttttttttt tttttttt                                                 18

<210> SEQ ID NO 2
<211> LENGTH: 17
<212> TYPE: DNA
<213> ORGANISM: Artificial
<220> FEATURE:
<223> OTHER INFORMATION: Synthetic oligonucleotide

<400> SEQUENCE: 2
tcgttttttt ttttttt                                                  17

<210> SEQ ID NO 3
<211> LENGTH: 22
<212> TYPE: DNA
<213> ORGANISM: Artificial
<220> FEATURE:
<223> OTHER INFORMATION: Synthetic oligonucleotide

<400> SEQUENCE: 3
tgactgtgaa cgttcgagat ga                                            22

<210> SEQ ID NO 4
<211> LENGTH: 25
<212> TYPE: DNA
<213> ORGANISM: Artificial
<220> FEATURE:
<223> OTHER INFORMATION: Synthetic oligonucleotide

<400> SEQUENCE: 4
tcgtgactgt gaacgttcga gatga                                         25

<210> SEQ ID NO 5
<211> LENGTH: 22
<212> TYPE: DNA
<213> ORGANISM: Artificial
<220> FEATURE:
<223> OTHER INFORMATION: Synthetic oligonucleotide

<400> SEQUENCE: 5
tcgctgtgaa cgttcgagat ga                                            22

<210> SEQ ID NO 6
<211> LENGTH: 20
<212> TYPE: DNA
<213> ORGANISM: Artificial
<220> FEATURE:
<223> OTHER INFORMATION: Synthetic oligonucleotide

<400> SEQUENCE: 6
tccaggactt ctctcaggtt                                               20

<210> SEQ ID NO 7
<211> LENGTH: 23
<212> TYPE: DNA

```
<213> ORGANISM: Artificial
<220> FEATURE:
<223> OTHER INFORMATION: Synthetic oligonucleotide

<400> SEQUENCE: 7
tcgtccagga cttctctcag gtt                                              23

<210> SEQ ID NO 8
<211> LENGTH: 17
<212> TYPE: DNA
<213> ORGANISM: Artificial
<220> FEATURE:
<223> OTHER INFORMATION: Synthetic oligonucleotide

<400> SEQUENCE: 8
tttttttttt ttttttt                                                     17

<210> SEQ ID NO 9
<211> LENGTH: 17
<212> TYPE: DNA
<213> ORGANISM: Artificial
<220> FEATURE:
<223> OTHER INFORMATION: Synthetic oligonucleotide

<400> SEQUENCE: 9
tcgaaaaaaa aaaaaaa                                                     17

<210> SEQ ID NO 10
<211> LENGTH: 17
<212> TYPE: DNA
<213> ORGANISM: Artificial
<220> FEATURE:
<223> OTHER INFORMATION: Synthetic oligonucleotide

<400> SEQUENCE: 10
tgcttttttt ttttttt                                                     17

<210> SEQ ID NO 11
<211> LENGTH: 17
<212> TYPE: DNA
<213> ORGANISM: Artificial
<220> FEATURE:
<223> OTHER INFORMATION: Synthetic oligonucleotide

<400> SEQUENCE: 11
tttttttttt tttttcg                                                     17

<210> SEQ ID NO 12
<211> LENGTH: 17
<212> TYPE: DNA
<213> ORGANISM: Artificial
<220> FEATURE:
<223> OTHER INFORMATION: Synthetic oligonucleotide

<400> SEQUENCE: 12
cgtttttttt ttttttt                                                     17

<210> SEQ ID NO 13
<211> LENGTH: 21
<212> TYPE: DNA
<213> ORGANISM: Artificial
<220> FEATURE:
<223> OTHER INFORMATION: Synthetic oligonucleotide

<400> SEQUENCE: 13
tcgttttttt tttttttttt t                                                21
```

```
<210> SEQ ID NO 14
<211> LENGTH: 17
<212> TYPE: DNA
<213> ORGANISM: Artificial
<220> FEATURE:
<223> OTHER INFORMATION: Synthetic oligonucleotide

<400> SEQUENCE: 14
acgttttttt ttttttt                                                   17

<210> SEQ ID NO 15
<211> LENGTH: 17
<212> TYPE: DNA
<213> ORGANISM: Artificial
<220> FEATURE:
<223> OTHER INFORMATION: Synthetic oligonucleotide

<400> SEQUENCE: 15
ccgttttttt ttttttt                                                   17

<210> SEQ ID NO 16
<211> LENGTH: 17
<212> TYPE: DNA
<213> ORGANISM: Artificial
<220> FEATURE:
<223> OTHER INFORMATION: Synthetic oligonucleotide

<400> SEQUENCE: 16
gcgttttttt ttttttt                                                   17

<210> SEQ ID NO 17
<211> LENGTH: 17
<212> TYPE: DNA
<213> ORGANISM: Artificial
<220> FEATURE:
<223> OTHER INFORMATION: Synthetic oligonucleotide

<400> SEQUENCE: 17
ttgttttttt ttttttt                                                   17

<210> SEQ ID NO 18
<211> LENGTH: 25
<212> TYPE: DNA
<213> ORGANISM: Artificial
<220> FEATURE:
<223> OTHER INFORMATION: Synthetic oligonucleotide

<400> SEQUENCE: 18
tgtcgttgtc gttgtcgttg tcgtt                                          25

<210> SEQ ID NO 19
<211> LENGTH: 26
<212> TYPE: DNA
<213> ORGANISM: Artificial
<220> FEATURE:
<223> OTHER INFORMATION: Synthetic oligonucleotide

<400> SEQUENCE: 19
tcgtcgttgt cgttgtcgtt gtcgtt                                         26

<210> SEQ ID NO 20
<211> LENGTH: 20
<212> TYPE: DNA
<213> ORGANISM: Artificial
<220> FEATURE:
<223> OTHER INFORMATION: Synthetic oligonucleotide
```

```
<400> SEQUENCE: 20
tccatgacgt tcctgacgtt                                              20

<210> SEQ ID NO 21
<211> LENGTH: 20
<212> TYPE: DNA
<213> ORGANISM: Artificial
<220> FEATURE:
<223> OTHER INFORMATION: Synthetic oligonucleotide

<400> SEQUENCE: 21
tcgatgacgt tcctgacgtt                                              20

<210> SEQ ID NO 22
<211> LENGTH: 26
<212> TYPE: DNA
<213> ORGANISM: Artificial
<220> FEATURE:
<223> OTHER INFORMATION: Synthetic oligonucleotide

<400> SEQUENCE: 22
tcgtcgtcca ggacttctct caggtt                                       26

<210> SEQ ID NO 23
<211> LENGTH: 25
<212> TYPE: DNA
<213> ORGANISM: Artificial
<220> FEATURE:
<223> OTHER INFORMATION: Synthetic oligonucleotide

<400> SEQUENCE: 23
tcgtcgctgt gaacgttcga gatga                                        25

<210> SEQ ID NO 24
<211> LENGTH: 25
<212> TYPE: DNA
<213> ORGANISM: Artificial
<220> FEATURE:
<223> OTHER INFORMATION: Synthetic oligonucleotide

<400> SEQUENCE: 24
tcgtgactgt gaacgttcga gatga                                        25

<210> SEQ ID NO 25
<211> LENGTH: 17
<212> TYPE: DNA
<213> ORGANISM: Artificial
<220> FEATURE:
<223> OTHER INFORMATION: Synthetic oligonucleotide

<400> SEQUENCE: 25
tcgttttttt ttttttt                                                 17

<210> SEQ ID NO 26
<211> LENGTH: 24
<212> TYPE: DNA
<213> ORGANISM: Artificial
<220> FEATURE:
<223> OTHER INFORMATION: Synthetic oligonucleotide

<400> SEQUENCE: 26
tcgtcgtttt gtcgttttgt cgtt                                         24

<210> SEQ ID NO 27
<211> LENGTH: 17
<212> TYPE: DNA
```

```
<213> ORGANISM: Artificial
<220> FEATURE:
<223> OTHER INFORMATION: Synthetic oligonucleotide

<400> SEQUENCE: 27 ttcgttttt tttttt                                                    17

<210> SEQ ID NO 28
<211> LENGTH: 17
<212> TYPE: DNA
<213> ORGANISM: Artificial
<220> FEATURE:
<223> OTHER INFORMATION: Synthetic oligonucleotide

<400> SEQUENCE: 28 tttcgtttt tttttt                                                    17

<210> SEQ ID NO 29
<211> LENGTH: 17
<212> TYPE: DNA
<213> ORGANISM: Artificial
<220> FEATURE:
<223> OTHER INFORMATION: Synthetic oligonucleotide

<400> SEQUENCE: 29 ttttcgttt tttttt                                                    17

<210> SEQ ID NO 30
<211> LENGTH: 17
<212> TYPE: DNA
<213> ORGANISM: Artificial
<220> FEATURE:
<223> OTHER INFORMATION: Synthetic oligonucleotide

<400> SEQUENCE: 30 tttttcgtt tttttt                                                    17

<210> SEQ ID NO 31
<211> LENGTH: 20
<212> TYPE: DNA
<213> ORGANISM: Artificial
<220> FEATURE:
<223> OTHER INFORMATION: Synthetic oligonucleotide

<400> SEQUENCE: 31
tccaggactt ctctcaggtt                                               20

<210> SEQ ID NO 32
<211> LENGTH: 13
<212> TYPE: DNA
<213> ORGANISM: Artificial
<220> FEATURE:
<223> OTHER INFORMATION: Synthetic oigonucloetide

<400> SEQUENCE: 32
tcgttttttt ttt                                                      13

<210> SEQ ID NO 33
<211> LENGTH: 16
<212> TYPE: DNA
<213> ORGANISM: Artificial
<220> FEATURE:
<223> OTHER INFORMATION: Synthetic oligonucleotide

<400> SEQUENCE: 33
tcgtcgtttt gtcgtt                                                   16
```

<210> SEQ ID NO 34
<211> LENGTH: 17
<212> TYPE: DNA
<213> ORGANISM: Artificial
<220> FEATURE:
<223> OTHER INFORMATION: Synthetic oligonucleotide

<400> SEQUENCE: 34
ttcgtcgttt cgtcgtt                                                    17

<210> SEQ ID NO 35
<211> LENGTH: 17
<212> TYPE: DNA
<213> ORGANISM: Artificial
<220> FEATURE:
<223> OTHER INFORMATION: Synthetic oligonucleotide

<400> SEQUENCE: 35
ttcgtcgttt tgtcgtt                                                    17

<210> SEQ ID NO 36
<211> LENGTH: 17
<212> TYPE: DNA
<213> ORGANISM: Artificial
<220> FEATURE:
<223> OTHER INFORMATION: Synthetic oligonucleotide

<400> SEQUENCE: 36
ttcgtcgttt cgtcgtt                                                    17

<210> SEQ ID NO 37
<211> LENGTH: 18
<212> TYPE: DNA
<213> ORGANISM: Artificial
<220> FEATURE:
<223> OTHER INFORMATION: Synthetic oligonucleotide

<400> SEQUENCE: 37
tttcgtcgtt tcgtcgtt                                                   18

<210> SEQ ID NO 38
<211> LENGTH: 17
<212> TYPE: DNA
<213> ORGANISM: Artificial
<220> FEATURE:
<223> OTHER INFORMATION: Synthetic oligonucleotide

<400> SEQUENCE: 38
ttgctcgttt cgtcgtt                                                    17

<210> SEQ ID NO 39
<211> LENGTH: 17
<212> TYPE: DNA
<213> ORGANISM: Artificial
<220> FEATURE:
<223> OTHER INFORMATION: Synthetic oligonucleotide

<400> SEQUENCE: 39 ttgctgctttcgtcgtt                                                     17

<210> SEQ ID NO 40
<211> LENGTH: 17
<212> TYPE: DNA
<213> ORGANISM: Artificial
<220> FEATURE:
<223> OTHER INFORMATION: Synthetic oligonucleotide

```
<400> SEQUENCE: 40
ttgctgcttt gctgctt                                                    17

<210> SEQ ID NO 41
<211> LENGTH: 17
<212> TYPE: DNA
<213> ORGANISM: Artificial
<220> FEATURE:
<223> OTHER INFORMATION: Synthetic oligonucleotide

<400> SEQUENCE: 41
tcgaaaaaaa aaataaa                                                    17

<210> SEQ ID NO 42
<211> LENGTH: 17
<212> TYPE: DNA
<213> ORGANISM: Artificial
<220> FEATURE:
<223> OTHER INFORMATION: Synthetic oligonucleotide

<400> SEQUENCE: 42
tcgaaaaaaa aattaaa                                                    17

<210> SEQ ID NO 43
<211> LENGTH: 17
<212> TYPE: DNA
<213> ORGANISM: Artificial
<220> FEATURE:
<223> OTHER INFORMATION: Synthetic oligonucleotide

<400> SEQUENCE: 43
tcgaaaaaaa ttttaaa                                                    17

<210> SEQ ID NO 44
<211> LENGTH: 17
<212> TYPE: DNA
<213> ORGANISM: Artificial
<220> FEATURE:
<223> OTHER INFORMATION: Synthetic oligonucleotide

<400> SEQUENCE: 44
tcgaaaaatt ttttaaa                                                    17

<210> SEQ ID NO 45
<211> LENGTH: 17
<212> TYPE: DNA
<213> ORGANISM: Artificial
<220> FEATURE:
<223> OTHER INFORMATION: Synthetic oligonucleotide

<400> SEQUENCE: 45
tcgaaatttt tttttta                                                    17

<210> SEQ ID NO 46
<211> LENGTH: 17
<212> TYPE: DNA
<213> ORGANISM: Artificial
<220> FEATURE:
<223> OTHER INFORMATION: Synthetic oligonucleotide

<400> SEQUENCE: 46
tcgtaaaaaa aaaaaaa                                                    17

<210> SEQ ID NO 47
<211> LENGTH: 17
<212> TYPE: DNA
```

```
<213> ORGANISM: Artificial
<220> FEATURE:
<223> OTHER INFORMATION: Synthetic oligonucleotide

<400> SEQUENCE: 47
tcgtttaaaa aaaaaaa                                                  17

<210> SEQ ID NO 48
<211> LENGTH: 17
<212> TYPE: DNA
<213> ORGANISM: Artificial
<220> FEATURE:
<223> OTHER INFORMATION: Synthetic oligonucleotide

<400> SEQUENCE: 48
tcguuuuuuu uuuuuuu                                                  17

<210> SEQ ID NO 49
<211> LENGTH: 17
<212> TYPE: DNA
<213> ORGANISM: Artificial
<220> FEATURE:
<223> OTHER INFORMATION: Synthetic oligonucleotide

<400> SEQUENCE: 49
uuuuuuuuuu uuuuuuu                                                  17

<210> SEQ ID NO 50
<211> LENGTH: 20
<212> TYPE: DNA
<213> ORGANISM: Artificial
<220> FEATURE:
<223> OTHER INFORMATION: Synthetic oligonucleotide

<400> SEQUENCE: 50
tcgaggactt ctctcaggtt                                               20

<210> SEQ ID NO 51
<211> LENGTH: 17
<212> TYPE: DNA
<213> ORGANISM: Artificial
<220> FEATURE:
<223> OTHER INFORMATION: Synthetic oligonucleotide

<400> SEQUENCE: 51
tcgccccccc ccccccc                                                  17

<210> SEQ ID NO 52
<211> LENGTH: 18
<212> TYPE: DNA
<213> ORGANISM: Artificial
<220> FEATURE:
<223> OTHER INFORMATION: Synthetic oligonucleotide

<400> SEQUENCE: 52
tcgtcgagcg tgcgccat                                                 18

<210> SEQ ID NO 53
<211> LENGTH: 18
<212> TYPE: DNA
<213> ORGANISM: Artificial
<220> FEATURE:
<223> OTHER INFORMATION: Synthetic oligonucleotide

<400> SEQUENCE: 53
tcgcccagcg tgcgccat                                                 18
```

```
<210> SEQ ID NO 54
<211> LENGTH: 17
<212> TYPE: DNA
<213> ORGANISM: Artificial
<220> FEATURE:
<223> OTHER INFORMATION: Synthetic oligonucleotide

<400> SEQUENCE: 54
ucgttttttt ttttttt                                                    17

<210> SEQ ID NO 55
<211> LENGTH: 17
<212> TYPE: DNA
<213> ORGANISM: Artificial
<220> FEATURE:
<223> OTHER INFORMATION: Synthetic oligonucleotide

<400> SEQUENCE: 55
tcuttttttt ttttttt                                                    17

<210> SEQ ID NO 56
<211> LENGTH: 17
<212> TYPE: DNA
<213> ORGANISM: Artificial
<220> FEATURE:
<223> OTHER INFORMATION: Synthetic oligonucleotide

<400> SEQUENCE: 56
tugttttttt ttttttt                                                    17

<210> SEQ ID NO 57
<211> LENGTH: 15
<212> TYPE: DNA
<213> ORGANISM: Artificial
<220> FEATURE:
<223> OTHER INFORMATION: Synthetic oligonucleotide

<400> SEQUENCE: 57
tcgttttttt ttttt                                                      15

<210> SEQ ID NO 58
<211> LENGTH: 17
<212> TYPE: DNA
<213> ORGANISM: Artificial
<220> FEATURE:
<223> OTHER INFORMATION: Synthetic oligonucleotide

<400> SEQUENCE: 58
ttcgtttttt ttttttt                                                    17

<210> SEQ ID NO 59
<211> LENGTH: 17
<212> TYPE: DNA
<213> ORGANISM: Artificial
<220> FEATURE:
<223> OTHER INFORMATION: Synthetic oligonucleotide

<400> SEQUENCE: 59 ttttttttc gttttttt                                                    17

<210> SEQ ID NO 60
<211> LENGTH: 18
<212> TYPE: DNA
<213> ORGANISM: Artificial
<220> FEATURE:
<223> OTHER INFORMATION: Synthetic oligonucleotide
```

```
<400> SEQUENCE: 60
tctcccagcg tgcgccat                                                    18

<210> SEQ ID NO 61
<211> LENGTH: 100
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (6)..(100)
<223> OTHER INFORMATION: n is a, c, g, t or u
<220> FEATURE:
<221> NAME/KEY: n
<222> LOCATION: (8)..(100)
<223> OTHER INFORMATION: any one or more n's at positions 8 to 100 could
      be missing

<400> SEQUENCE: 61
tcgmhnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn                           100

<210> SEQ ID NO 62
<211> LENGTH: 100
<212> TYPE: DNA
<213> ORGANISM: Artificial
<220> FEATURE:
<223> OTHER INFORMATION: Synthetic oligonucleotide
<220> FEATURE:
<221> NAME/KEY: n
<222> LOCATION: (6)..(100)
<223> OTHER INFORMATION: any one or more n's at positions 8 to 100 could
      be missing
<220> FEATURE:
<221> NAME/KEY: misc_feature
<222> LOCATION: (6)..(100)
<223> OTHER INFORMATION: n is a, c, g, t or u

<400> SEQUENCE: 62
tcgtannnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn                           100

<210> SEQ ID NO 63
<211> LENGTH: 100
<212> TYPE: DNA
<213> ORGANISM: Artificial
<220> FEATURE:
<223> OTHER INFORMATION: Synthetic oligonucleotide
<220> FEATURE:
<221> NAME/KEY: n
<222> LOCATION: (5)..(100)
<223> OTHER INFORMATION: any one or more n's at positions 8 to 100 could
      be missing
<220> FEATURE:
<221> NAME/KEY: misc_feature
<222> LOCATION: (5)..(100)
<223> OTHER INFORMATION: n is a, c, g, t or u

<400> SEQUENCE: 63
tcggnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn                           100

<210> SEQ ID NO 64
<211> LENGTH: 100
<212> TYPE: DNA
<213> ORGANISM: Artificial
<220> FEATURE:
<223> OTHER INFORMATION: Synthetic oligonucleotide
```

-continued

```
<220> FEATURE:
<221> NAME/KEY: n
<222> LOCATION: (5)..(100)
<223> OTHER INFORMATION: any one or more n's at positions 9 to 100 could
      be missing
<220> FEATURE:
<221> NAME/KEY: misc_feature
<222> LOCATION: (5)..(100)
<223> OTHER INFORMATION: n is a, c, g, t or u

<400> SEQUENCE: 64 tcgtnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn                          100

<210> SEQ ID NO 65
<211> LENGTH: 20
<212> TYPE: DNA
<213> ORGANISM: Artificial
<220> FEATURE:
<223> OTHER INFORMATION: Synthetic oligonucleotide
<220> FEATURE:
<221> NAME/KEY: n
<222> LOCATION: (5)..(20)
<223> OTHER INFORMATION: n's can have any sequence except:
      ccccc ccccc cc
<220> FEATURE:
<221> NAME/KEY: misc_feature
<222> LOCATION: (5)..(20)
<223> OTHER INFORMATION: n is a, c, g, t or u

<400> SEQUENCE: 65 tcgtnnnnn nnnnnnnnnnn                                                 20

<210> SEQ ID NO 66
<211> LENGTH: 12
<212> TYPE: DNA
<213> ORGANISM: Artificial
<220> FEATURE:
<223> OTHER INFORMATION: Synthetic oligonucleotide
<220> FEATURE:
<221> NAME/KEY: n
<222> LOCATION: (5)..(12)
<223> OTHER INFORMATION: at least 50% of n's are c or at least 70% n's
      are t
<220> FEATURE:
<221> NAME/KEY: misc_feature
<222> LOCATION: (5)..(12)
<223> OTHER INFORMATION: n is a, c, g, t or u

<400> SEQUENCE: 66
tcgtnnnnnn nn                                                         12

<210> SEQ ID NO 67
<211> LENGTH: 100
<212> TYPE: DNA
<213> ORGANISM: Artificial
<220> FEATURE:
<223> OTHER INFORMATION: Synthetic oligonucleotide
<220> FEATURE:
<221> NAME/KEY: n
<222> LOCATION: (5)..(100)
<223> OTHER INFORMATION: any one or more n's at positions 8 to 100 could
      be missing
<220> FEATURE:
<221> NAME/KEY: misc_feature
<222> LOCATION: (5)..(100)
<223> OTHER INFORMATION: n is a, c, g, t or u

<400> SEQUENCE: 67 tcgannnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn                          100
```

```
<210> SEQ ID NO 68
<211> LENGTH: 23
<212> TYPE: DNA
<213> ORGANISM: Artificial
<220> FEATURE:
<223> OTHER INFORMATION: Synthetic oligonucleotide
<220> FEATURE:
<221> NAME/KEY: n
<222> LOCATION: (5)..(23)
<223> OTHER INFORMATION: at least 55% of all n's are pyrimidines
<220> FEATURE:
<221> NAME/KEY: misc_feature
<222> LOCATION: (5)..(23)
<223> OTHER INFORMATION: n is a, c, g, t or u

<400> SEQUENCE: 68
tcgannnnnn nnnnnnnnnn nnn                                           23

<210> SEQ ID NO 69
<211> LENGTH: 12
<212> TYPE: DNA
<213> ORGANISM: Artificial
<220> FEATURE:
<223> OTHER INFORMATION: Synthetic oligonucleotide
<220> FEATURE:
<221> NAME/KEY: n
<222> LOCATION: (5)..(12)
<223> OTHER INFORMATION: at least 50% of all n's are pyrimidines
<220> FEATURE:
<221> NAME/KEY: misc_feature
<222> LOCATION: (5)..(12)
<223> OTHER INFORMATION: n is a, c, g, t or u

<400> SEQUENCE: 69
tcgannnnnn nn                                                       12
```